(12) United States Patent
Tilly et al.

(10) Patent No.: US 9,150,830 B2
(45) Date of Patent: Oct. 6, 2015

(54) COMPOSITIONS FOR AUTOLOGOUS OVARIAN OOGONIAL STEM CELL MITOCHONDRIAL ENERGY TRANSFER

(75) Inventors: Jonathan L. Tilly, Windham, NH (US); Dori C. Woods, Weymouth, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/606,914

(22) Filed: Sep. 7, 2012

(65) Prior Publication Data

US 2013/0052727 A1 Feb. 28, 2013

Related U.S. Application Data

(63) Continuation of application No. 13/447,075, filed on Apr. 13, 2012, now Pat. No. 8,647,869.

(60) Provisional application No. 61/475,561, filed on Apr. 14, 2011, provisional application No. 61/600,505, filed on Feb. 17, 2012.

(51) Int. Cl.
*C12N 5/00* (2006.01)
*C12N 5/075* (2010.01)
*C12N 5/0735* (2010.01)

(52) U.S. Cl.
CPC ............ *C12N 5/0609* (2013.01); *C12N 5/0611* (2013.01); *C12N 2501/11* (2013.01); *C12N 2501/115* (2013.01); *C12N 2501/13* (2013.01); *C12N 2501/235* (2013.01); *C12N 2502/13* (2013.01); *C12N 2517/10* (2013.01)

(58) Field of Classification Search
None
See application file for complete search history.

(56) References Cited

U.S. PATENT DOCUMENTS

| 6,875,854 B1 | 4/2005 | Castrillon |
| 7,955,846 B2 | 6/2011 | Tilly et al. |
| 8,062,222 B2 | 11/2011 | Dertinger et al. |
| 2003/0134422 A1* | 7/2003 | Sayre .............................. 435/455 |
| 2005/0130302 A1 | 6/2005 | Nakauchi et al. |
| 2006/0010508 A1* | 1/2006 | Tilly et al. ....................... 800/18 |
| 2006/0010509 A1 | 1/2006 | Johnson et al. |
| 2006/0015961 A1 | 1/2006 | Tilly et al. |
| 2007/0010013 A1* | 1/2007 | Bukovsky et al. ............. 435/366 |
| 2009/0111764 A1 | 4/2009 | Hillis et al. |

FOREIGN PATENT DOCUMENTS

| EP | 1233978 A1 | 8/2002 |
| WO | WO01/30980 | 5/2001 |
| WO | WO01/30980 A2 * | 5/2001 |
| WO | WO-0136445 A1 | 5/2001 |
| WO | 0130980 A3 | 11/2001 |
| WO | WO-2005007687 A1 | 1/2005 |
| WO | WO2005/113752 | 12/2005 |
| WO | WO2005/121321 | 12/2005 |
| WO | WO/2006/001938 | 1/2006 |
| WO | 2010/124123 A1 | 10/2010 |
| WO | 2012142500 A2 | 10/2012 |

OTHER PUBLICATIONS

Molecular Probes, Invitrogen, p. 1-6, 2008).*
Perez et al (Cell Death and Differentiation, 14: 524-533, 2007).*
Sugrue et al (Biol Signals Recept, 10(3-4):176-88, 2001).*
ISR/Written Opinion issued in PCT/US2005/017233, Feb. 26, 2007, The General Hospital Corp.
ISR/Written Opinion/IPRP issued in PCT/US2005/017221, Jul. 27, 2006, The General Hospital Corp.
ISR/Written Opinion/IPRP issued in PCT/US2005/017234, Aug. 10, 2006, The General Hospital Corp.
Supplementary Search Report issued in EP-05779982.7, Sep. 17, 2008, The General Hospital Corp.
Supplementary Search Report issued in EP-05783644.7, Sep. 23, 2008, The General Hospital Corp.
Supplementary Search Report issued in EP-05782697.6, Oct. 15, 2008, The General Hospital Corp.
International Preliminary Report on Patentability issued for PCT/US05/17233, Jul. 25, 2008, The General Hospital Corp.
International Preliminary Report on Patentability issued for PCT/US05/17234, Jul. 25, 2008, The General Hospital Corp.
Powell, K., Going Against the Grain, PloS Biol 2007; 5:e338 (doi:10.1371/journal.pbio.0050338).
Bazer FW., Strong science challenges conventional wisdom: new perspectives on ovarian biology. Reprod Biol Endocrinol 2004; 2:28.
Gougeon A., Neo-oogenesis in the postnatal ovary: fantasy or reality? Gynecol Obstet Fertil 2005; 33:819-823.
Kayisli UA et al., Stem cells and fertility: what does the future hold? Curr Opin Obstet Gynecol 2006; 18:338-343.
Faddy M. et al., Numbers of ovarian follicles and testing germ line renewal in the postnatal ovary. Facts and fallacies. Cell Cycle 2007; 6:1951-1952.
Oktem O. et al., Stem cells: a perspective on oocytes. Ann NY Acad Sci USA 2008; 1127:20-26.
Zuckerman S., Beyond the Ivory Tower. The Frontiers of Public and Private Science. New York: Taplinger; 1971:22-34.
Waldeyer W. Eierstock and Ei. Engelmann, Leipzig; 1870.
Zhang D et al., Expression of stem and germ cell markers within nonfollicle structures in adult mouse ovary. Reprod Sci 2008; 15:139-146.
Vermande-Van Eck G. , Neo-ovogenesis in the adult monkey. Anat Rec 1956; 125:207-224.
Flaws JA, et al., Chronically elevated luteinizing hormone depletes primordial follicles in the mouse ovary. Biol Reprod 1997; 57:1233-1237.
Dissen GA, et al., Romero C., Hirshfield AN, Ojeda SR. Nerve growth factor is required for early follicular development in the mammalian ovary. Endocrinology 2001; 142:2078-2086.
Nilsson EE, et al., Bone morphogenetic protein-4 acts as an ovarian follicle survival factor and promotes primordial follicle development. Biol Reprod 2003; 69:1265-1272.

(Continued)

Primary Examiner — Deborah Crouch
Assistant Examiner — Magdalene Sgagias
(74) Attorney, Agent, or Firm — Saul Ewing LLP; Peter C. Lauro, Esq.

(57) ABSTRACT

Oogonial stem cell (OSC)-derived compositions, such as nuclear free cytoplasm or isolated mitochondria, and uses of OSC-derived compositions in autologous fertility-enhancing procedures are described.

17 Claims, 30 Drawing Sheets

(56) References Cited

OTHER PUBLICATIONS

Tomic D et al., Ovarian follicle development requires Smad3, Mol Endocrinol 2004; 18:2224-2240.

Rajkovia A et al., NOBOX deficiency disrupts early folliculogenesis and oocyte-specific gene expression. Science 2004; 305:1157-1159.

Castrillon DH et al., Suppression of ovarian follicle activation in mice by the transcription factor Foxo3a. Science 2004; 301:215-218.

Lohff JC et al., Effect of duration of dosing on onset of ovarian failure in a chemical-induced mouse model of perimenopause. Menopause 2006; 13:482-488.

Reddy P et al., Oocyte-specific deletion of Pten causes premature activation of the primordial follicle pool. Science 2008; 319:611-613.

Gosden RG. Ovarian support of pregnancy in ageing inbred mice. J Reprod Fertil 1975; 42:423-430.

Gosden RG. Effects of age and parity on the breeding potential of mice with one or two ovaries. J. Reprod Fertil 1979; 57:477-487.

Nelson JF et al., Effects of dietary restriction on estrous cyclicity and follicular reserves in aging C57BL/6Jmice. Biol Reprod 1985; 32:515-522.

Eichenlaub-Ritter U et al., The CBA mouse as a model for age-related aneuploidy in man: studies of oocyte maturation, spindle formation and chromosome alignment during meiosis. Chromosoma (Berl) 1988; 96:220-226.

Allen E. Ovogenesis during sexual maturity. Am J Anat 1923; 31:439-482.

Bucci LR et al., Effects of busulfan on murine spermatogenesis: cytotoxicity, sterility, sperm abnormalities and dominant lethal mutations. Mutat Res 1987; 176:259-268.

Brinster RL et al., Germline transmission of donor haplotype following spermatogonial transplantation. Proc Natl Acad Sci USA 1994; 91:11303-11307.

Ogawa T et al., Transplantation of testis germinal cells into mouse seminiferous tubules. Int J Dev Biol 1997; 41:111-122.

Pelloux MC et al., Effects of busulphan on ovarian folliculogenesis, steroidogenesis and anti-Mullerian activity of rat neonates. Acta Endocrinol 1988; 118:218-226.

Perez GI et al., Apoptosis-associated signaling pathways are required for chemotherapy-mediated female germ cell destruction. Nat Med 1997; 3:1228-1232.

Perez GI et al., Fragmentation and death (a.k.a. apoptosis) of ovulated oocytes. Mol Hum Reprod 1999; 5:414-420.

Morita Y et al., Oocyte apoptosis is suppressed by disruption of the acid sphingomyelinase gene or by sphingosine-1-phosphate therapy. Nat Med 2000; 6:1109-1114.

Baltus AE et al., In germ cells of mouse embryonic ovaries, the decision to enter meiosis precedes premeiotic DNA replication. Nat Genet 2006; 38:1430-1434.

Zhou Q et al., Expression of stimulated by retinoic acid gene 8 (Stra8) and maturation of murine gonocytes and spermatogonia induced by retinoic acid in vitro. Biol Reprod 2008; 78:537-545.

Wang N et al., Inhibition of histone deacetylase activity amplifies retinoic acid-mediated induction of Stra8 expression and oogenesis in ovaries of adult female mice. Proceedings of the 41st Annual Meeting of the Society for the Study of Reproduction, Kailua-Kona, Big Island, HI; p. 132 (Abstract 291).

Bowles J et al., Retinoic acid signaling determines germ cell fate in mice. Science 2006; 312:596-600.

Koubova J et al., Retinoic acid regulates sex-specific tijming of meiotic initiation in mice. Proc Natl Acad Sci USA 2006; 103:2474-2479.

Lee H-J et al., Loss of CABLES1, a cyclin-dependent kinase-interacting protein that inhibits cell cycle progression, results in germline expansion at the expense of oocyte quality in adult female mice. Cell Cycle 2007; 6:2678-2684.

Bristol-Gould SK et al., Postnatal regulation of germ cells by activin: the establishment of the initial follicle pool. Dev Biol 2006; 298:132-148.

Lin H. The stem-cell niche theory: lessons from flies. Nat Rev Genet 2002; 3:931-940.

Ogawa T et al., The niche for spermatogonial stem cells in the mammalian testis. Int. J. Hematol 2005; 82: 381-388.

Bukovsky A et al., Origin of germ cells and formation of new primary follicles in adult human ovaries. Reprod Biol Endocrinol 2004; 2:28.

Bukovsky A et al., Oogenesis in cultures derived from adult human ovaries. Reprod Biol Endocrinol 2005; 3:17.

Bukovsky A et al., Mammalian neo-oogenesis and expression of meiosis-specific protein SCP3 in adult human and monkey ovaries. Cell Cycle 2008; 7:683-686.

Bristol-Gould SK et al., Fate of the initial follicle pool: empirical and mathematical evidence supporting its sufficiency for adult fertility. Dev Biol 2006; 298:149-154.

Peters H. The development of the mouse ovary from birth to maturity. Acta Endocrinol 1969; 62:98-116.

Elvin JA et al., Molecular characterization of the follicle defects in the growth differentiation factor 9-deficient ovary. Mol Endocrinol 1999; 13: 1018-1034.

Myers M et al., Methods for quantifyying follicular numbers within the mouse ovary. Reproduction 2004; 127:569-580.

Huntriss J et al., cDNA cloning and expression of the human NOBOX gene in oocytes and ovarian follicles. Mol Hum Reprod 2006; 12:283-289.

John GN et al., Specificity of the requirement for Foxo3 in primordial follicle activation. Reproduction 2007; 133:855-863.

Ohta H et al., Commitment of fetal male germ cells to spermatogonial stem cells during mouse embryonic development. Biol Reprod 2004; 70:1286-1291.

Hubner K et al., Derivation of oocytes from mouse embryonic stem cells. Science 2003; 300:1251-1256.

Novak I et al., Mouse embryonic stem cells form follicle-like ovarian structures but do not progress through meiosis. Stem Cells 2006; 8:1931-1936.

Kerkis A et al., In vitro differentiation of male mouse embryonic stem cells into both presumptive sperm cells and oocytes. Cloning Stem Cells 2007; 9:535-548.

Nagano MC. In vitro gamete derivation from pluripotent stem cells: progress and perspective. Biol Reprod 2007; 76:546-551.

Dyce PW et al., In vitro germline potential of stem cells derived from fetal porcine skin. Nat Cell Biol 2006; 8:384-390.

Dyce PW et al., From skin cells to ovarian follicles? Cell Cycle 2006; 5:1371-1375.

Danner S et al., Derivation of oocyte-like cells from a clonal pancreatic stem cell line. Mol Hum Reprod 2007; 13:11-20.

Toyooka Y et al., Embryonic stem cells can form germ cells in vitro. Proc Natl Acad Sci USA 2003; 100:11457-11462.

Geijsen N et al., Derivation of embryonic germ cells and male gametes from embryonic stem cells. Nature 2004; 427:148-154.

Lue Y et al., Fate of bone marrow stem cells transplanted into the the testis: implications for men with testicular failure. Am J Pathol 2007; 170;899-908.

Drusenheimer N et al., Putative human male germ cells from bone marrow stem cells. Soc Reprod Fertil Suppl 2007; 63:69-76.

Yeom YI et al., Germline regulatory element of Oct-4 specific for the totipotent cycle of embryonal cells. Development 122:881-894.

Yoshimizu T et al., Germline-specific expression of the Oct-4/green fluorescent protein (GFP) transgene in mice. Dev Growth Differ 1999; 41:675-684.

Szabo PE et al., Allele-specific expression of imprinted genes in mouse migratory primordial germ cells. Mech Dev 2002; 115:157-160.

Begum S et al., The oocyte population is not renewed in transplanted or irradiated adult ovaries. Hum Reprod 2008; (doi:10.1093/humrep/den249).

Fu X et al., Bone marrow mesenchymal stem cell transplanation improves ovarian function and structure in rats with chemotherapy-induced damage. Cytotherapy 2008; 10:353-363.

Tilly JL et al., Stem cell contribution to ovarian development, function and disease. Endocrinology 2008; (doi:10.1210/en.2008-0458).

Shankle WR et al., Evidence for a postnatal doubling of neuron number in the developing human cerebral cortex between 15 months and 6 years. J Theor Biol 1998; 191:115-140.

(56) References Cited

OTHER PUBLICATIONS

Shankle WR et al., Approximate doubling of numbers of neurons in postnatal human cerebral cortex and in 35 specific cytoarchitectural areas from birth to 72 months. Pediatr Dev Pathol 1999; 2:244-259.
Gould E et al., Neurogenesis in the neocortex of adult primates. Science 1999; 286:548-552.
Korr H et al., Facts and fictions regarding post-natal neurogenesis in the developing human cerebral cortex. J Theor Biol 1999; 200:291-297.
Nowakowski RS et al., New Neurons: extraordinary evidence or extraordinary conclusion? Science 2000; 288:771a.
Rakic P. Neurogenesis in the adult primate neocortex: an evaluation of the evidence. Nat Rev Neurosci 2002; 3:65-71.
Blakeslee S. A decade of discovery yields a shock about the brain. New York Times Jan. 2000; F1, F4.
Gross CG. Neurogenesis in the adult brain: death of a dogma. Nat Rev Neurosci 2000; 1:67-73.
Gould E et al., Adult-generated hippocampal and neocortical neurons in macaques have a transient existence. Proc Natl Acad Sci USA 2001; 98: 10910-10917.
Gould E et al., Neurogenesis in adult mammals: some progress and problems. J Neurosci 2002; 22:619-623.
Leuner B et al., Diminished neurogenesis in the marmoset brain precedes old age. Proc Natl Acad Sci USA 2007; 104:17169-17173.
Revishchin AV et al., Neural stem cells in the mammalian brain. Int Rev Cytol 2008; 265-55-109.
Maurer MH et al., Screening the brain: molecular fingerprints of neural stem cells. Curr Stem Cell Res Ther 2006; 1:65-77.
Taupin P. Therapeutic potential of adult neural stem cells. Rec Patents CNS Drug Discov 2006; 1:299-303.
Beaumont HM et al., A quantitative and cytological study of oogonia and oocytes in the fetal and neonatal rat. Proc R Soc Lond B 1961; 155:557-579.
Baker TG et al., The fine structure of oogonia and oocytes in human ovaries. J Cell Sci 1967; 2:213-224.
Gosden RG. Follicular status at menopause. Hum Reprod 1987; 2:617-621.
Selesniemi K et al., Moderate caloric restriction initiated in rodents during adulthood sustains function of the female reproductive axis into advanced chronological age. Aging Cell 2008; (doi:10.1111/j.1474-9726.2008.00409.x).
Perez GI et al., Absence of the pro-apoptotic Bax protein extends fertility and alleviates age-related health complications in female mice. Proc Natl Acad Sci USE 2007; 104: 5229-5234.
Kirilly D et al., The Drosophila ovary: an active stem cell community. Cell Res 2007; 17:15-25.
Pearl R et al., Studies on the physiology of reproduction in the domestic fowl. J Exp Zool 1921; 34:101-118.
Underwood JL et al., Gonad regeneration in grass carp following bilateral gonadectomy. Progressive Fish-Culturist 1986; 48:54-56.
Draper BW et al., nanos1 is required to maintain oocyte production in adult zebrafish. Dev Biol 2007; 305:589-598.
Salooja N et al., Successful pregnancies in women following single autotransplant for acute myeloid leukemia with a chemotherapy ablation protocol. Bone Marrow Transplant 1994; 13:431-435.
Socie G et al., Late Effects Working Party of the European Study Group for Blood and Marrow Transplantation. Nonmalignant late effects after allogeneic stem cell transplantation. Blood 2003; 101:3373-3385.
Oktay K et al., Regeneration of oocytes after chemotherapy: connecting the evidence from mouse to human. J. Clin Oncol 2007; 25:3185-3187.
Tropel P et al., Isolation and Characterization of Mesenchymal Stem Cells from Adult Mouse Bone Marow. Experimental Cell Research, May 1, 2004. 295(2); 395-406.
Logothetou-Rella "Description of primordial germ cells, oogonia, oocytes and embryo-like growth in squash preparations of tissues from hematological malignancies" Histol Histopathol. 11(4): 965-984 (1996).

Nayernia et al. "Derivation of male germ cells from bone marrow stem cells" Lab Invest. 86(7): 654-663 (2006).
Johnson et al. "Oocyte Generation in Adult Mammalian Ovaries by Putative Germ Cells in Bone Marrow and Peripheral Blood" Cell 122: 303-315 (2005).
Kucia et al. "A population of very small embryonic-like (VSEL) CZCR4+SSEA-1+ Oct-4+ Stem cells identified in adult bone marrow" Luekemia 20: 857-869 (2006).
Pochampally et al. "Serum deprivation of human marrow stromal cells (hMSCs) selects for a subpopulation of early progenitor cells with enhanced expression of OCT-4 and other embryonic genes" Blood 103(5): 1647-1652 (2004).
Hayashi et al. "Mouse preimplantation Embryos Developed from Oocytes Injected with Round Spermatids or Spermatozoa Have Similar but Distinct Patterns of Early Messenger RNA Expression" Biology of Reproduction 69: 1170-1176 (2003).
Hovatta et al. "A culture system using human foreskin fibroblasts as feeder cells allows production of human embryonic stem cells" Human Reproduction 18(7): 1404-1409 (2003).
Bukovsky et al. "Potential new strategies for the treatment of ovarian infertility and degenerative diseases with autologous ovarian stem cells" Expert Opin. Biol. Ther. 6(4): 341-365 (2006).
Eggan et al. "Ovulated oocytes in adult mice derive from non-circulating germ cells." Nature 441; 1109-1114 (2006).
Anderson, Biol Reprod. 1988; 38(1) 1-15.
Decotto et al., Dev cell. 2005; 9(4): 501-10.
Gage, F., Nature 392: 18-24, 1998.
Goswami et al., 2005. Premature Ovarian Failure. Hum Reprod Update 11: 391-410.
Hildebrandt et al., 2000. Detection of Germ-cell Tumor Cells in Peripheral Blood Progenitor Cell Harvests: Impact on Clinical Outcome. Clin Cancer Res 6: 4641-4646.
Samstein et al., Journal of American Society of Nephrology 12: 182-193, 2001.
Virant-Klun et al., Stem Cells and Development, Jul. 2008 pp. 1-43.
Yamashita et al., Journal of Cell Science 118, 665-672, 2005.
Powell "Skeptics demand duplication of controversial fertility claim" Nat Med 11:911 (2005).
Powell "Born or made? Debate on mouse eggs reignites" Nature 441: 795 (2006).
Ainsworth "Bone cells linked to creation of fresh eggs in mammals" Nature 436: 609 (2005).
Greenfeld et al. "Renewed debate over postnatal oogenesis in the mammalian ovary" Bioessays 26:829-32 (2004).
Gosden "Germline stem cells in the postnatal ovary: is the ovary more like a testis?" Hum Reprod Update 10(3) 193-195 (2004).
Albertini "Micromanagement of the ovarian follicle reserve—do stem cells play into the ledger?" Reproduction 127: 513-514 (2004).
Vogel "Controversial study finds unexpected source of oocytes" Science 309: 678-679 (2005).
Hoyer Can the clock be turned back on ovarian aging? Sci Aging Knowledge Environ 10:pe11 (2004).
Telfer "Germline stem cells in the postnatal mammalian ovary: a phenomenon of prosimian primates and mice?" Reprod Biol Endocrinol 2:24 (2004).
Telfer et al. "On regenerating the ovary and generating controversy" Cell 122: 821-22 (2005).
Kerr et al. "Quantification of healthy follicles in the noenatal and adult mouse ovary: evidence for maintenance of primordial follicle supply" Reproduction 132: 95-109 (2006).
Skaznik et al. "Serious doubts over Eggs forever?" Differentiation 74: 1-7 (2006).
Salooja et al. "Late Effects of working party of the European Group for blood and marrow transplantataion. Pregnancy outcomes after peripheral blood or bone marrow transplantation: a retrospective study." Lancet 358: 271-276 (2001).
Samuelsson et al. "Successful pregnancy in a 28 year old patient autographed for acute lymphoblastic leukemia following myeloablative treatment including total body irradiation." Bone Marrow Transplant 12: 659-660 (1993).
Sanders et al. "Pregnancies following high-dose cyclophosphamide with or without high-dose busulfan or total-body irradiation and bone marrow transplantation." Blood 87: 3045-3052 (1996).

(56) References Cited

OTHER PUBLICATIONS

Johnson et al. "Germline stem cells and follicular renewal in the postnatal mammalian ovary." Nature 48(11):145-150 (2004).
Hershlag et al. "Return of fertility after autologous stem cell transplantation." Fertility and Sterility 77(2) 419-421 (2002).
Zhou, K, et al. "Production of Offspring from a Germline Stem Cell Line Derived from Neonatal Ovaries" Nature Cell Biology Online Publication, published online Apr. 12, 2009; DOI 10.1038/ncb1869, pp. 1-20.
Tropel et al., Isolation and Characterization of Mesenchymal Stem Cells from Adult Mouse Bone Marrow. Experimental Cell Research, May 1, 2004. 295(2); 395-406.
Wittstock et al., Analytical Biochemistry, 292, 166-169, 2001.
Castrillon et al., (PNAS, 97-17: 9585-9590, 2000).
Clark, et al., (Stem Cells, 22: 169-179, 2004).
Johnson et al. "Germline stem cells and follicular renewal in the postnatal mammalian ovary" Nature 428: 145-150 (2004).
Byskov et al. "Eggs forever?" Differentiation 73: 438-446 (2005).
Johnson et al. "Setting the Record Straight on Data Supporting Postnatal Oogenesis in Female Mammals" Cell Cycle 4:11, 14771-1477 (2005).
Logothetou-Rella Description of primordial germ cells, oogonia, oocytes and embryo-like growth in squash preparations of issues from hematological malignancies: Histology and Histopathology 11: 965-984(1996).
Logothetou-Rella "Meiosis in hematological malignancies. In situ cytogenetic morphology" Histology and Histopathology 11: 943-963 (1996).
Thomson et al., Science, 282: 1145-1147, 1998.
Clark et al., Human Molecular Genetics, 13(7): 727-739, 2004.
Reubinoff et al., Nature Biotechnology, 18: 399-404, 2000.
Lin et al., Stem Cells, 21: 152-161, 2003.
Gosden, Human Reproduction Update, 10(3): 193-195, 2004.
Bukovsky, et al., Reproductive Biology and Endocrinology, 2:20, 2004.
Spradling, Nature, 428: 133-134, 2004.
Balakier et al., "Morphological and Cytogenetic Analysis of Human Giant Oocytes and Giant Embryos" Human Reproduction 17(8): 2394-2401 (2002).
Sotile "Bone Marrow as a Source of Stem Cells and Germ Cells? Perspectives for Transplantation" Cell Tissue Res. 328:1-5 (2007).
Hua, Jinlian et al., Derivation of male germ cell-like lineage from human fetal bone marrow stem cells, Reproductive BioMedicine Online; www.rbmonline.com/Article/3742 on web May 8, 2009, vol. 19, No. 1. 2009-99-105.
Lovell-Badge, Robin, Banking on spermatogonial stem cells: Frozen assets and foreign investments, Nature Medicine, vol. 2, No. 6, Jun. 1996.
Meachem et al., Spermatogonia: stem cells with a great perspective, Reproduction (2001), 121, 825-834.
Nistal et al., Decrease in the Number of Human Ap and Ad Spermatogonia and in the Ap/Ad Ratio with Advancing Age, J Androl 1987; 8:64-68.
Paniagua et al., Quantification of cell types throughout the cycle of the human seminiferous epithelium and their DNA content, Anatomy and Embryology (1987) 176: 225-230.
Schulze, Cornelia, Response of the human testis to long-term estrogen treatment: Morphology of Sertoli cells, Leydig cells and spermatogonial stem cells, Cell and Tissue Research (1998) 251: 31-43.
Anderson "An overview of follicular development in the ovary: From embryo to the fertilized ovum in vitro." Md. Med. J. 41: 614-620 (1992).
Johnson et al., "Germline stem cells and follicular renewal in the postnatal mammalian ovary." Nature 428: 145-150 (2004).
Korbling et al. "Peripheral blood stem cell versus bone barrow allotransplantation: does the source of hematopoietic stemm cells matter?" Blood 98: 2900-2908 (2001).
Ho et al., "Hematopoietic stem cells: can old cells learn new tricks?" J Leukoc Biol 73: 547-555 (2003).
Sanchez-Ramos "Neural Cells Derived From Adult Bone Marrow and Umbilical Cord Blood." J Neurosci Res 69: 880-893 (2002).
Lee "Isolation of multipotent mesenchymal stem cells from umbilical cord blood." Blood 103:1669-75 (2004).
Rogers et al. "Lifeline in an Ethical Quagmire: Umbilical Cord Blood as an Alternative to Embryonic Stem Cells." Sexuality, Reproduction & Menopause 2: 64-70 (2004).
Green et al. "Do cells outside the testes participate in repopulating the germinal epithelium after irradiation?" Int. J. Radiat. Biol. vol. 17 (1): 87-92 (1970).
Morita et al. "Oocyte Apoptosis: Like Sand through an Hourglass" Dev. Biol. 213: 1-17 (1999).
Tilly, J.L., "Commuting the Death Sentence: How Oocytes Strive to Survive." Nat. Rev. Mol. Cell Biol. 2: 838-848 (2001).
Faddy et al., "The kinetics of pre-antral follicle development in ovaries of CBA/Ca mice during the first 14 weeks of life." Cell Tissue Kinet. 20: 551-560 (1987).
Faddy, M.J., "Follicle dynamics during ovarian ageing." Mol. Cell. Endocrinol. 163: 43-48 (2000).
Faddy et al., "An Analytical Model for Ovarian Follicle Dynamics." J. Exp. Zool. 197: 173-186 (1976).
Richardson et al. "Follicular Depletion During the Menopausal Transition: Evidence for Accelerated Loss and Ultimate Exhaustion." J. Clin. Endocrinol. Metab. 65: 1231-1237 (1987).
Borum "Oogenesis in the Mouse, A Study of the Meiotic Prophase." Exp. Cell Res. 24: 495-507 (1961).
McLaren "Meiosis and Differentiation of Mouse Germ Cells." Symp. Soc. Exp. Biol. 38: 7-23 (1984).
Peters "Migration of gonocytes into the mammalian gonad and their differentiation." Phil. Trans. R. Soc. Lond. B, 259: 91-101 (1970).
Waxman "Chemotherapy and the adult gonad: a review." J. R. Soc. Med. 76: 144-8 (1983).
Familiari et al., "Ultrastructure of human ovarian primordial follicles after combination chemotherapy for Hodgkin's disease." Hum. Reprod. 8: 2080-7 (1993).
Ried et al. "Radiation-Induced Changes in Long-Term Survivors of Childhood Cancer After Treatment with Radiation Therapy." Semin. Roentgenol. 29: 6-14 (1994).
Reichman et al. "Breast Cancer in Young Women: Effect of Chemotherapy on Ovarian Function, Fertility, and Birth Defects." J. Natl. Cancer Inst. Monogr. 16: 125-9 (1994).
Tilly "Recent Arguments Against Germ Cell Renewal in the Adult Human Ovary." Cell Cycle, 6:8, 879-883, (2007).
Veitia et al, "Recovery of Female Fertility After Chemotherapy, Irradiation, and Bone Marrow Allograft: Further Evidence Against Massive Oocyte Regeneration by Bone Marrow-Derived Germline Stem Cells." Stem Cells, DOI: 10.1634/stemcells.2006-0770 (2007).
Lee et al. "Bone Marrow Transplantation Generates Immature Oocytes and Rescues Long-Term Fertility in a Preclinical Mouse Model of Chemotherapy-Induced Premature Ovarian Failure."J Clin Oncol.; 25: 3198-3204 (2007).
Liu et al., "Germline stem cells and neo-oogenesis in the adult human ovary." Dev. Biol. (DOI: 10.1016./j.ydbio.2007.03.006 (2007).
Gougeon et al. "Regulation of Ovarian Follicular Development in Primates: Facts and Hypotheses." Endocr Rev. 17: 121-55 (1996).
Zuckerman "The Number of Oocytes in the mature Ovary." Recent Prog. Norm. Res. 6: 63-108 (1951).
Perez et al. Nature Genetics 21:200-203 (1999).
Fujiwara, et al., Isolation of a DEAD-family protein gene that encodes a murine homolog of Drosophila vasa and its specific expression in germ cell lineage, Proc. Natl. Acad. Sci. USA, vol. 91, pp. 12258-12262, Dec. 1994.
Pacchiarotti, et al., Differentiation Potential of Germ Line Stem Cells Derived from the Postnatal Mouse Ovary, International Society of Differentiation (2010), doi: 10.1016/j.diff.2010.01.001.
Ghadami et al., Intravenously Injected Bone Marrow Cells Restore Ovarian Folliculogenesis and Steroid Hormones Production in Female FSHE (-1-) Mice. Reproductive Sciences, 15(1) (Supplement)—Abstract No. 597, Jan. 2008.
Virant-Klun, et al., Putative Stem Cells with an Embryonic Character Isolated from the Ovarian Surface Epithelium of Women with no Naturally Present Follicles and Oocytes. Differentiation, pp. 1-14, DOI: 10.111/j. 1432-0436.2008.00268.x Feb. 2008.

(56) References Cited

OTHER PUBLICATIONS

Webster's Ninth New Collegiate Dictionary, Merriam-Webster Inc., 2000, Springfield, MA (web excerpt—definition of "correspond").
Noce et al., Vasa homolog genes in mammalian germ cell development. Cell Struct Funct 26:131-136, 2001.
Zuckerman, Recent Prog Horm Res 1951; 6:63-108.
Johnson et al., Nature 2004; 428:145-150.
Spradling, *Nature* 2004 428:133-134.
Zou et al., Nat Cell Biol 2009: 11:631-636.
Johnson et al., Cell 2005; 122:303-315.
Wang et al., Cell Cycle 2010; 9:339-349.
Niikura et al., Aging 2010; 2:999-1003.
Tilly et al., Biol Reprod 2009; 80:2-12.
Tilly et al., Mol Hum Reprod 2009; 15:393-398.
Niikura et al., Aging 2009; 1:971-978.
Massasa et al., Aging 2010; 2:1-2.
Ventura *Vital Health Stat* 47:1-27, 1989.
Matthews NCHS Data Brief 21:1-8, 2009.
Henderson et al., *Nature* 218:22-28, 1968.
Hassold et al., *Hum Genet* 70:11-17, 1985.
Battaglia et al., *Hum Reprod* 11:2217-2222, 1996.
Hunt et al., *Trends Genet* 24:86-93, 2008.
Tarin et al., *Mol Reprod Dev* 61:385-397, 2002.
Tarin et al., *Theriogenology* 57:1539-1550, 2002.
Bentov et al., Fertil Steril 2010; 93(1):272-5. Epub Sep. 2009.
Bartmann et al., J Assist Reprod Genet 2004; 21:79-83.
Wilding et al., Zygote 2005; 13:317-23.
Zhang et al., *Cell Res* 16:841-850, 2006.
Van Blerkom et al., *Hum Reprod* 10:415-424, 1995.
Folsted et al., Biotechnol. Prog. 2002 18(1):1-5.
Cohen et al., Mol Hum Reprod 1998; 4:269-80.
Barritt et al., Hum Reprod 2001; 16:513-6.
Muggleton-Harris et al., Nature 1982; 299:460-2.
Harvey et al., Curr Top Dev Biol 2007; 77:229-49.
Sutovsky et al., *Biol Reprod* 63:5820590, 2000.
Acton et al., Biol Reprod 2007; 77: 569-76.
CBER 2002 Meeting Documents, Biological Response Modifiers Advisory Committee minutes from May 9, 2002 (publically available from the FDA at http://www.fda.gov/BiologicsBloodVaccines/SafetyAvailability/ucm105852.htm) Letter to.
Sponsors / Researchers—Human Cells Used in Therapy Involving the Transfer of Genetic Material by Means Other Than the Union of Gamete Nuclei (publically available from the FDA at http://www.fda.gov/BiologicsBloodVaccines/SafetyAvailability/ucm105852.htm).
Ramalho-Santos et al., *Hum Reprod Update*. 2009 (5):55 3-72.
Pachiarotti et al., *Differentiation* 2010 79:159-170.
Tarin et al., *Biol Reprod* 2001 65:141-150.
Pan et al., *Dev Biol* 2008 316:397-407.
Duncan et al., *Biol Reprod* 2009 81:768-776.
Sinclair Mech Ageing Dev 2005 126(9):987-1002.
Selesniemi et al. *Aging Cell* 7:622-629, 2008.
Yang et al., Cell 2008.
Hafner et al. *Aging* 2010, vol. 2, No. 12, pp. 914-923.
Tarin et al., *Hum Reprod* 1995 10:1563-1565.
Yang et al., *Exp Gerontol* 2006 41: 718-726.
ISR issued in PCT/US2012/033643 (WO-2012/142500), Oct. 10, 2012.
Written Opinion issued in PCT/US2012/033643 (WO-2012/142500), Oct. 10, 2012.
ISR issued in PCT/US2012/033672, Oct. 16, 2012.
Written Opinion issued in PCT/US2012/033672, Oct. 16, 2012.
Short et al., PNAS USA, Apr. 12, 2005 102(15): 5618-5623.
Lu et al., Anal. Chem., Oct. 1, 2004 76(19): 5705-5712.
Baas T.: "Repowering the ovary", SCIBX: Science-Business Exchange, vol. 5, No. 10, Mar. 8, 2012, pp. 1-3.
Blerkom Van J. et al.: "Mitochondrial Transfer Between Oocytes: Potential Applications of Mitochondrial Donation and the Issue of Heteroplasmy", Human Reproduction, vol. 13, No. 10, Jan. 1, 1998, pp. 2857-2868.
Database Medline [Online] US National Library of Medicine (NLM), Bethesda, MD, US; Feb. 2004.
Yu-Chiao et al.: "Mitochondria Transfer Can Enhance the Murine Embryo Development", Journal of Assisted Reproduction and Genetics, vol. 24, No. 10, Aug. 29, 2007, pp. 445-449.
Perez G. I et al.: "Further Studies on the Role of Mitochondria in Controlling Oocyte Apoptosis", Biology of Reproduction, vol. 62, No. Suppl. 01, Jan. 1, 2000, p. 132.
Masahito Tachibana et al.: "Mitochondrial Gene Replacement in Primate Offspring and Embryonic Stem Cells", Nature, vol. 461, No. 7262, Aug. 26, 2009, pp. 367-372.
Li-Ya Wang et al.: "Mitochondrial Functions on Oocytes and Preimplantation Embryos", Journal of Zhejiang University Science B, vol. 10, No. 7, Jul. 1, 2009, pp. 483-492.
Lonergan et al.: "Mitochondria in Stem Cells", Mitochondrion, vol. 7, No. 5, Aug. 28, 2007, pp. 289-296.
Yvonne A R White et al.: "Oocyte Formation by Mitotically Active Germ Cells Purified From Ovaries of Reproductive-Age Women", Nature Medicine, vol. 18, No. 3, Feb. 26, 2012, pp. 413-421.
Dori C Woods et al.: "The Next (Re) Generation of Ovarian Biology and Fertility in Women: Is Current Science Tomorrow's Practice?", Fertility and Sterility, vol. 98, No. 1, May 3, 2012, pp. 3-10.
Supplementary European Search Report, European Patent Application No. 12770662.2 (PCT/US2012/033643), Apr. 28, 2014.

\* cited by examiner

FIG. 3A
FIG. 3B
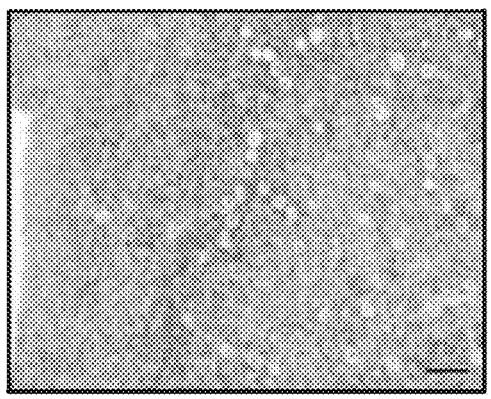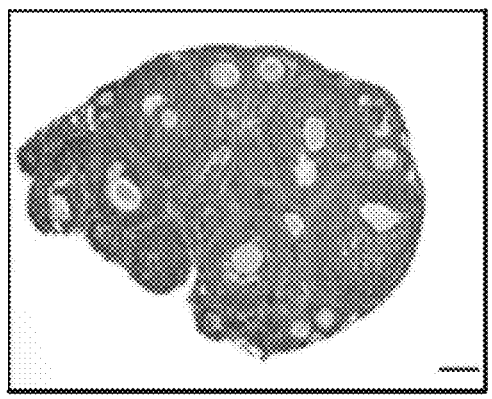
FIG. 3C
FIG. 3D
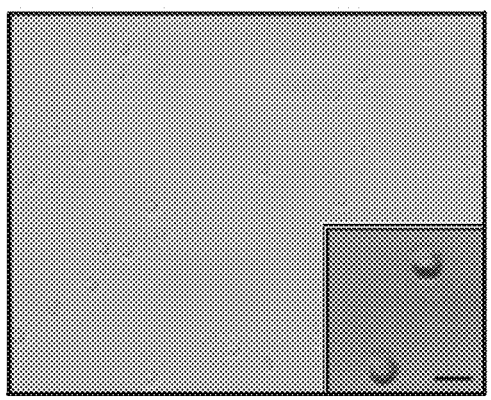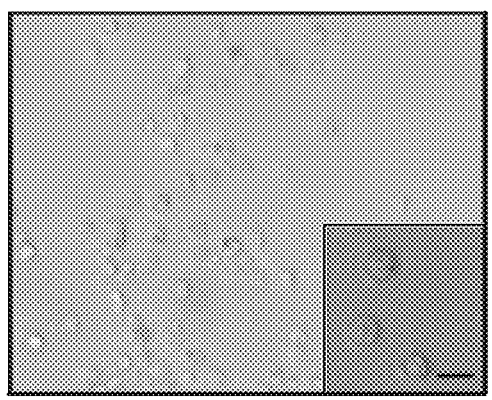
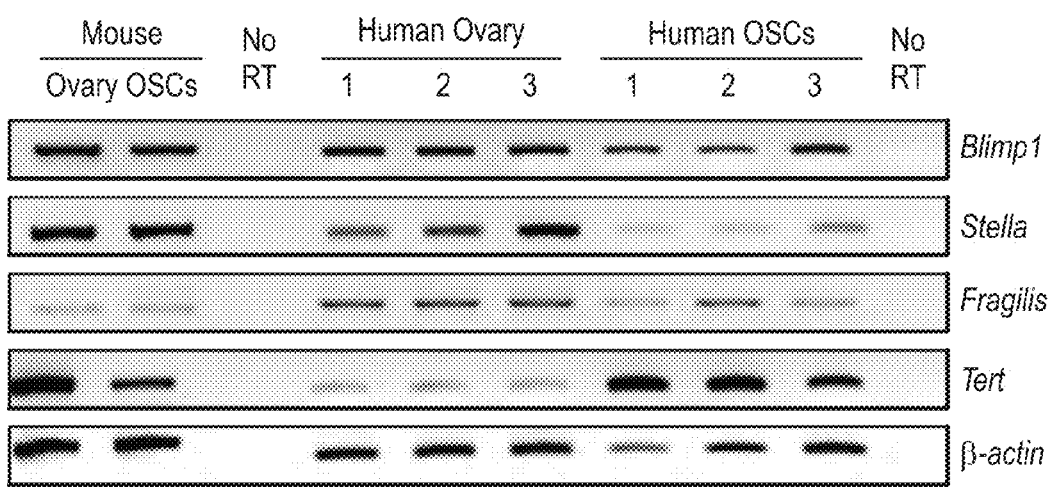
FIG. 3E FIG. 4A GFP-negative oocytes FIG. 4B GFP-positive oocytes

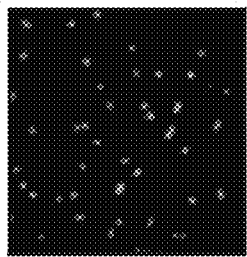 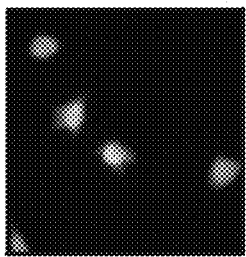 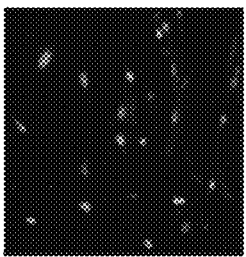 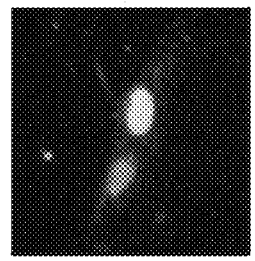
FIG. 6A  FIG. 6B  FIG. 6C  FIG. 6D
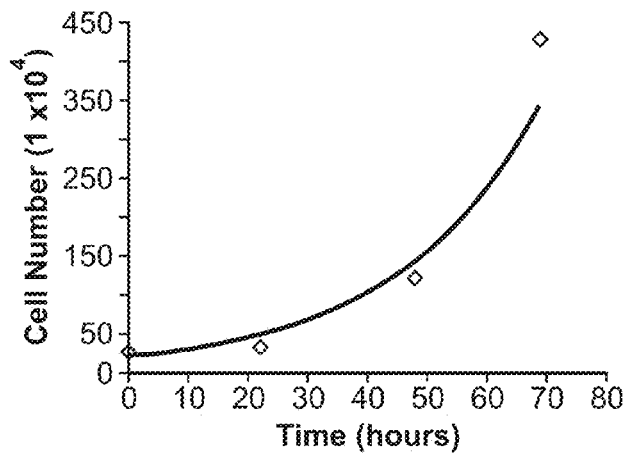
FIG. 6E
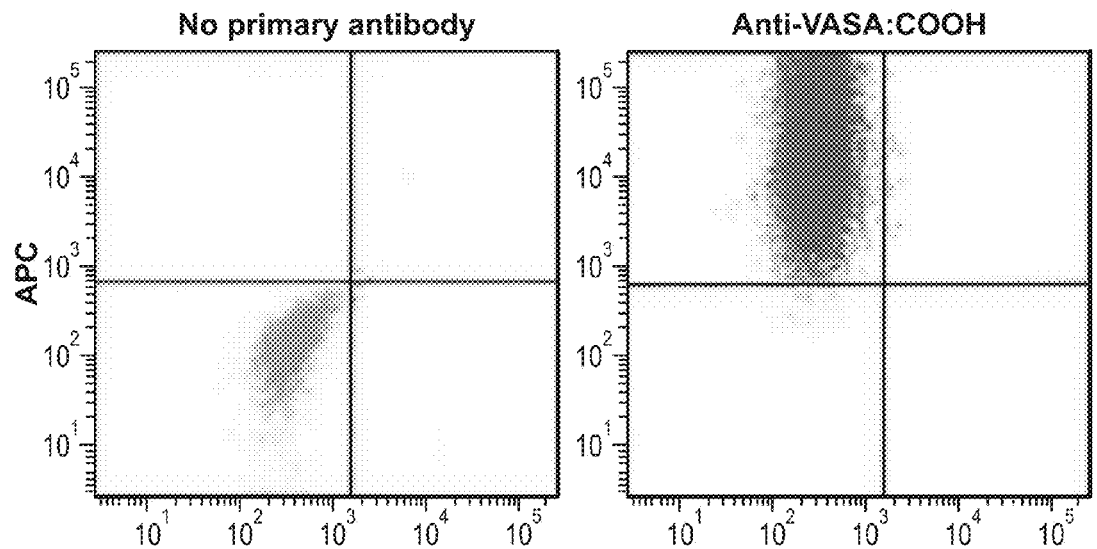
FIG. 6F

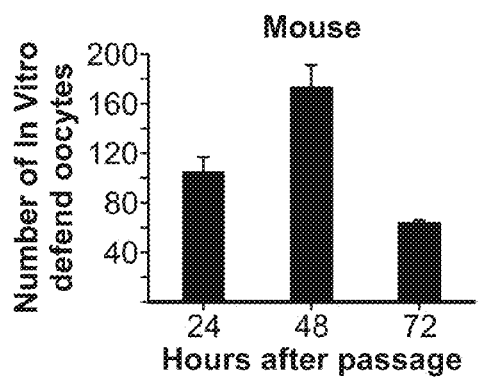
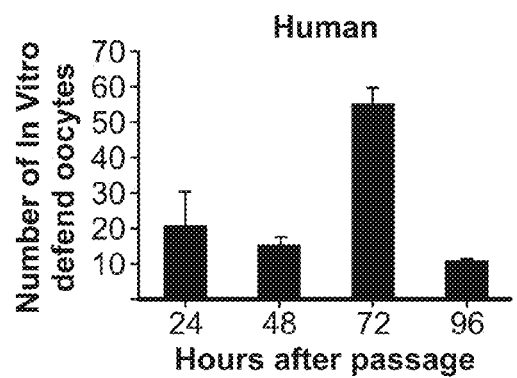
FIG. 7D  FIG. 7E
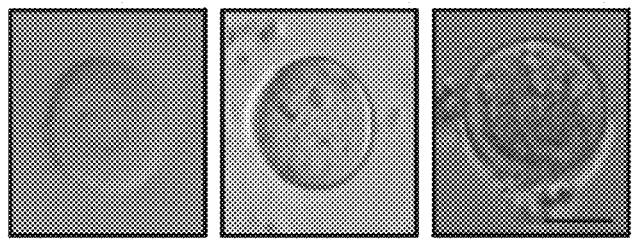
FIG. 7F
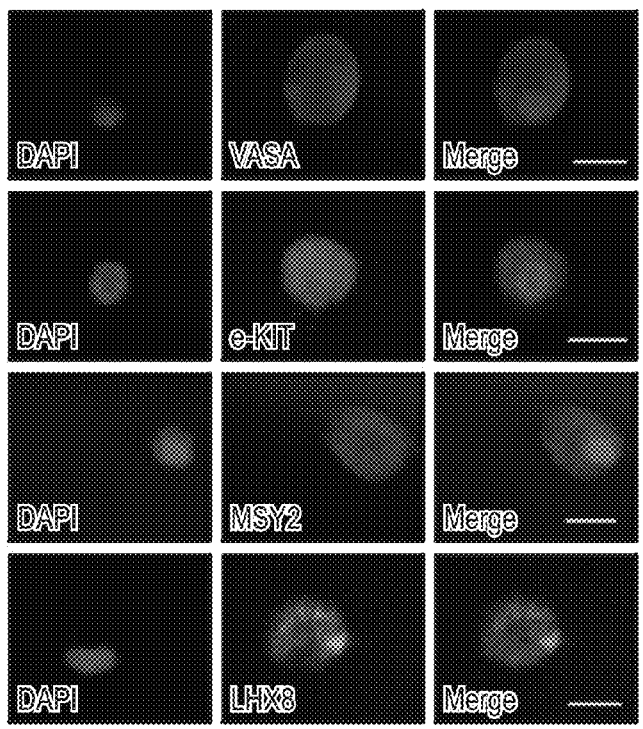
FIG. 7G

Example of FACS-based isolation of germ cells from bone marrow mononuclear cell preparations, based on cell-surface expression of VASA Example of FACS-based isolation of germ cells from peripheral blood mononuclear cell preparations, based on cell-surface expression of VASA

COMPOSITIONS FOR AUTOLOGOUS OVARIAN OOGONIAL STEM CELL MITOCHONDRIAL ENERGY TRANSFER

RELATED APPLICATIONS

This application is a continuation of U.S. application Ser. No. 13/447,075, filed Apr. 13, 2012, which claims benefit under 35 U.S.C. §119(e) of U.S. provisional application Ser. No. 61/475,561, filed Apr. 14, 2011 and U.S. provisional application Ser. No. 61/600,505, filed Feb. 17, 2012, the entire disclosures of which are incorporated herein by reference.

SEQUENCE LISTING

The instant application contains a Sequence Listing which has been submitted in ASCII format and is hereby incorporated by reference in its entirety. Said electronic copy, submitted on Sep. 7, 2012, is identified as item 09323b67813c4fe7 and is 15,466 bytes in size.

STATEMENT OF RIGHTS TO INVENTIONS MADE UNDER FEDERALLY SPONSORED RESEARCH

This work was supported in part by National Institutes on Aging Grant No. NH R37-AG012279 and National Institutes of Health National Research Service Award (F32-AG034809). The government has certain rights to the invention.

BACKGROUND OF THE INVENTION

During the past few decades, because of cultural and social changes, women in the developed world have significantly delayed childbirth. For example, first birth rates for women 35-44 years of age in the United States have increased by more than 8-fold over the past 40 years (Ventura *Vital Health Stat* 47:1-27, 1989 *Matthews NCHS Data Brief* 2009 21:1-8). It is well known that pregnancy rates in women at 35 or more years of age are significantly lower, both naturally and with assisted reproduction. The decline in live birth rate reflects a decline in response to ovarian stimulation, reduced embryo quality and pregnancy rates, and an increased incidence of miscarriages and fetal aneuploidy. In addition, aging-associated chromosomal and meiotic spindle abnormalities in eggs are considered the major factors responsible for the increased incidence of infertility, fetal loss (miscarriage) and conceptions resulting in birth defects—most notably trisomy 21 or Down syndrome—in women at advanced reproductive ages (Henderson et al., *Nature* 1968 218:22-28, Hassold et al., *Hum Genet* 1985 70:11-17, Battaglia et al., *Hum Reprod* 1996 11:2217-2222, Hunt et al., *Trends Genet* 2008 24:86-93).

At present there is no known intervention to improve the pregnancy outcome of older female patients. In animal studies, chronic administration of pharmacologic doses of antioxidants during the juvenile period and throughout adult reproductive life has been reported to improve oocyte quality in aging female mice (Tarin et al., *Mol Reprod Dev* 2002 61:385-397). However, this approach has significant long-term negative effects on ovarian and uterine function, leading to higher fetal death and resorptions as well as decreased litter frequency and size in treated animals (Tarin et al., *Theriogenology* 2002 57:1539-1550). Thus, clinical translation of chronic anti-oxidant therapy for maintaining or improving oocyte quality in aging females is impractical.

Aging and age-related pathologies are frequently associated with loss of mitochondrial function, due to decreased mitochondrial numbers (biogenesis), diminished mitochondrial activity (production of ATP, which is the main source of energy for cells) and/or accumulation of mitochondrial DNA (mtDNA) mutations and deletions. As oocytes age and oocyte mitochondrial energy production decreases, many of the critical processes of oocyte maturation, required to produce a competent egg, especially nuclear spindle activity and chromosomal segregation, become impaired (Barttmann et al., *J Assist Reprod Genet* 2004 21:79-83, Wilding et al., *Zygote* 2005 13:317-23).

Heterologous transfer of cytoplasmic extracts from young donor oocytes (viz. obtained from different women) into the oocytes of older women with a history of reproductive failure, a procedure known as ooplasmic transplantation or ooplasmic transfer, demonstrated improved embryo development and delivery of live offspring. Unfortunately, however, the children born following this procedure exhibit mitochondrial heteroplasmy or the presence of mitochondria from two different sources (Cohen et al., *Mol Hum Reprod* 1998 4:269-80, Barritt et al., *Hum Reprod* 2001 16:513-6, Muggleton-Harris et al., *Nature* 1982 299:460-2, Harvey et al., *Curr Top Dev Biol* 2007 77:229-49. This is consistent with the fact that maternally-derived mitochondria present in the egg are used to "seed" the embryo with mitochondria, as paternally-derived mitochondria from the sperm are destroyed shortly after fertilization (Sutovsky et al., *Biol Reprod* 2000 63:5820590). Although the procedure involves transfer of cytoplasm and not purified or isolated mitochondria from the donor eggs, the presence of donor mitochondria in the transferred cytoplasm, confirmed by the passage of "foreign" mitochondria into the offspring, is believed to be the reason why heterologous ooplasmic transfer provides a fertility benefit. Irrespective, the health impact of induced mitochondrial heteroplasmy in these children is as yet unknown; however, it has been demonstrated that a mouse model of mitochondrial heteroplasmy produces a phenotype consistent with metabolic syndrome (Acton et al., *Biol Reprod* 2007 77: 569-76). Arguably, the most significant issue with heterologous ooplasmic transfer is tied to the fact that mitochondria also contain genetic material that is distinct from nuclear genes contributed by the biological mother. and biological father.

Accordingly, the children conceived following this procedure have three genetic parents (biological mother, biological father, egg donor), and thus represent an example of genetic manipulation of the human germline for the generation of embryos. Ooplasmic transplantation procedures that result in mitochondrial heteroplasmy are therefore now regulated and largely prohibited by the FDA. For details, see CBER 2002 Meeting Documents, Biological Response Modifiers Advisory Committee minutes from May 9, 2002, which are publicly available from the FDA and "Letter to Sponsors/Researchers—Human Cells Used in Therapy Involving the Transfer of Genetic Material By Means Other Than the Union of Gamete Nuclei", which is also publicly available from the FDA.

Although the use of autologous mitochondria from somatic cells would avoid mitochondrial heteroplasmy, the mitochondria of somatic cells also suffer from age-related loss of mitochondrial function, due to decreased mitochondrial numbers (biogenesis), diminished mitochondrial activity (production of ATP, which is the main source of energy for cells) and/or accumulation of mitochondrial mtDNA mutations and deletions. Therefore, for women of advanced maternal age, no significant benefit would have been expected from transferring mitochondria derived from autologous somatic cells into oocytes. Moreover, a variety of stem cells are known to possess low mitochondrial activity (Ramalho-Santos et al., *Hum Reprod Update.* 2009 (5):553-72) and, therefore, adult stem cells were not thought to be viable sources of high activity mitochondria.

SUMMARY OF THE INVENTION

The present invention is based, in part, upon the surprising discovery that the mammalian female germline stem cells or oogonial stem cells (OSCs), which are present in the somatic tissue of the ovary, contain mitochondria with the highest known ATP-generating capacity of all stem cell types evaluated, and containing mtDNA having a reduced amount of accumulated mutations, including, in some cases, non-detectable levels of a common mtDNA deletion known to accumulate with age in somatic cells.

In one aspect, the invention provides a composition comprising functional mitochondria isolated from an oogonial stem cell (OSC) or the progeny of an OSC.

In certain embodiments, more than 2 percent, 5 percent, 10 percent or 20 percent of the mitochondria are functional mitochondria. In a particular embodiment, the more than 2 percent of the mitochondria that are functional mitochondria is determined by the steps of:

(a) binding a fluorescent mitochondrial tracking probe to mitochondria in the composition; wherein the tracking probe is selected from the group consisting of a non-oxidation dependent probe, an accumulation dependent probe, or a reduced oxidative state probe;

(b) sorting the mitochondria based upon binding of the tracking probe; and (c) determining the percentage of functional mitochondria based on the percentage of mitochondria which bind the tracking probe.

In one embodiment, more than 5 percent of the mitochondria are functional mitochondria. In another embodiment, more than 10 percent of the mitochondria are functional mitochondria. In still another embodimjent, more than 20 percent of the mitochondria are functional mitochondria.

In one embodiment, at least 75 percent, 85 percent or 90 percent of the functional mitochondria in the composition are high ATP-generating capacity mitochondria.

In another embodiment, the OSC or progeny of an OSC is an isolated non-embryonic stem cell that is mitotically competent and expresses Vasa, Oct-4, Dazl, Stella, and a stage-specific embryonic antigen.

In yet another embodiment, the OSC is obtained from ovarian tissue, blood, or bone marrow.

In still another embodiment, wherein the OSC or the progeny of an OSC produces at least two-fold more ATP per fg mtDNA than an ovarian somatic cell. In a particular related embodiment, the ovarian somatic cell is autologous to the OSC or progeny of an OSC.

In one embodiment, the OSC or the progeny of an OSC produces at least three-fold more ATP per fg mtDNA than an ovarian somatic cell. In a particular related emobidment, the ovarian somatic cell is autologous to the OSC or progeny of an OSC.

In another embodiment, the OSC or the progeny of an OSC produces at least four-fold more ATP per fg mtDNA than an ovarian somatic cell. In a particular related embodiment, the ovarian somatic cell is autologous to the OSC or progeny of an OSC. In yet another embodiment, the OSC or the progeny of an OSC produces at least ten-fold more ATP per fg mtDNA than an ovarian somatic cell. In a particular related embodiment, the ovarian somatic cell is autologous to the OSC or progeny of an OSC.

In still another embodiment, the OSC or the progeny of an OSC produces at least two-fold more ATP per fg mtDNA than a mesenchymal stem cell. In a particular related embodiment, the mesenchymal stem cell is autologous to the OSC or progeny of an OSC.

In one embodiment, the OSC or the progeny of an OSC produces at least three-fold more ATP per fg mtDNA than a mesenchymal stem cell. In a particular related embodiment, the mesenchymal stem cell is autologous to the OSC or progeny of an OSC.

In another embodiment, the OSC or the progeny of an OSC produces at least four-fold more ATP per fg mtDNA than a mesenchymal stem cell. In a particular related embodiment, the mesenchymal stem cell is autologous to the OSC or progeny of an OSC.

In still another embodiment, the OSC or the progeny of an OSC produces at least ten-fold more ATP per fg mtDNA than a mesenchymal stem cell. In a particular realted embodiment, the mesenchymal stem cell is autologous to the OSC or progeny of an OSC.

In some embodiments, the OSC is an isolated non-embryonic stem cell that is mitotically competent and expresses Vasa, Oct-4, Dazl, Stella and optionally a stage-specific embryonic antigen (SSEA) (e.g., SSEA-1, -2, -3, and -4). The OSC can be obtained from ovarian tissue, or non-ovarian tissue/sources, such as, e.g., bone marrow or blood, e.g., peripheral and umbilical cord blood.

In other embodiments, the composition comprising OSC mitochondria, or mitochondria obtained from a progeny of an OSC, is the cytoplasm of the cells without a nucleus.

In yet other embodiments, the composition comprising OSC mitochondria or mitochondria obtained from the progeny of an OSC is a purified preparation. In certain embodiments, the purified preparation does not contain or is at least about 85%, 90%, 95% free of OSCs, OSC progeny and/or non-functional mitochondria.

In some embodiments, the composition comprises $1\times10^3$ to $5\times10^4$ mitochondria.

In other embodiments, the OSC or progeny of an OSC produces at least 5-fold more ATP per fg mtDNA than an ovarian somatic cell or mesenchymal stem cell. In certain embodiments, the ovarian somatic cell or mesenchymal stem cell is autologous.

In yet other embodiments, the OSC or progeny of an OSC produces at least 10-fold more ATP per fg mtDNA than an ovarian somatic cell or mesenchymal stem cell. In certain embodiments, the ovarian somatic cell or mesenchymal stem cell is autologous.

In still other embodiments, the OSC or progeny of an OSC produces at least 50-fold more ATP per fg mtDNA than an ovarian somatic cell or mesenchymal stem cell. In certain, embodiments, the ovarian somatic cell or mesenchymal stem cell is autologous. In other embodiments, the OSC or progeny of an OSC produces at least 100-fold more ATP per fg mtDNA than an ovarian somatic cell or mesenchymal stem cell. In certain embodiments, the ovarian somatic cell or mesenchymal stem cell is autologous.

In some embodiments, the oocyte is obtained from a human female of advanced maternal age. In other embodiments, the oocyte is obtained from a human female with low ovarian reserve.

In some embodiments, the composition comprises mitochondria that have been isolated by centrifugation. In other embodiments, the composition comprises mitochondria that have been isolated by mitochondrial membrane potential-dependent cell sorting.

In some embodiments, the composition comprising mitochondria obtained from at least one OSC or at least one progeny of an OSC, is the cytoplasm of the cells without a nucleus. In other embodiments, the composition comprising mitochondria obtained from at least one OSC or at least one progeny of an OSC is a purified preparation of mitochondria.

In another aspect, the invention provides an composition comprising isolated OSC mitochondria, or mitochondria obtained from a progeny of an OSC.

In some embodiments, the composition is at least about 85%, 90%, 95% free of cells or non-functional mitochondria.

In some embodiments, the composition comprises $1 \times 10^3$ to $5 \times 10^4$ mitochondria.

In other embodiments, the OSC or progeny of an OSC produces at least 5-fold more ATP per fg mtDNA than an ovarian somatic cell or mesenchymal stem cell. In certain embodiments, the ovarian somatic cell or mesenchymal stem cell is autologous.

In some embodiments, the OSC or progeny of an OSC produces at least 10-fold more ATP per fg mtDNA than an ovarian somatic cell or mesenchymal stem cell. In certain embodiments, the ovarian somatic cell or mesenchymal stem cell is autologous.

In other embodiments, the OSC or progeny of an OSC produces at least 50-fold more ATP per fg mtDNA than an ovarian somatic cell or mesenchymal stem cell. In certain embodiments, the ovarian somatic cell or mesenchymal stem cell is autologous.

In some embodiments, the OSC or progeny of an OSC produces at least 100-fold more ATP per fg mtDNA than an ovarian somatic cell or mesenchymal stem cell. In certain embodiments, the ovarian somatic cell or mesenchymal stem cell is autologous.

In some embodiments, the OSC or progeny of an OSC is obtained from a human female of advanced maternal age. In other embodiments, the OSC or progeny of an OSC is obtained from a human female with low ovarian reserve.

In some embodiments, the composition comprises mitochondria that have been isolated by centrifugation. In other embodiments, the composition comprises mitochondria that have been isolated by mitochondrial membrane potential-dependent cell sorting.

In yet another aspect, the invention provides a composition comprising at least one isolated mitochondrion obtained from an OSC or at least one progeny of an OSC.

In some embodiments, the composition comprises $1 \times 10^3$ to $5 \times 10^4$ mitochondria.

In other embodiments, the OSC or progeny of an OSC produces at least 5-fold more ATP per fg mtDNA than an ovarian somatic cell or mesenchymal stem cell. In certain embodiments, the ovarian somatic cell or mesenchymal stem cell is autologous.

In some embodiments, the OSC or progeny of an OSC produces at least 10-fold more ATP per fg mtDNA than an ovarian somatic cell or mesenchymal stem cell. In certain embodiments, the ovarian somatic cell or mesenchymal stem cell is autologous.

In other embodiments, the OSC or progeny of an OSC produces at least 50-fold more ATP per fg mtDNA than an ovarian somatic cell or mesenchymal stem cell. In certain embodiments, the ovarian somatic cell or mesenchymal stem cell is autologous.

In some embodiments, the OSC or progeny of an OSC produces at least 100-fold more ATP per fg mtDNA than an ovarian somatic cell or mesenchymal stem cell. In certain embodiments, the ovarian somatic cell or mesenchymal stem cell is autologous.

In some embodiments, the OSC or progeny of an OSC is obtained from a human female of advanced maternal age. In other embodiments, the OSC or progeny of an OSC is obtained from a human female with low ovarian reserve.

In some embodiments, the composition comprises mitochondria that have been isolated by centrifugation. In other embodiments, the composition comprises mitochondria that have been isolated by mitochondrial membrane potential-dependent cell sorting.

In another aspect, the invention provides an oocyte prepared in accordance with any of the methods described above.

In yet another aspect, the invention provides an oocyte comprising exogenous, autologous OSC mitochondria or mitochondria obtained from a progeny of an OSC.

In yet another aspect, the invention provides a method of in vitro fertilization. The method comprises the steps of: a) obtaining a composition comprising i) mitochondria obtained from an OSC, or ii) mitochondria obtained from a progeny of an OSC; b) transferring the composition into an isolated, autologous oocyte; and c) fertilizing the autologous oocyte in vitro to form a zygote. In an embodiment, the method further comprises transferring the zygote, or a preimplantation stage embryo derived from the zygote, into the uterus or oviduct of a female subject.

In some embodiments, the composition comprises $1 \times 10^3$ to $5 \times 10^4$ mitochondria.

In other embodiments, the OSC or progeny of an OSC produces at least 5-fold more ATP per fg mtDNA than an ovarian somatic cell or mesenchymal stem cell. In certain embodiments, the ovarian somatic cell or mesenchymal stem cell is autologous.

In yet other embodiments, the OSC or progeny of an OSC produces at least 10-fold more ATP per fg mtDNA than an ovarian somatic cell or mesenchymal stem cell. In certain embodiments, the ovarian somatic cell or mesenchymal stem cell is autologous.

In still other embodiments, the OSC or progeny of an OSC produces at least 50-fold more ATP per fg mtDNA than an ovarian somatic cell or mesenchymal stem cell. In certain, embodiments, the ovarian somatic cell or mesenchymal stem cell is autologous.

In other embodiments, the OSC or progeny of an OSC produces at least 100-fold more ATP per fg mtDNA than an ovarian somatic cell or mesenchymal stem cell. In certain embodiments, the ovarian somatic cell or mesenchymal stem cell is autologous.

In some embodiments, the oocyte is obtained from a human female of advanced maternal age. In other embodiments, the oocyte is obtained from a human female with low ovarian reserve.

In some embodiments, the composition comprises mitochondria that have been isolated by centrifugation. In other embodiments, the composition comprises mitochondria that have been isolated by mitochondrial membrane potential-dependent cell sorting.

In some embodiments, the at least one OSC is obtained from ovarian tissue. In other embodiments, the at least one OSC is obtained from a non-ovarian tissue.

In some embodiments, the non-ovarian tissue is blood. In other embodiments, the non-ovarian tissue is bone marrow.

In some embodiments, the composition comprising mitochondria obtained from at least one OSC or at least one progeny of an OSC, is the cytoplasm of the cells without a nucleus. In other embodiments, the composition comprising mitochondria obtained from at least one OSC or at least one progeny of an OSC is a purified preparation of mitochondria.

In yet another aspect, the invention provides a method of isolating a population of functional mitochondria from at least one OSC, or at least one progeny of an OSC. The method comprises the steps of incubating a composition comprising at least one OSC, or at least one progeny of an OSC, with a mitochondrial tracking probe under conditions sufficient to bind the probe to the functional mitochondria and sorting the functional mitochondria from the non-functional mitochondria, thereby isolating the population of functional mitochondria from at least one OSC, or at least one progeny of an OSC. In some embodiments, non-functional mitochondria are excluded from the population of functional mitochondria.

In some embodiments, the mitochondrial tracking probe is a non-oxidation dependent probe. In some embodiments, the mitochondrial tracking probe is an accumulation dependent probe. In some embodiments, the mitochondrial tracking probe is a reduced oxidative state probe. In some embodiments, the sorting step includes fluorescence-activated cell sorting.

In yet another aspect, the invention provides a method of identifying a population of functional mitochondria obtained from at least one OSC, or at least one progeny of an OSC. The method comprises the steps of: a) incubating a composition comprising at least one OSC, or at least one progeny of an OSC, with a fluorescent reduced oxidative state probe and a fluorescent accumulation dependent probe under conditions sufficient to bind the fluorescent reduced oxidative state probe to functional mitochondria in the composition and bind the fluorescent accumulation dependent probe to total mitochondria in the composition; b) obtaining a composition comprising the functional mitochondria using fluorescence-activated cell sorting, wherein the composition excludes non-functional mitochondria; c) determining the amount of functional mitochondria and the amount of total mitochondria; and d) calculating the ratio of functional mitochondria to total mitochondria; and e) determining whether the ratio is greater than about 0.02, thereby identifying a population of functional mitochondria obtained from at least one OSC, or at least one progeny of an OSC.

In some embodiments, the fluorescent accumulation dependent probe can fluoresce in one portion of the spectrum (e.g., green). In other embodiments, the fluorescent reduced oxidative state probe can fluoresce in a different portion of the spectrum (e.g., red).

In another aspect, the invention provides a composition comprising functional mitochondria obtained according to a method comprising the steps of: a) incubating a composition comprising at least one OSC, or at least one progeny of an OSC, with a fluorescent reduced oxidative state probe and a fluorescent accumulation dependent probe under conditions sufficient to bind the fluorescent reduced oxidative state probe to functional mitochondria in the composition and bind the fluorescent accumulation dependent probe to total mitochondria in the composition; and b) obtaining a composition comprising the functional mitochondria using fluorescence-activated cell sorting, wherein the composition excludes non-functional mitochondria.

Another aspect of the invention provides a kit comprising a composition comprising isolated OSC mitochondria or mitochondria obtained from a progeny of an OSC and instructions for use. In one embodiment, the composition is at least about 85%, 90%, 95% free of cells or non-functional mitochondria.

Yet another aspect of the invention provides a kit comprising at least one isolated mitochondrion obtained from an OSC or at least one progeny of an OSC and instructions for use.

Another aspect of the invention provides a method for increasing the ATP-generating capacity of an oocyte. The method comprises the steps of: a) obtaining a composition comprising mitochondria obtained from at least one OSC or at least one progeny of an OSC that is autologous to the oocyte; and b) injecting the composition of mitochondria into the oocyte.

In some embodiments, the composition comprises $1 \times 10^3$ to $5 \times 10^4$ mitochondria.

In other embodiments, the OSC or progeny of an OSC produces at least 5-fold more ATP per fg mtDNA than an ovarian somatic cell or mesenchymal stem cell. In certain embodiments, the ovarian somatic cell or mesenchymal stem cell is autologous.

In yet other embodiments, the OSC or progeny of an OSC produces at least 10-fold more ATP per fg mtDNA than an ovarian somatic cell or mesenchymal stem cell. In certain embodiments, the ovarian somatic cell or mesenchymal stem cell is autologous.

In still other embodiments, the OSC or progeny of an OSC produces at least 50-fold more ATP per fg mtDNA than an ovarian somatic cell or mesenchymal stem cell. In certain, embodiments, the ovarian somatic cell or mesenchymal stem cell is autologous.

In other embodiments, the OSC or progeny of an OSC produces at least 100-fold more ATP per fg mtDNA than an ovarian somatic cell or mesenchymal stem cell. In certain embodiments, the ovarian somatic cell or mesenchymal stem cell is autologous.

In some embodiments, the oocyte is obtained from a human female of advanced maternal age. In other embodiments, the oocyte is obtained from a human female with low ovarian reserve.

In some embodiments, the composition comprises mitochondria that have been isolated by centrifugation. In other embodiments, the composition comprises mitochondria that have been isolated by mitochondrial membrane potential-dependent cell sorting.

In some embodiments, the at least one OSC is obtained from ovarian tissue. In other embodiments, the at least one OSC is obtained from a non-ovarian tissue.

In some embodiments, the non-ovarian tissue is blood. In other embodiments, the non-ovarian tissue is bone marrow.

In some embodiments, the composition comprising mitochondria obtained from at least one OSC or at least one progeny of an OSC, is the cytoplasm of the cells without a nucleus. In other embodiments, the composition comprising mitochondria obtained from at least one OSC or at least one progeny of an OSC is a purified preparation of mitochondria.

In another aspect, the invention provides an oocyte prepared by a method comprising the steps of: a) obtaining a composition comprising mitochondria obtained from at least one OSC or at least one progeny of an OSC that is autologous to the oocyte; and b) injecting the composition of mitochondria into the oocyte.

Yet another aspect of the invention provides a composition of mitochondria obtained from at least one OSC or at least one progeny of an OSC, wherein the composition comprises a population of mitochondria in which greater than about 75%, 85%, 90%, or about 99% of the mitochondria are high ATP-generating capacity mitochondria.

In still another aspect, the invention provides compositions comprising a population of mitochondria in which less than about 5% to about 25% of the mtDNA comprises a deletion mutation within nucleotides 8470-13447 of the mitochondrial genome, and methods pertaining to such compositions.

Other features and advantages of the invention will be apparent from the detailed description, and from the claims. Thus, other aspects of the invention are described in the following disclosure and are within the ambit of the invention.

BRIEF DESCRIPTION OF THE DRAWINGS

The following Detailed Description, given by way of example, but not intended to limit the invention to specific embodiments described, may be understood in conjunction with the accompanying figures, incorporated herein by reference.

FIG. 1 depicts validation of a fluorescence-activated cell sorting (FACS)-based protocol for OSC isolation.

FIG. 3 depicts isolation of VASA-positive cells from adult mouse and human ovaries using FACS. In FIG. 3a and b, the representative histological appearance of adult ovarian tissue used for human (a) and mouse (b) OSC isolation is shown. Scale bars, 100 μm. In FIGS. 3c and d, the morphology of viable cells isolated by FACS based on cell-surface expression of VASA is shown. Scale bars, 10 μm. FIG. 3e provides the gene expression profile of starting ovarian material and freshly-isolated OSCs, showing assessment of 3 different patients as examples for human tissue analysis (No RT: PCR of RNA sample without reverse transcription; β-actin, sample loading control).

FIG. 4 depicts functional eggs obtained from mouse OSCs after intraovarian transplantation. In FIGS. 4a and 4b, examples of growing follicles containing GFP-negative and GFP-positive (hematoxylin counterstain) oocytes are shown in ovaries of wild-type mice injected with GFP-expressing OSCs 5-6 months earlier.

FIG. 6 depicts evaluation of mouse and human ovary-derived VASA-positive cells in defined cultures. FIGS. 6a through 6d show assessment of OSC proliferation by dual detection of VASA expression and BrdU incorporation in mouse (6a, 6b) and human (6c, 6d) OSCs maintained in MEF-free cultures. FIG. 6e shows the typical growth curve for MEF-free cultures of mouse OSCs after passage and seeding $2.5 \times 10^4$ cells per well in 24-well culture plates. FIG. 6f shows FACS analysis using the COOH antibody to detect cell-surface expression of VASA in mouse OSCs after months of propagation (example shown, passage 45).

FIG. 7 depicts spontaneous oogenesis from cultured mouse and human OSCs. FIG. 7*d* indicates the number of immature oocytes formed by mouse OSCs 24, 48 and 72 hours after passage and seeding $2.5 \times 10^4$ cells per well in 24-well culture plates (culture supernatants were collected at each time point for determination, and thus the values represent numbers generated over each 24 hour block, not cumulative numbers; mean±SEM, n=3 independent cultures). FIGS. 7*e* through 7*g* show in vitro oogenesis from human OSCs, with examples of immature oocytes formed by human OSCs in culture (7*f*, morphology; 7*g*, expression of oocyte marker proteins VASA, KIT, MSY2 and LHX8) and numbers formed following passage and seeding of $2.5 \times 10^4$ cells per well in 24-well culture plates (7*e*; mean±SEM, n=3 independent cultures) shown. The presence of mRNAs encoding oocyte marker genes (Vasa, Kit, Msy2, Nobox, Lhx8, Gdf9, Zp1, Zp2, Zp3) in human OSC-derived oocytes is shown in panel c along with results for mouse OSC-derived oocytes. Scale bars, 25 µm.

FIG. 9 depicts ploidy analysis of human fibroblasts and mouse OSCs in culture.

FIG. 10 depicts generation of oocytes from human OSCs in human ovary tissue. Direct (live-cell) GFP fluorescence analysis of human ovarian cortical tissue following dispersion, re-aggregation with GFP-hOSCs (10*a*) and in vitro culture for 24-72 hours (10*b*, 10*c*) is shown. Note the formation of large single GFP-positive cells surrounded by smaller GFP-negative cells in compact structures resembling follicles (FIGS. 10*b* and 10*c*; scale bars, 50 µm). Examples of immature follicles containing GFP-positive oocytes (highlighted by black arrowheads, against a hematoxylin counterstain) in adult human ovarian cortical tissue injected with GFP-hOSCs and xenografted into NOD/SCID female mice are shown (FIG. 10*d*, 1 week post-transplant; FIG. 10*f*, 2 weeks post-transplant). Note comparable follicles with GFP-negative oocytes in the same grafts. As negative controls, all immature follicles in human ovarian cortical tissue prior to GFP-hOSC injection and xenografting (10*e*) or that received vehicle injection (no GFP-hOSCs) prior to xenografting (10*g*) contained GFP-negative oocytes after processing for GFP detection in parallel with the samples shown above.

FIG. 12 depicts cryopreservation and thawing of human ovarian cortical tissue and freshly-isolated human OSCs.

DETAILED DESCRIPTION OF THE INVENTION

Definitions

Figure 1A:
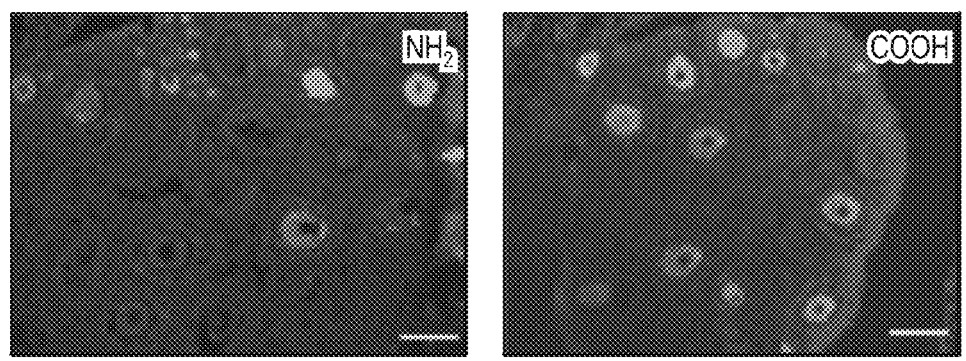
In FIG. 1a, immunofluorescence analysis of VASA expression (with DAPI counterstain) is shown in adult mouse ovaries using antibodies against the $NH_2$ or COOH terminus of VASA (scale bars, 50 μm).

Unless otherwise defined, all technical and scientific terms used herein have the same meaning as commonly understood by one of ordinary skill in the art to which this invention belongs. In case of conflict, the present application, including definitions will control.

"Oogonial stem cells" (OSCs), also known as female germline stem cells, are derived from postnatal sources and express markers including Vasa, Oct-4, Dazl, Stella and optionally an SSEA. OSCs are mitotically competent (i.e., capable of mitosis) and do not express oocyte markers including growth/differentiation factor-9 ("GDF-9"), and zona pellucida glycoproteins (e.g., zona pellucida glycoprotein-3, "ZP3"), or markers of meiotic recombination such as synaptonemal complex protein-3 ("SYCP3" or "SCP3"). OSCs can be obtained from the postnatal ovary. OSCs are known in the art and are described in U.S. Pat. No. 7,955,846, the entire contents of which are incorporated herein by reference. OSCs are additionally described by Johnson et al., Nature 428:145-150; Johnson et al., Cell 2005 122:303-315; Wang et al., Cell Cycle 2010 9:339-349; Niikura et al., Aging 2010 2:999-1003; Tilly et al., Biol Reprod 2009 80:2-12, Tilly et al., Mol Hum Reprod 2009 15:393-398; Zou et al., Nat Cell Biol 2009 11:631-636; Pacchiarotti et al., Differentiation 2010 79:159-170), the contents of which are incorporated herein by reference. Preferably, the OSC of the invention is a human OSC.

As used herein, the "progeny of an OSC" refers to all daughter cells derived from OSCs of the invention, including progenitor cells and differentiated cells that maintain or achieve oogenic potential (i.e., the ability to form an oocyte) and functional mitochondria. Preferably, the OSC progeny of the invention is a human OSC progeny.

As used herein, the term, "functional mitochondria" refers to mitochondria that produce ATP and can be used interchangeably with the term "respiring mitochondria."

OSCs may additionally be obtained from the bone marrow, peripheral blood or umbilical cord blood. Bone marrow derived OSCs of the invention can also circulate throughout the body and most preferably can be localized in bone marrow, peripheral blood and ovary. Bone marrow derived OSCs express markers including Oct 4, Vasa, Dazl, Stella, Fragilis, and optionally Nobox, Kit and Sca-1. Bone marrow derived OSCs are mitotically competent (i.e., capable of mitosis) and do not express GDF-9, zona pellucida proteins (e.g., ZP3) or SCP3. For additional details on bone marrow-derived OSCs, see, U.S. Patent Pub. No. 20060010509, the entire contents of which are incorporated herein by reference for their description of OSCs in the bone marrow. For additional details on peripheral blood and umbilical cord blood derived OSCs, see, U.S. Patent Pub. No. 20060015961, the entire contents of which are incorporated herein by reference for their description of OSCs in the peripheral blood.

Oct-4, also referred to as POU domain class 5 transcription factor 1 or PouSf1, is a gene expressed in female germline stem cells and their progenitor cells. The Oct-4 gene encodes a transcription factor that is involved in the establishment of the mammalian gee nline and plays a significant role in early germ cell specification (reviewed in Scholer, Trends Genet. 1991 7(10):323-329). In the developing mammalian embryo, Oct-4 is down-regulated during the differentiation of the epiblast, eventually becoming confined to the germ cell lineage. In the germline, Oct-4 expression is regulated separately from epiblast expression. Expression of Oct-4 is a phenotypic marker of totipotency (Yeom et al., Development 1996 122: 881-888).

Stella, also commonly referred to as developmental pluripotency associated 3 or Dppa3, is a gene expressed in female germline stem cells and their progenitor cells. Stella is a novel gene specifically expressed in primordial germ cells and their descendants, including oocytes (Bortvin et al., BMC Developmental Biology 2004 4(2):1-5). Stella encodes a protein with a SAP-like domain and a splicing factor motif-like structure. Embryos deficient in Stella expression are compromised in preimplantation development and rarely reach the blastocyst stage. Thus, Stella is a maternal factor implicated in early embryogenesis.

Dazl is a gene expressed in female germline stem cells and their progenitor cells. The autosomal gene Dazl is a member of a family of genes that contain a consensus RNA binding domain and are expressed in gel in cells. Loss of expression of an intact Dazl protein in mice is associated with failure of germ cells to complete meiotic prophase. Specifically, in female mice null for Dazl, loss of germ cells occurs during fetal life at a time coincident with progression of germ cells through meiotic prophase. In male mice null for Dazl, genii cells were unable to progress beyond the leptotene stage of meiotic prophase I. Thus, in the absence of Dazl, progression through meiotic prophase is interrupted (Saunders et al., Reproduction 2003 126:589-597).

Vasa, also referred to as DEAD box polypeptide 4 or Ddx4, is a gene expressed in female germline stem cells and their progenitor cells. Vasa is a component of the germplasm that encodes a DEAD-family ATP-dependent RNA helicase (Liang et al., Development 1994 120:1201-1211; Lasko et al., Nature 1988 335:611-167). The molecular function of Vasa is directed to binding target mRNAs involved in germ cell establishment (e.g., Oskar and Nanos), oogenesis, (e.g., Gruken), and translation onset (Gavis et al., Development 1996 110: 521-528). Vasa is required for pole cell formation and is exclusively restricted to the germ cell lineage throughout development. Thus, Vasa is a molecular marker for the germ cell lineage in most animal species (Toshialci et al., Cell Structure and Function 2001 26:131-136).

Stage-Specific Embryonic Antigens are optionally expressed in female germline stem cells and expressed in female germline stem cell progenitors of the invention. Stage-Specific Embryonic Antigen-1 (SSEA-1) is a cell surface embryonic antigen whose functions are associated with cell adhesion, migration and differentiation. During hypoblast formation, SSEA-1 positive cells can be identified in the blastocoel and hypoblast and later in the germinal crescent. SSEA-1 functions in the early germ cell and neural cell development. (D'Costa et al., Int J. Dev. Biol. 1999 43(4):349-356; Henderson et al., Stem Cells 2002 20:329-337). In specific embodiments, expression of SSEAs in female germline stem cells may arise as the cells differentiate. SSEAs useful in the invention include SSEA-1, -2, -3, and -4.

The term "autologous" as used herein refers to biological compositions obtained from the same subject. In one embodiment, the biological composition includes OSCs, OSC-derived compositions and oocytes (i.e., mature oocytes). Accordingly, in conducting methods of the invention, the female germ cell cytoplasm or mitochondria used for transfer and the recipient oocyte into which the aforementioned compositions are transferred are obtained from the same subject.

The term "isolated" as used herein refers to an OSC, mitochondrion or composition derived from an OSC (e.g., cytoplasm, mitochondrial preparation), which has been physically separated or removed from its natural biological environment. An isolated OSC, mitochondrion or composition need not be purified.

The term "exogenous" as used herein refers to transferred cellular material (e.g., mitochondria) that is removed from one cell and transferred into another cell. For example, OSC derived mitochondria that have been transferred into an oocyte, even if both are derived from the same subject, would be exogenous.

A "subject" is any live-bearing member of the class mammalia, including humans, domestic and farm animals, and zoo, sports or pet animals, such as mouse, rabbit, pig, sheep, goat, cattle and higher primates.

As used herein, the term "advanced maternal age" as it relates to humans refers to a woman who is 34 years of age or older. As used herein, the term "oocyte-related infertility" as it relates to humans refers to an inability to conceive after one year of unprotected intercourse which is not caused by an anatomical abnormality (e.g., blocked oviduct) or pathological condition (e.g., uterine fibroids, severe endometriosis, Type II diabetes, polycystic ovarian disease).

As used herein, the term "low ovarian reserve" as it relates to humans refers to a woman who exhibits a circulating Follicle Stimulating Hormone (FSH) level greater than 15 miu/ml in a "day 3 FSH test," as described in Scott et al., *Fertility and Sterility*, 1989 51:651-4, or a circulating Anti-Mullerian Hormone (AMH) level less than 0.6 ng/ml, or an antral follicle count less than 7 as measured by ultrasound.

In this disclosure, "comprises," "comprising," "containing" and "having" and the like can have the meaning ascribed to them in U.S. Patent law and can mean "includes," "including" and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "reduced" or "reduce" or "decrease" as used herein generally means a decrease of at least 5%, for example a decrease by at least about 10%, or at least about 20%, or at least about 30%, or at least about 40%, or at least about 50%, or at least about 60%, or at least about 70%, or at least about 80%, or at least about 90% or up to and including a 100% decrease (i.e. substantially absent or below levels of detection), or any decrease between 5-100% as compared to a reference level, as that teen is defined herein, and as determined by a method that achieves statistical significance ($p<0.05$).

The term "increase" as used herein generally means an increase of at least 5%, for example an increase by at least about 10%, or at least about 20%, or at least about 30%, or at least about 40%, or at least about 50%, or at least about 60%, or at least about 70%, or at least about 80%, or at least about 90% or up to and including a 100% increase (i.e. substantially above levels of detection), or any increase between 5-100% as compared to a reference level, as that term is defined herein, and as determined by a method that achieves statistical significance ($p<0.05$).

As used herein "an increase in ATP generation or production" refers to an amount of ATP production that is at least about 1-fold more than (for example 1, 2, 3, 4, 5, 6, 7, 8, 9, 10, 20, 30, 40, 50, 60, 70, 80, 90, 100, 1000, 10,000-fold or more) the amount of ATP production in a reference level, as that teml is defined herein. ATP production can be measured by standard methods known in the art.

As used herein, "high ATP-generating capacity mitochondria" refers to mitochondria having a high mitochondrial membrane potential, as determined by a probe which can distinguish between high and low (or between high and medium/low) membrane potential. One method of identifying mitochondria with high mitochondrial membrane potential is the use of the fluorescent probe 5,5',6,6'-tetrachloro-1, 1',3,3'-tetraethylbenzimidazolyl carbocyanine iodide (JC-1, Invitrogen T3168, Life Technologies Corp., Carlsbad, Calif.), which fluoresces red-orange (590 nm) in high quality mitochondria but fluoresces green (510-520 nm) in medium and/or low quality mitochondria. (See, e.g., Garner et al., *Bio. Reprod.* 1997 57:1401-1406; Reers et al., *Biochemistry* 1991 30:4480-4486; Cossariza et al, *Biochem Biophys Res Commun* 1993 197:40-45; Smiley et al., *Proc Natl Acad Sci USA* 1991 88:3671-3675).

As used herein, the tem). "standard" or "reference" refers to a measured biological parameter including but not limited to defects such as aneuploidy, mutation, chromosomal misalignment, meiotic spindle abnormalities, and/or mitochondrial dysfunction (aggregation, impaired ATP production), or the reduction or elimination of such defects, in a known sample against which another sample is compared; alternatively, a standard can simply be a reference number that represents an amount of the measured biological parameter that defines a baseline for comparison. The reference number can be derived from either a sample taken from an individual, or a plurality of individuals or cells obtained therefrom (e.g., oocytes, OSCs). That is, the "standard" does not need to be a sample that is tested, but can be an accepted reference number or value. A series of standards can be developed that take into account an individual's status, e.g., with respect to age, gender, weight, height, ethnic background etc. A standard level can be obtained for example from a known sample from a different individual (e.g., not the individual being tested). A known sample can also be obtained by pooling samples from a plurality of individuals (or cells obtained therefrom) to produce a standard over an averaged population. Additionally, a standard can be synthesized such that a series of standards are used to quantify the biological parameter in an individual's sample. A sample from the individual to be tested can be obtained at an earlier time point (presumably prior to the onset of treatment) and serve as a standard or reference compared to a sample taken from the same individual after the onset of treatment. In such instances, the standard can provide a measure of the efficacy of treatment. In specific embodiments, a "standard" or "reference" is an ovarian somatic cell (e.g., an aged-matched ovarian somatic cell obtained from a female subject having a functional reproductive system) or an aged-matched mesenchymal stem cell.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Other definitions appear in context throughout this disclosure.

Compositions and Methods of the Invention

Isolation of OSCs

Adult ovarian cortical tissue can be obtained using a minor laparoscopic procedure known in the art to collect a small (e.g., 3×3×1 mm) ovarian cortical biopsy, which is then processed for OSC isolation. See Gook et al., *Human Reproduction*, 2004 20(1):72-78.

Figure 17:
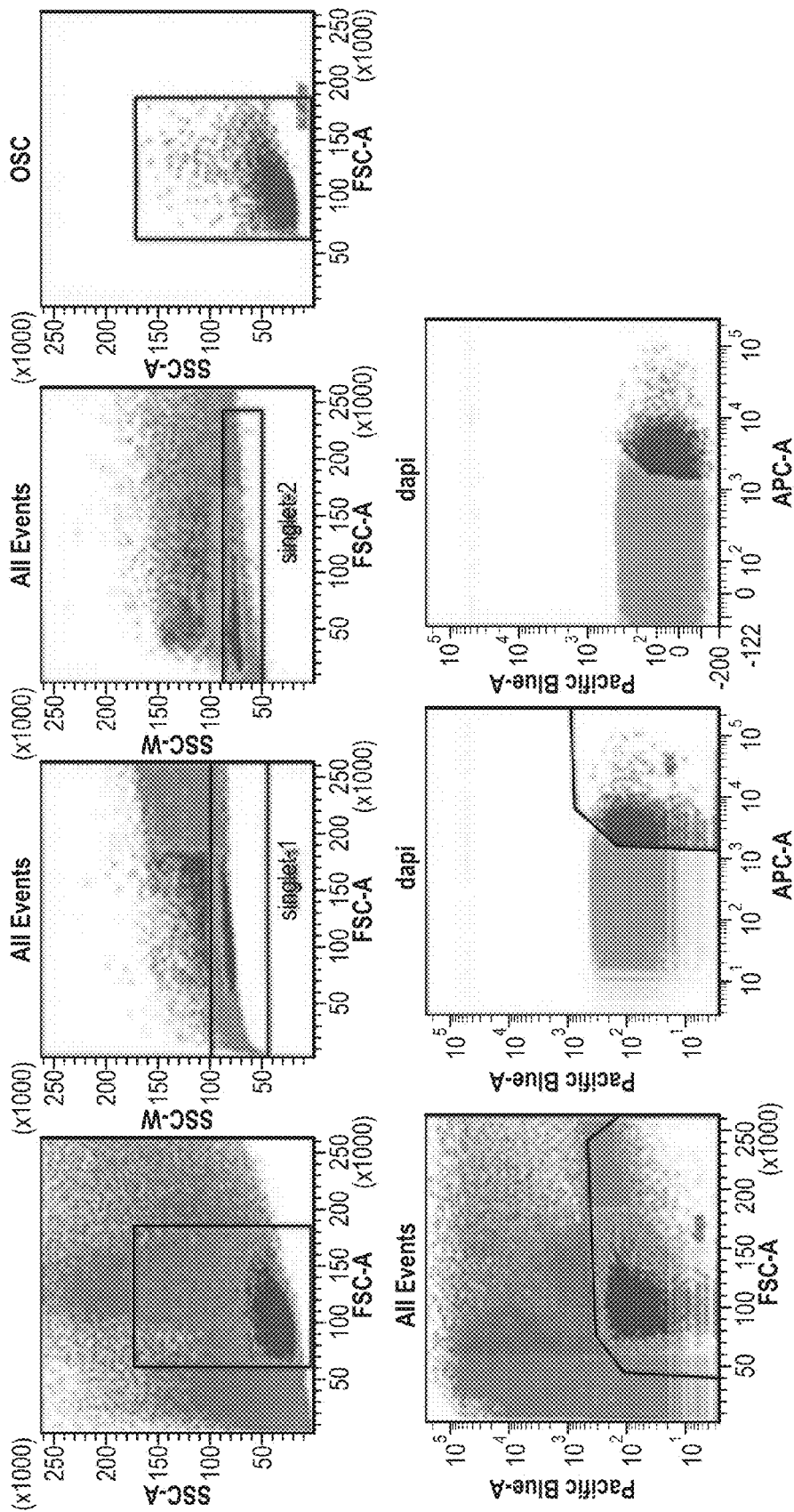
FIG. 17 depicts FACS—based germ cell purification or isolation from bone marrow preparations of adult female mice during estrus of the female reproductive cycle using cell surface expression of Vasa to isolate the cells.
Figure 17:
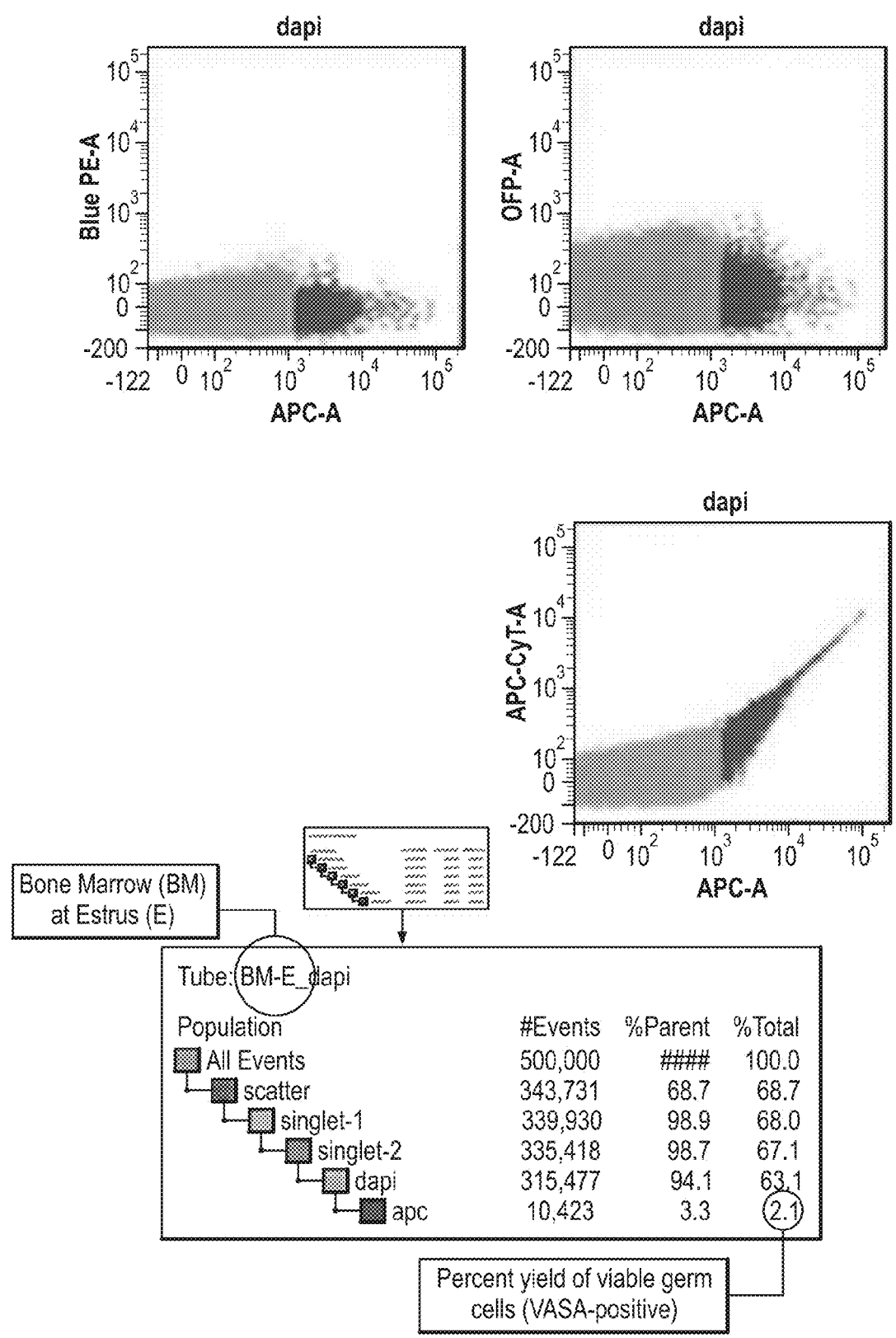
Figure 18:
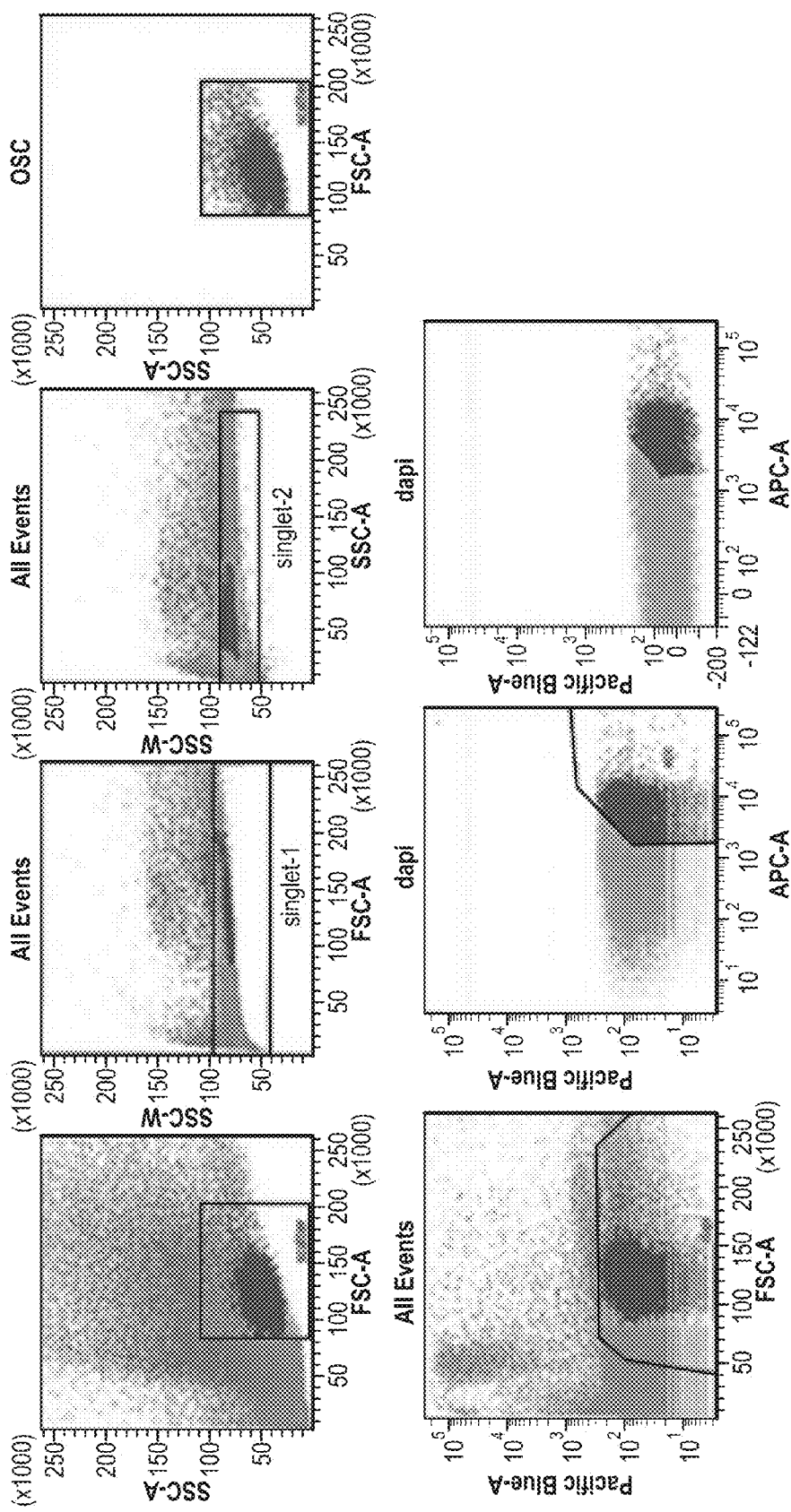
FIG. 18 depicts FACS—based germ cell purification or isolation from peripheral blood preparations of adult female mice during estrus of the female reproductive cycle using cell surface expression of Vasa to isolate the cells.
Figure 18:
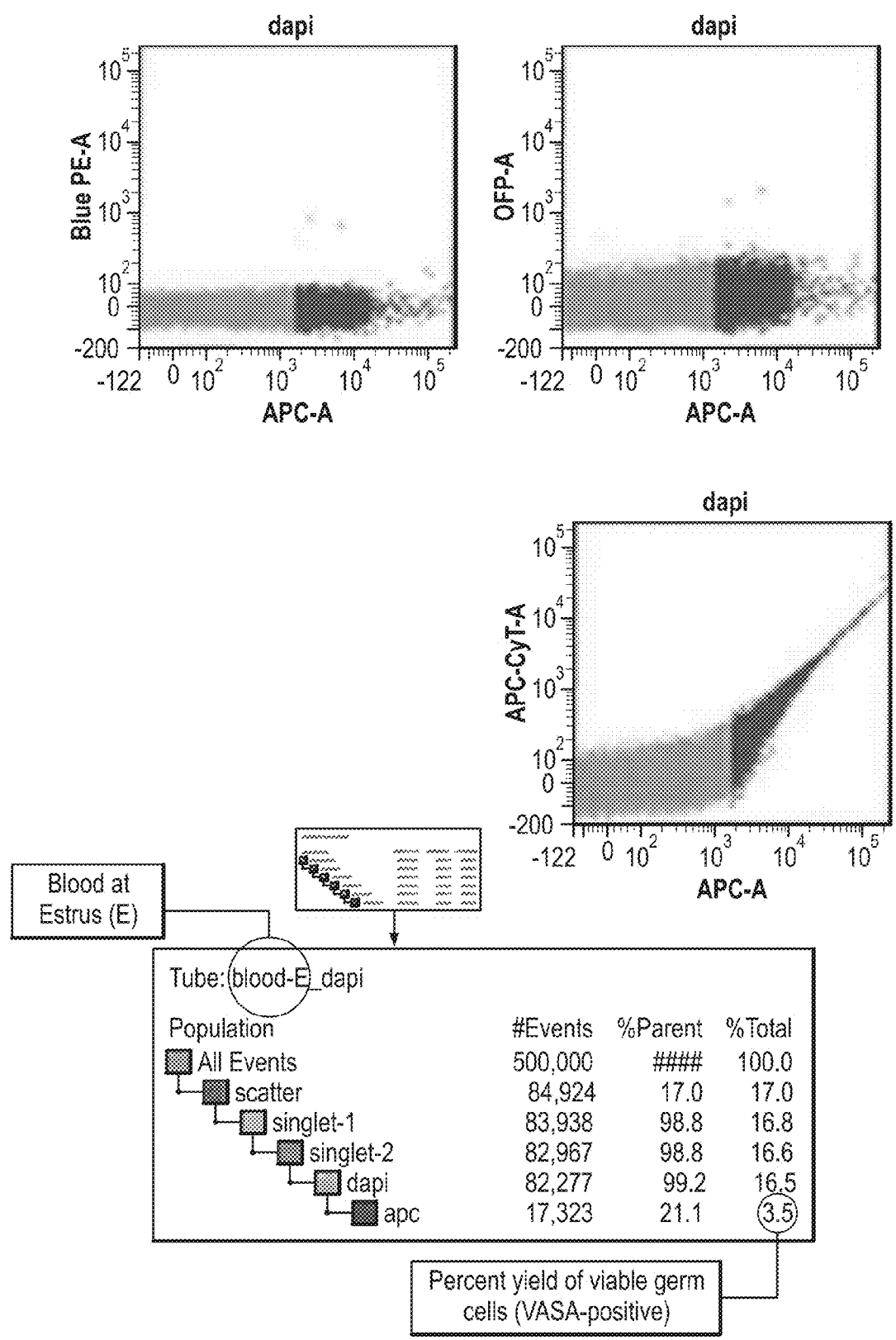

Isolation of human OSCs from adult ovarian cortical tissue can be performed as described in Example 1, FIG. 1 or as previously described in the art, or using comparable techniques. See, for example, paragraph 0116 of U.S. Patent Pub. No. 20060010508, and Zou et al., *Nature Cell Biology* 2009 5:631-6. Epub 2009 Apr. 12. OSCs can also be obtained from non-ovarian sources, such as bone marrow or peripheral blood. Bone marrow and peripheral blood derived OSCs can be isolated by standard means known in the art for the separation of stem cells from, for example, the marrow or blood (e.g., cell sorting). Optionally, the isolation protocol includes generation of a kit+/lin− fraction that is depleted of hematopoietic cells. Additional selection means based on the characteristic profile of gene expression in OSCs (e.g., Vasa, Oct-4, Dazl, Stella, Fragilis) can be employed to further purify or isolate the desired population of cells and to reduce or eliminate other cells and material from the biological sample from which they were obtained (e.g. bone marrow, peripheral blood). For example, the methods described in Example 1, FIG. 1b have been applied to a mononuclear fraction of blood cells and bone marrow cells to obtain purified or isolated OSCs from non-ovarian sources. Briefly, cells were incubated with a rabbit anti-VASA antibody (ab13840; Abcam, Cambridge, Mass.) for 20 minutes, washed, and incubated with goat anti-rabbit IgG conjugated to allophcocyanin (APC) for 20 minutes, and washed again. Labeled cells in the eluate were isolated by fluorescence-activated cell sorting (FACS) using a BD Biosciences FACSAria II cytometer (Harvard Stem Cell Institute, Boston, Mass.), gated against negative (unstained and no primary antibody) controls. Propidium iodide was added to the cell suspension just prior to sorting for dead cell exclusion. Results obtained using cell surface expression of Vasa to isolate OSCs from non-ovarian sources are provided in FIGS. 17 and 18, where the FACS—based germ cell purification of bone marrow and peripheral blood preparations from adult female mice during estrus of the female reproductive cycle is shown.

Preparation of OSC Derived Compositions and Methods of Transfer

Methods for the preparation and transfer of mitochondria are known in the art and can be carried out as previously described in the art, or using comparable techniques. See, for example, Perez et al., *Cell Death and Differentiation* 2007 3:524-33. Epub 2006 Oct. 13, and Perez et al., *Nature* 2000, 403:500-1, the contents each of which are incorporated herein by reference. Briefly, OSCs can be isolated and cultured as described above. In one method, when OSC cultures reach 80% confluency, 2 ml of mitochondrial lysis buffer (0.3 M sucrose, 1 mM EDTA, 5 mM MOPS, 5 mM $KH_2PO_4$, 0.1% BSA) is added to each plate, and the cells are removed using a cell scraper. The cell suspension is transferred into a small glass tissue douncer and homogenized until smooth (approximately 10 up-and-down strokes), and the lysate is centrifuged at 600 g for 30 minutes at 4° C. The supernatant is removed and spun at 10,000 g for 12 minutes at 4° C., and the resulting crude mitochondrial pellet is resuspended in 0.2 ml of 0.25 M sucrose. This sample is then layered over a 25-60% Percoll density gradient diluted with 0.25 M sucrose and centrifuged at 40,000 g for 20 minutes at 17° C. The interface band is extracted from the gradient and washed in 2 volumes of 0.25 M sucrose before a final centrifugation at 14,000 g for 10 min at 4° C. to yield a mitochondrial pellet.

The mitochondrial pellet can also be prepared as described Frezza et al. *Nature Protocols* 2007 2:287-295, the contents of which are incorporated herein by reference. In specific embodiments of the invention, the total OSC-derived mitochondrial population in a tissue, cell, lysed cell, or fraction thereof can be isolated, characterized and/or enumerated using a FACS-based method with a fluorescent probe that specifically binds to mitochondria in a mitochondrial membrane potential (MMP)-independent manner. Fluorescent probes that specifically bind to mitochondria in a MMP-independent manner include, but are not limited to, accumulation dependent probes (e.g., JC-1 (red spectrum; Invitrogen T3168, Life Technologies Corp., Carlsbad, Calif.), MitoTracker Deep Red FM (Invitrogen M22426, Life Technologies Corp., Carlsbad, Calif.) and JC-1 (green spectrum; Invitrogen T3168, Life Technologies Corp., Carlsbad, Calif.). Functional (e.g., respiring) mitochondria can be sorted and collected, preferably with exclusion of residual unlysed cells and non-functional mitochondria, based on size and fluorescence intensity using mitochondrial tracking probes that indicate mitochondrial mass including, but not limited to, non-oxidation dependent probes (e.g., MitoTracker Green FM (Invitrogen M7514, Life Technologies Corp., Carlsbad, Calif.). Details of an exemplary protocol for conducting FACS with a non-oxidation dependent probe are provided below in Example 9. Optionally, the FACS-based method can also be employed to selectively yield a substantially pure population of functional (e.g., respiring) mitochondria using a mitochondrial membrane fluorescent probe that specifically binds to mitochondria in a MMP-dependent manner. Fluorescent probes that specifically bind to mitochondria in a MMP-dependent manner include, but are not limited to, reduced oxidative state mitotracker probes (e.g., MitoTracker Red CM-H2XRos (Invitrogen M7513, Life Technologies Corp., Carlsbad, Calif.) and MitoTracker Orange CM-H2TMRos (Invitrogen M7511, Life Technologies Corp., Carlsbad, Calif.). Furthermore, dual-labeling using MMP-dependent and MMP-independent probes can be conducted to quantitate the ratio of functional to total mitochondria in a tissue, cell, lysed cell or fraction derived therefrom. In specific embodiments, the ratio is greater than about 0.02, 0.025, 0.033, 0.04, 0.05, 0.1, or about 0.2. When using probes for differential screening based on MMP, spectral color is the major determining factor to designate functional mitochondria, and forward scatter can be used to distinguish the fluorescent mitochondria released from lysed cells from those still contained in residual unlysed cells.

Mitochondrial pellets can also be prepared as described by Taylor et al., *Nat. Biotechnol.* 2003 21(3): 239-40; Hanson et al., *Electrophoresis.* 2001 22(5): 950-9; and Hanson et al., *J. Biol. Chem.* 2001 276(19): 16296-301. In specific embodiments of the invention, the total OSC-derived mitochondrial population in a tissue, cell, lysed cell, or fraction thereof can be isolated, characterized and/or enumerated using a differential centrifugation method such as that described herein at Example 10 or using a sucrose gradient separation procedure such as that described herein at Example 11.

Following isolation, assessment of mitochondrial function or mtDNA integrity (e.g., mutations and deletions) can be conducted according to methods known in the art (Duran et al., *Fertility and Sterility* 2011 96(2):384-388; Aral et al., *Genetics and Molecular Biology* 2010 33:1-4; Chan et al., *Molecular Human Reproduction* 2005 11(12):843-846; Chen et al., *BMC Medical Genetics* 2011 12:8 and Example 8).

Populations of mitochondria sorted according to functional parameters (e.g., MMP dependent/active or MMP-independent/active plus inactive) or mitochondria from less preferred OSC sources, including samples of limited size, can be now be obtained according to the methods of the invention. Mitochondrial compositions of the invention can generate, for example, about 1 pmol ATP per fg mtDNA to about 6 pmol ATP per fg mtDNA (e.g., about 1, 2, 3, 4, 5, or 6 pmol ATP per fg mtDNA). In specific embodiments, between about 1.0 pmol to 1.4 pmol ATP per fg mtDNA is generated within about 10 minutes to about 15 minutes.

The percentage of mutations in a population of mitochondria can be assessed by first determining the number of mitochondria present in a biological sample and next, determining the copy number of mitochondrial DNA present in the sample. Standard mutation analysis can be employed and compared to the number of mitochondria and copy number of mitochondrial DNA to calculate the percentage of mutations in the population of mitochondria. For example, compositions and methods of the invention can provide a population of mitochondria in which less than about 5% to about 25% (e.g., about 5%, 10%, 15%, 20% to about 25%) of the mitochondrial DNA comprises a deletion mutation within nucleotides 8470-13447 of the mitochondrial genome.

The material to be injected (e.g., mitochondrial suspension) is transferred to a microinjection needle according to methods known in the art. Microinjection needles and holding pipettes can be made using a Sutter puller (Sutter Instruments, Novato, Calif., USA) and a De Fonbrune Microforge (EB Sciences, East Granby, Conn., USA). The microinjection needles have inner diameters of 5 µm with blunt tips. The material to be injected is aspirated into the needle by negative suction. Between about $1 \times 10^3$—to about $5 \times 10^4$ mitochondria from OSCs or their progeny can be injected (e.g., about 1, 2, 3, 4, 5, 6, 7, 8 to $9 \times 10^3$; about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 to about $5 \times 10^4$ mitochondria). The mitochondrial suspension in sucrose (e.g., 5-7 pl containing approximately $1 \times 10^3$-$5 \times 10^4$ mitochondria from OSCs or their progeny) can be injected into oocytes using a Piezo micromanipulator. Oocytes that survive the microinjection procedure are transferred for culture and optionally, assessment or cryopreservation prior to in vitro fertilization or intrauterine insemination. Methods of oocyte cryopreservation are well known in the art. For details, see for example, Porcu et al., *Molecular and Cellular Endocrinology* 2000 169:33-37; Mandelbaum, *Human Reproduction* 2000 15:43-47; and Fabbri et al., *Molecular and Cellular Endocrinology* 2000 169:39-42, the contents of which are incorporated herein by reference.

Methods for the preparation and transfer of nuclear-free cytoplasmic fractions are known in the art and can be carried out as previously described. See, for example, Cohen et al., *Mol Hum Reprod* 1998 4:269-80, the contents of which are incorporated herein by reference. Briefly, in one method, approximately 4 hours after egg retrieval, recipient eggs are exposed to 0.1% hyaluronidase, and mature eggs are selected for injection. All corona cells are removed with fine bore pipettes. Ooplasmic transfer can be performed by electrofusion of OSC ooplasts with intact MII oocytes. After exposure to 0.1% hyaluronidase, zonae are opened mechanically using a microspear. OSCs are exposed to hHTF medium containing cytochalasin B (CCB; Sigma Chemical Co., St Louis, Mo., USA) for 10 min at 37° C. Partitioning of human MII oocytes involves variable cytochalasin B concentration depending on their sensitivity (~2.5 mg/ml). Ooplasts of various sizes are separated from OSCs by withdrawing a portion of the ooplasm enclosed in the plasma membrane. Alignment and electrofusion in a mannitol solution is performed after insertion of the OSC derived ooplast into the perivitelline space of the recipient egg from which the polar body was removed. This can be done with a wide-bored polished microtool ~30-10 µm in diameter. The ooplast is sucked into the microtool and released once the tool is placed deeply into the perivitelline space. Oocytes that survive the electrofusion procedure are transferred for culture and optionally, assessment or cryopreservation prior to in vitro fertilization or intrauterine insemination.

Alternatively, conventional intracytoplasmic sperm injection (ICSI) methods can be employed in connection with the transfer of nuclear-free cytoplasmic fractions or isolated mitochondria. See, for example, Cohen et al., *Mol Hum Reprod* 1998 4:269-80, the contents of which are incorporated herein by reference. As one example, the zonae of the recipient eggs are opened mechanically over the polar body area using a microspear. The polar body is removed after re-positioning the oocyte on the holding pipette in such a way that the zona can be dissected using the closed microspear. The same position is used to insert the ooplast ~90° left of the area, which had contained the polar body. The zona is closed tight using the same tool. Electrofused cells are washed and incubated in mHTF for 40-90 min prior to ICSI. Spermatozoa are immobilized in 10% polyvinylpyrrolidone (PVP) for ICSI. The procedure is performed in hHTF while the short side of the aperture is at approximately 3 o'clock. The ICSI tool is moved through the artificial gap in order to avoid extrusion of ooplasm upon indentation of the zona during standard ICSI. Methods of in vitro fertilization are well known in the art. Couples are generally first evaluated to diagnose their particular infertility problem(s). These may range from unexplained infertility of both partners to severe problems of the female (e.g., endometriosis resulting in non-patent oviducts with irregular menstrual cycles or polycystic ovarian disease) or the male (e.g., low sperm count with morphological abnormalities, or an inability to ejaculate noinially as with spinal cord lesions, retrograde ejaculation, or reversed vasectomy). The results of these evaluations also determine the specific procedure to be performed for each couple.

Procedures often begin with the administration of a drug to down-regulate the hypothalamic/pituitary system (GnRH agonist). This process decreases serum concentrations of the gonadotropins, and developing ovarian follicles degenerate, thereby providing a set of new follicles at earlier stages of development. This permits more precise control of the maturation of these new follicles by administration of exogenous gonadotropins in the absence of influences by the hypothalamic pituitary axis. The progress of maturation and the number of growing follicles (usually four to ten stimulated per ovary) are monitored by daily observations using ultrasound and serum estradiol determinations. When the follicles attain preovulatory size (18-21 mm) and estradiol concentrations continue to rise linearly, the ovulatory response is initiated by exogenous administration of human chorionic gonadotropins (hCG).

Following the transplantation procedure, individual oocytes can be evaluated morphologically and transferred to a petri dish containing culture media and heat-inactivated serum. A semen sample is provided by the male partner and processed using a "swim up" procedure, whereby the most active, motile sperm will be obtained for insemination. If the female's oviducts are present, a procedure called GIFT (gamete intrafallopian transfer) can be performed at this time. By this approach, oocyte-cumulus complexes surrounded by sperm are placed directly into the oviducts by laparoscopy. This procedure best simulates the normal sequences of events and permits fertilization to occur within the oviducts. Not surprisingly, GIFT has the highest success rate with 22% of the 3,750 patients undergoing ova retrieval in 1990 having a live delivery. An alternative procedure ZIFT (zygote intrafallopian transfer) permits the selection of in vitro fertilized zygotes to be transferred to oviducts the day following ova retrieval. Extra zygotes can be cryopreserved at this time for future transfer or for donation to couples without female gametes. Most patients having more serious infertility problems, however, will require an additional one to two days incubation in culture so that preimplantation embryos in the early cleavage states can be selected for transfer to the uterus or oviduct. This IVF-UT (in vitro fertilization uterine transfer) procedure entails the transcervical transfer of several 2-6 cell (day 2) or 8-16 (day 3) preimplantation embryos to the fundus of the uterus (4-5 preimplantation embryos provides optimal success).

Procedures for in vitro fertilization are also described in U.S. Pat. Nos. 6,610,543 6,585,982, 6,544,166, 6,352,997, 6,281,013, 6,196,965, 6,130,086, 6,110,741, 6,040,340, 6,011,015, 6,010,448, 5,961,444, 5,882,928, 5,827,174, 5,760,024, 5,744,366, 5,635,366, 5,691,194, 5,627,066, 5,563,059, 5,541,081, 5,538,948, 5,532,155, 5,512,476, 5,360,389, 5,296,375, 5,160,312, 5,147,315, 5,084,004, 4,902,286, 4,865,589, 4,846,785, 4,845,077, 4,832,681, 4,790,814, 4,725,579, 4,701,161, 4,654,025, 4,642,094, 4,589,402, 4,339,434, 4,326,505, 4,193,392, 4,062,942, and 3,854,470, the contents of which are specifically incorporated by reference for their description of these procedures.

Alternatively, patients may elect to have the oocyte comprising exogenous, autologous OSC mitochondria reimplanted and fertilized in vivo using Intrauterine Insemination (IUD. IUI is a well known process that involves preparing and delivering a highly concentrated amount of active motile sperm directly through the cervix into the uterus. There are several techniques available for preparing the sperm for JUT. First, sperm is separated from seminal fluid. One method of sperm separation is known as "Density Gradient Separation". In this technique, motile sperm are separated from dead sperm and other cells through the use of viscous solution. After preparation, the sperm concentrate is placed through the cervix into the uterus by using a thin, flexible catheter and fertilization of the reimplanted oocyte follows.

The present invention is additionally described by way of the following illustrative, non-limiting Examples that provide a better understanding of the present invention and of its many advantages.

EXAMPLES

Herein, validated protocols are employed to demonstrate that OSCs can be reliably isolated from tissues of healthy young women and propagated in vitro for use in subsequent clinical procedures. The following examples are put forth for illustrative purposes only and are not intended to limit the scope of what the inventors regard as their invention.

Example 1

FACS-Based Protocol for OSC Isolation

The VASA antibody used by Zou et al., Nat Cell Biol 2009 11:631-636 to isolate mouse OSCs by immunomagnetic sorting is a rabbit polyclonal against the last 25 amino acids of the COOH-terminus of human VASA (DDX4) (ab13840; Abcam, Cambridge, Mass.). This region shares 96% overall homology with the corresponding region of mouse VASA (MVH). For comparative studies, a goat polyclonal antibody against the first 145 amino acids of the $NH_2$-terminus of human VASA (AF2030; R&D Systems, Minneapolis, Minn.) was used, which shares 91% overall homology with the corresponding region of mouse VASA.

Immunofluorescence analysis of young adult (2-month-old) mouse ovaries using either antibody showed an identical pattern of VASA expression that was restricted, as expected, to oocytes (FIG. 1a). Each antibody was then used for immunomagnetic sorting of dispersed young adult mouse ovary tissue (Zou et al., Nat Cell Biol 2009 11:631-636). For each preparation of cells, ovaries from 4 mice were pooled and dissociated by mincing followed by a two-step enzymatic digestion involving a 15-minute incubation with 800 U/ml collagenase [type N; prepared in Hank's balanced salt solution minus calcium and magnesium (HBSS)] followed by a 10-minute incubation with 0.05% trypsin-EDTA. Digestions were carried out in the presence of 1 µg/ml DNase-I (Sigma-Aldrich, St. Louis, Mo.) to minimize stickiness within the cell preparations, and trypsin was neutralized by addition of 10% fetal bovine serum (FBS; Hyclone, ThermoFisher Scientific, Inc., Waltham, Mass.). Ovarian dispersates were filtered through a 70-µm nylon mesh and blocked in a solution composed of 1% fatty-acid free bovine serum albumin (BSA; Sigma-Aldrich, St. Louis, Mo.) with either 1% normal goat serum (EMD Millipore, Billerica, Mass.; for subsequent reactions using ab13840 against VASA-COOH) or 1% normal donkey serum (Sigma-Aldrich, St. Louis, Mo.; for subsequent reactions using AF2030 against VASA-$NH_2$) in HBSS for 20 minutes on ice. Cells were then reacted for 20 minutes on ice with a 1:10 dilution of VASA antibody that recognizes either the COOH terminus (ab13840) or $NH_2$ terminus (AF2030). Afterwards, cells were washed 2 times in HBSS and incubated for 20 minutes on ice with a 1:10 dilution of either goat anti-rabbit IgG-conjugated microbeads (Miltenyi, Gladbach, Germany; ab13840 detection) or biotin-conjugated donkey anti-goat IgG (Santa Cruz Biotechnology, Santa Cruz, Calif.; AF2030 detection) followed by incubation with streptavidin-conjugated microbeads (Miltenyi; Gladbach, Germany). After one additional wash in HBSS, the cell preparations were loaded onto MACS columns and separated according to manufacturer's specifications (Miltenyi, Gladbach, Germany). For experiments to visualize potential antibody-bead interaction with individual oocytes, adult female mice were superovulated by injection of pregnant mare serum gonadotropin (PMSG, 10 IU; Sigma-Aldrich, St. Louis, Mo.) followed by human chorionic gonadotropin (hCG, 10 IU; Sigma-Aldrich, St. Louis, Mo.) 46-48 hours later. Oocytes were collected from oviducts 15-16 hours after hCG injection, denuded of cumulus cells using hyaluronidase (Irvine Scientific, Santa Ana, Calif.) and washed with human tubal fluid (HTF; Irvine Scientific, Santa Ana, Calif.) supplemented with BSA. Dispersed ovarian cells or isolated oocytes were blocked and incubated with primary antibodies against VASA as described above. After washing in HESS, cells were reacted with species-appropriate secondary antibodies conjugated to 2.5-µm Dynabeads (Invitrogen, Life Technologies Corp., Carlsbad, Calif.). Suspensions were placed into 1.5 ml Eppendorf tubes for separation using a Dynal MPC®-S Magnetic Particle Concentrator (Dynal Life Technologies Corp., Carlsbad, Calif.).

Figure 1B:
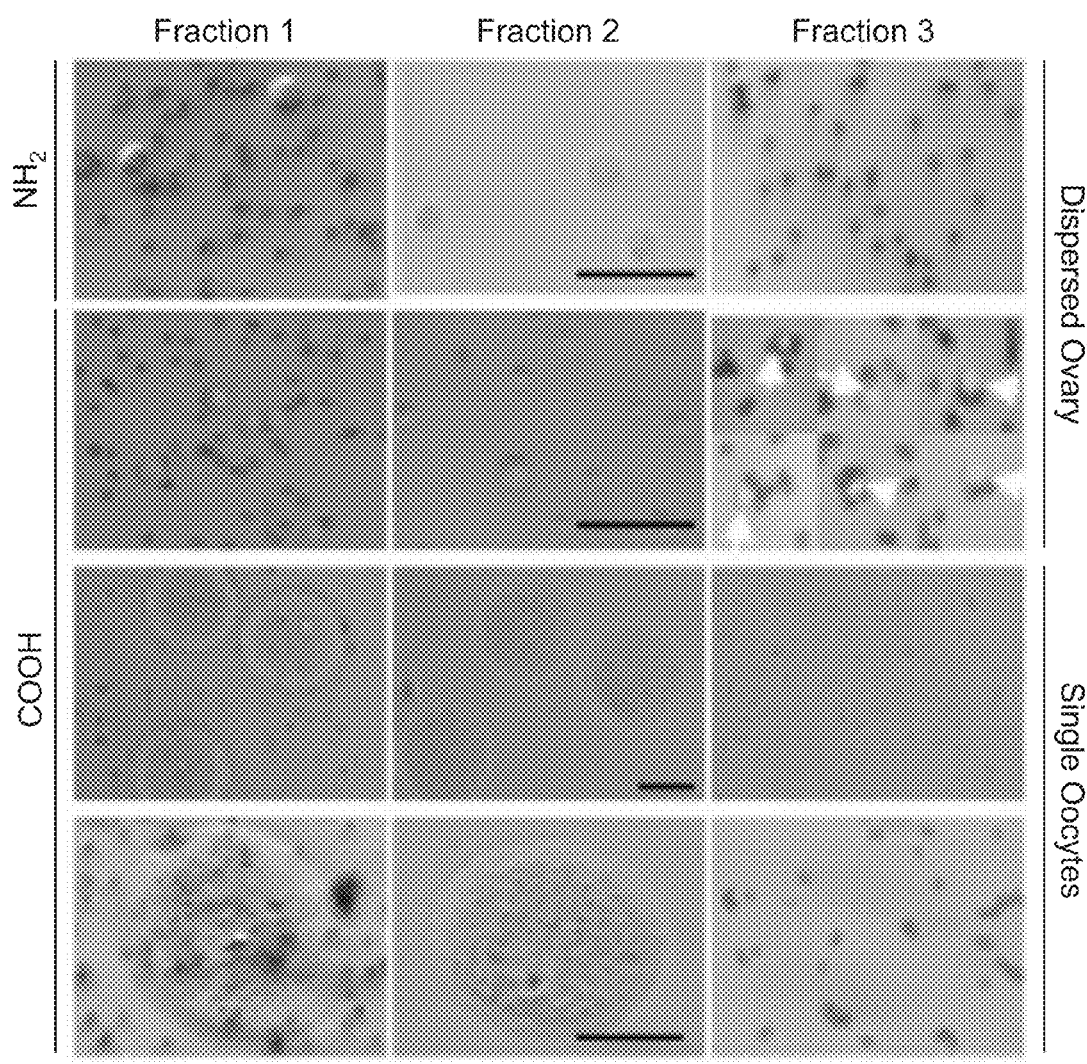
In FIG. 1b, immunomagnetic sorting of dispersed mouse ovaries or isolated oocytes is shown using antibodies against the $NH_2$ or COOH terminus of VASA. Fraction 1 contains cells plus beads prior to separation, Fraction 2 is a wash or flow-through fraction (non-immunoreactive) and Fraction 3 is a bead fraction (VASA-positive cells).
Figure 2:
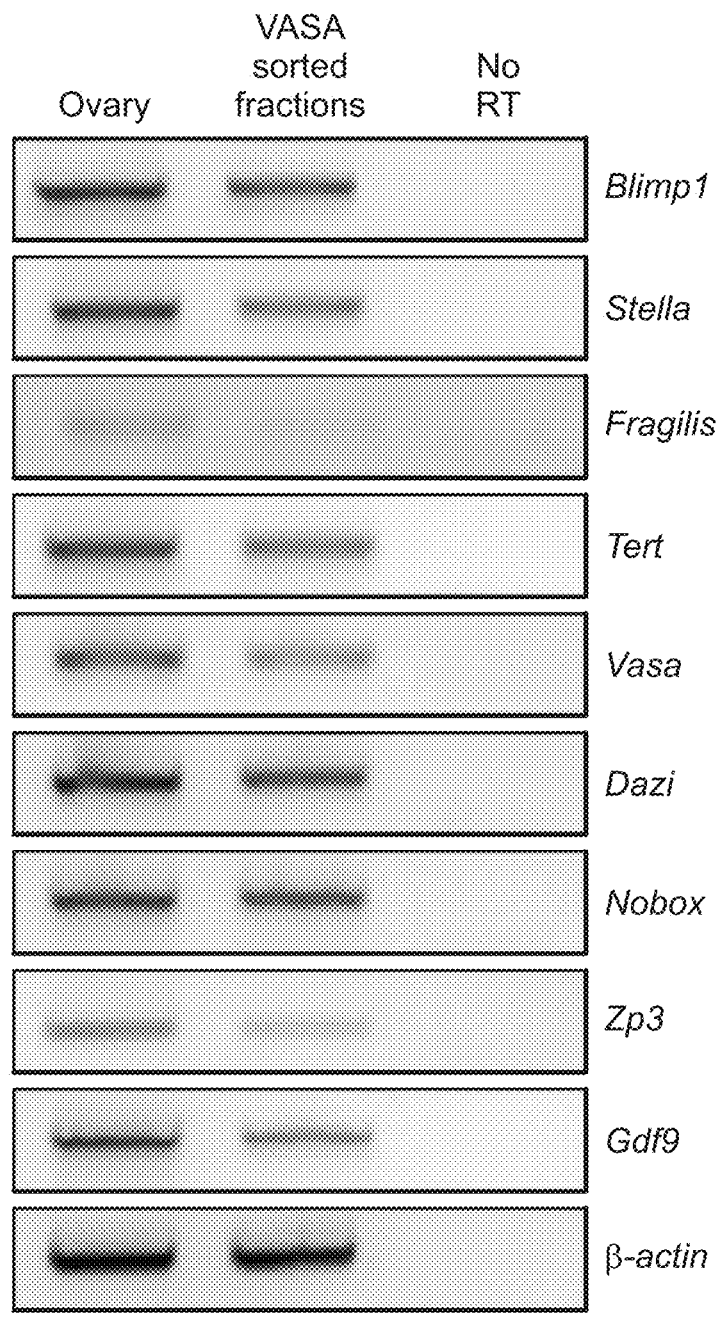
FIG. 2 depicts OSC fractions isolated from adult mouse ovaries by immunomagnetic bead sorting that contain contaminating oocytes. Gene expression analysis of germline markers (Blimp1, Stella, Fragilis, Tert, Vasa, Dazl) and oocyte-specific markers (Nobox, Zp3, Gdf9) is shown in young adult mouse ovaries (positive control) or the final cell fraction obtained following VASA-COOH antibody-based immunomagnetic bead sorting of dispersed young adult mouse ovaries (No RT, PCR of sorted cell RNA sample without reverse transcription; β-actin, sample loading control).

No cells were obtained in the bead fraction when the VASA-$NH_2$ antibody was used; however, 5-8 µm cells bound to the magnetic beads were observed when the VASA-COOH antibody was used (FIG. 1b). Analysis of these cells revealed a germline gene expression pattern consistent with that reported for OSCs isolated previously by Zou et al., Nat Cell Biol 2009 11:631-636 using immunomagnetic sorting (FIG. 2). Although isolated oocytes assessed in parallel using the VASA-COOH antibody were always detected in the non-immunoreactive wash fraction (FIG. 1b), additional marker analysis of the VASA-positive cell fraction obtained by immunomagnetic sorting revealed several oocyte-specific mRNAs including Nobox, Zp3 and Gdf9 (FIG. 2). These findings indicate that while oocytes do not exhibit cell surface expression of VASA when analyzed as individual entities (FIG. 1b), oocytes are nonetheless a contaminating cell type following immunomagnetic sorting of OSCs from dispersed ovary tissue. This outcome most likely reflects either a non-specific physical carry-over of oocytes during the bead centrifugation steps or reactivity of cytoplasmic VASA in plasma membrane-compromised (damaged) oocytes with the COOH antibody. Either case would be alleviated by use of FACS.

The reactivity of each antibody with dispersed mouse ovarian cells was next assessed by FACS. For each experiment, ovarian tissue (mouse: 4 ovaries pooled; human: 10×10×1 mm thick, cortex only) was dissociated, blocked and reacted with primary antibody (ab13840 for VASA-COOH or AF2030 for VASA-$NH_2$) as described above. After washing with HMS, cells were incubated with a 1:500 dilution of goat anti-rabbit IgG conjugated to Alexa Fluor 488 (Invitrogen, Life Technologies Corp., Carlsbad, Calif.; ab13840 detection) or donkey anti-goat IgG conjugated to Alexa Fluor 488 (Invitrogen, Life Technologies Corp., Carlsbad, Calif.; AF2030 detection) for 20 minutes on ice, and washed with HBSS. Labeled cells were then filtered again (35-μm pore diameter) and sorted by FACS using a FACSAria II cytometer (BD Biosciences, Becton Dickinson and Company, Franklin Lakes, N.J.; Harvard Stem Cell Institute), gated against negative (unstained and no primary antibody) controls. Propidium iodide was added to the cell suspension just prior to sorting for dead cell exclusion. Freshly-isolated VASA-positive viable cells were collected for gene expression profiling, assessment of teratoma formation capacity or in vitro culture. For some experiments, cells were fixed in 2% neutral-buffered paraformaldehyde (PFA) and permeabilized with 0.1% Triton-X100 prior to reaction with primary antibody against the $NH_2$ terminus of VASA (AF2030) and detection by FACS after reaction with donkey anti-goat IgG conjugated to Alexa Fluor 488. For re-sort experiments, viable cells were reacted with VASA-COOH antibody (ab13840) and sorted by FACS after reaction with a goat anti-rabbit IgG conjugated to allophcocyanin (APC) (Jackson Immunoresearch Laboratories, Inc., West Grove Pa.). Resultant APC-positive (VASA-COOH positive) viable cells were then either left intact or fixed and permeabilized prior to incubation with VASA-$NH_2$ antibody (AF2030), followed by incubation with donkey anti-goat IgG conjugated to Alexa Fluor 488 and FACS analysis.

Figure 1C:
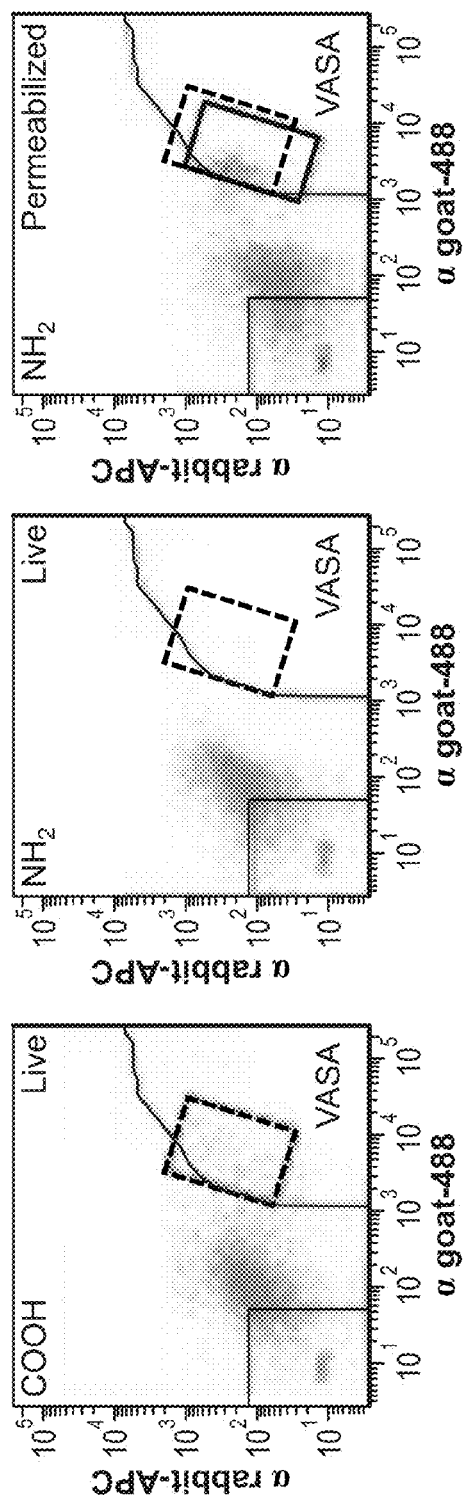
In FIG. 1c, FACS analysis of live or permeabilized cells from dispersed mouse ovaries using antibodies against the $NH_2$ or COOH terminus of VASA is shown. Viable VASA-positive cells are only detected with the COOH antibody (dashed box) whereas permeabilization enables isolation of VASA-positive cells using the $NH_2$ antibody (dashed box).
Figure 1D:
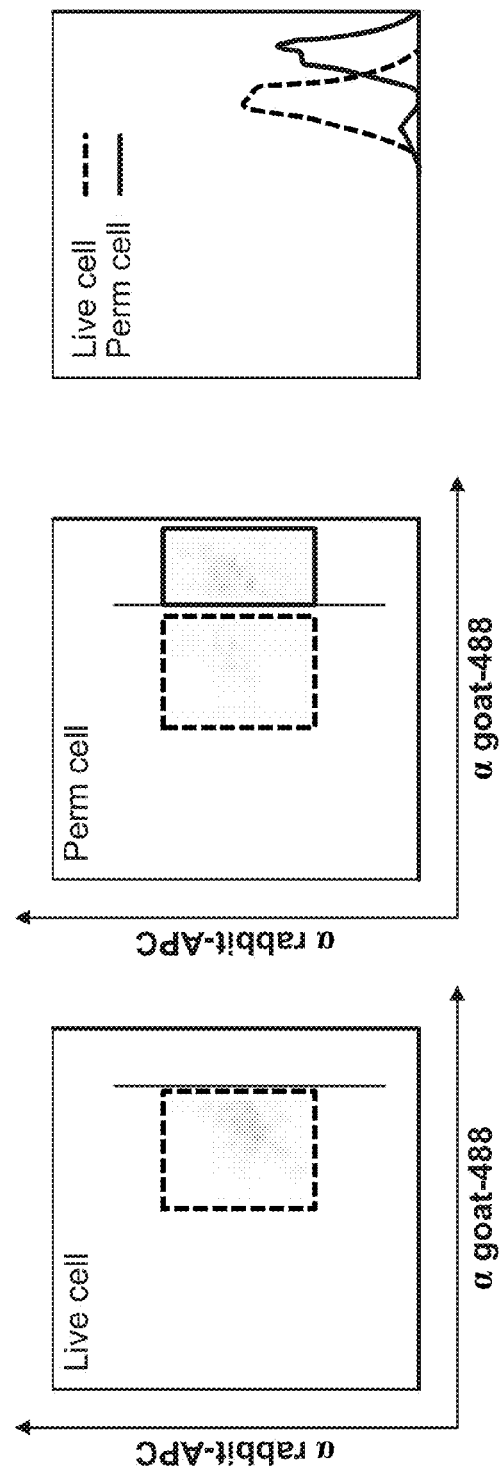
In FIG. 1d, permeabilization of viable VASA-positive cells (dashed box) obtained with the COOH antibody enables re-isolation of the same cells by FACS using the $NH_2$ antibody (dashed box).
Figure 1E:
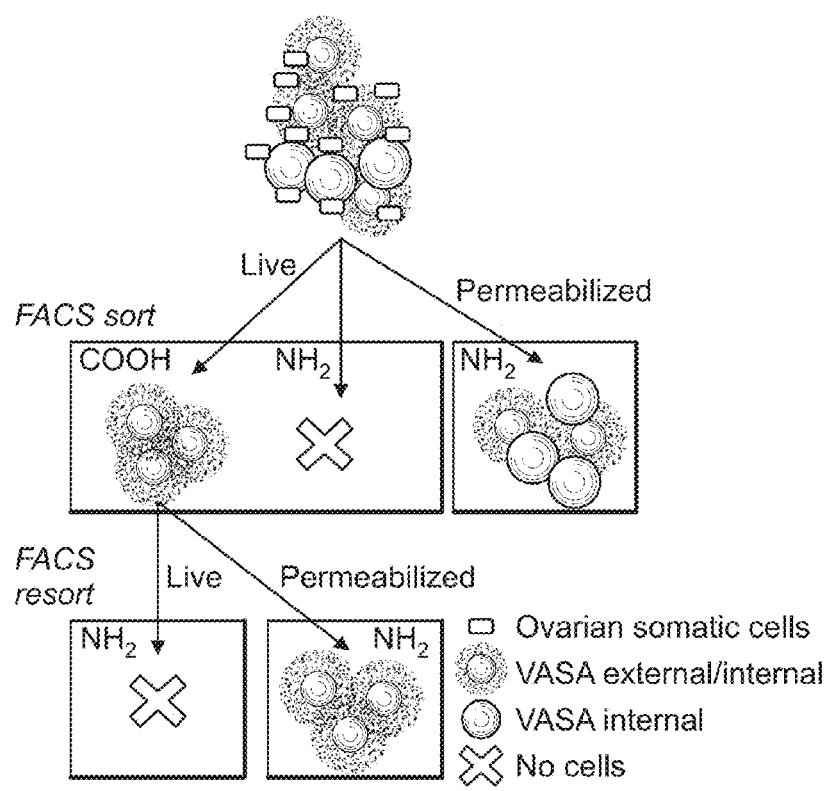
In FIG. 1e, a schematic representation of the FACS protocols employed using the VASA-COOH antibody for isolation of viable OSCs is shown.
Figure 1F:
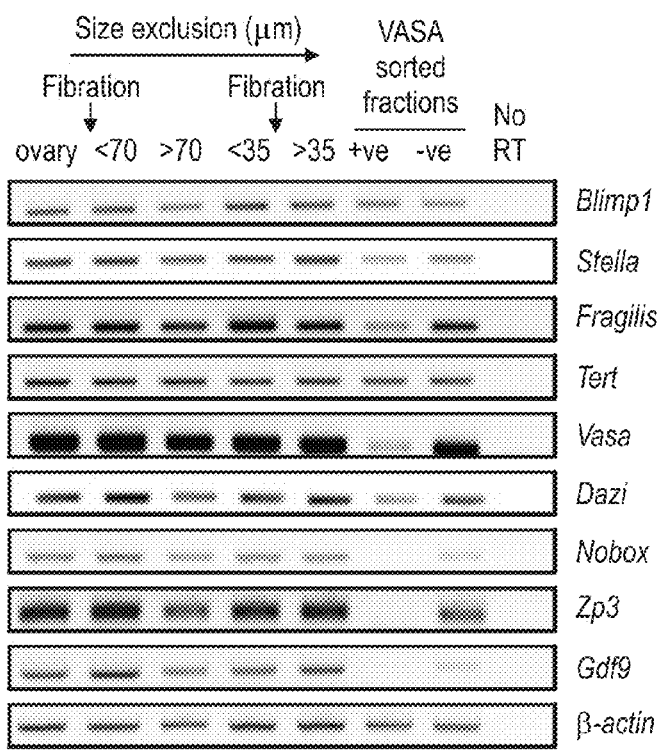
FIG. 1f depicts gene expression analysis of germline markers [Blimp1 (also referred to as PR domain containing 1 with ZNF domain or Prdm1), Stella, Fragilis (also referred to as interferon induced transmembrane protein 3 or Ifitm3), Tert (telomerase reverse transcriptase), Vasa, Dazl (deleted in azoospermia like)] and oocyte markers [Nobox (newborn ovary homeobox), Zp3 (zona pellucida glycoprotein 3), Gdf9 (growth differentiation factor 9)] in each cell fraction produced during the ovarian dispersion process to obtain cells for FACS-based isolation of OSCs using the VASA-COOH antibody (+ve, VASA-positive viable cell fraction after FACS; −ve, VASA-negative viable cell fraction after FACS; No RT, PCR of RNA sample without reverse transcription; β-actin, sample loading control).

In agreement with the magnetic bead sorting results, viable VASA-positive cells were obtained only when the COOH antibody was used (FIG. 1c). However, if the ovarian cells were permeabilized prior to FACS, a VASA-positive cell population was obtained using the $NH_2$ antibody (FIG. 1c). Further more, if the viable VASA-positive cells isolated by FACS using the COOH antibody were permeabilized and re-sorted, the same cell population was recognized by the VASA-$NH_2$ antibody (FIG. 1d). As a final means to confirm validity of this OSC isolation method, fractions of cells at each step of the protocol were assessed by gene expression analysis using a combination of markers for germ cells (Blimp1/Prdm1, Stella1Dppa3, Fragilis/Ifitm3, Tert, Vasa, Dazl) and oocytes (Nobox, Zp3, Gdf9). To obtain cells for FACS, ovarian tissue was minced and enzymatically digested using collagenase and trypsin, passed through a 70-μm filter to remove large tissue clumps, and then passed through a 35-μm filter to obtain a final fraction of cells. Every fraction of cells through each step of the protocol, with the exception of the VASA-positive viable cell fraction obtained by FACS, expressed all germline and oocyte markers (FIG. 1f). While the FACS-sorted VASA-positive cell fraction expressed all germline markers, no oocyte markers were detected (FIG. 1f). Thus, unlike the oocyte contamination observed when OSCs are isolated by immunomagnetic sorting using the VASA-COOH antibody (see FIG. 2), use of this same antibody with FACS provides a superior strategy to obtain adult ovary-derived OSC fractions free of oocytes.

Example 2

Isolation of OSCs From Human Ovaries

Figures 12A, 12B:
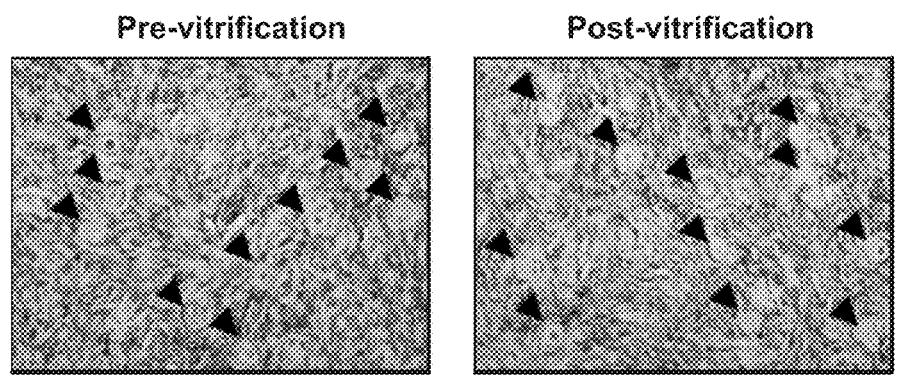
FIGS. 12*a* and 12*b* show the histological appearance of adult human ovarian cortical tissue before and after vitrification, highlighting the maintenance of tissue integrity and the large numbers of oocytes (black arrowheads) that survive the freeze-thaw procedure.
Figure 12C:
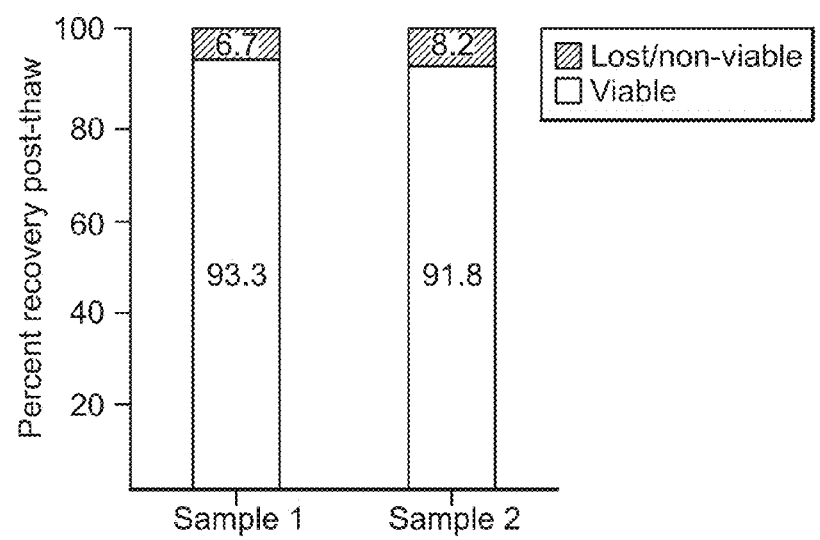
In FIG. 12*c*, the percent cell loss following freeze-thaw of freshly-isolated human OSCs is shown (results from two different patients).

With written informed consent, ovaries were surgically removed from 6 female patients between 22-33 (28.5±4.0) years of age with Gender Identity Disorder for sex reassignment at Saitama Medical Center. The outer cortical layer was carefully removed, vitrified and cryopreserved (Kagawa et al., Reprod. Biomed. 2009 Online 18:568-577; FIG. 12). Briefly, 1 mm-thick cortical fragments were cut into 100-$mm^2$ (10×10 mm) pieces, incubated in an equilibration solution containing 7.5% ethylene glycol (EG) and 7.5% dimethylsulfoxide (DMSO) at 26° C. for 25 minutes, and then incubated in a vitrification solution containing 20% EG, 20% DMSO and 0.5 M sucrose at 26° C. for 15 minutes prior to submersion into liquid nitrogen. For experimental analysis, cryopreserved ovarian tissue was thawed using the Cryotissue Thawing Kit (Kitazato Biopharma, Fuji City, Shizuoka, Japan) and processed immediately for histology, xenografting or OSC isolation. Using the COOH antibody, viable VASA-positive cells between 5-8 μm in diameter were also consistently isolated by FACS from human ovarian cortical tissue biopsies of all patients between 22-33 years of age, with a percent yield (1.7%±0.6% VASA-positive versus total viable cells sorted; mean±SEM, n=6) that was comparable to the yield of OSCs from young adult mouse ovaries processed in parallel (1.5%±0.2% VASA-positive versus total viable cells sorted; mean±SEM, n=15). This percent yield is the incidence of these cells in the final pool of viable single cells sorted by FACS, which represents a fraction of the total number of cells present in ovaries prior to processing. To estimate the incidence of OSCs per ovary, the genomic DNA content per ovary of 1.5-2 month-old mice was determined (1,774.44±426.15 μg; mean±SEM, n=10) and divided into genomic DNA content per fraction of viable cells sorted per ovary (16.41±4.01 μg; mean±SEM, n=10). Assuming genomic DNA content per cell is equivalent, how much of the total ovarian cell pool is represented by the total viable sorted cell fraction obtained after processing was determined. Using this correction factor, the incidence of OSCs per ovary was estimated to be 0.014%±0.002% [0.00926×(1.5%±0.2%)]. With respect to OSC yield, this number varied across replicates but between 250 to slightly over 1,000 viable VASA-positive cells per adult ovary were consistently obtained after FACS of dispersates initially prepared from a pool of 4 ovaries.

Figures 3F, 3G, 3H, 3I, 3J, 3K:
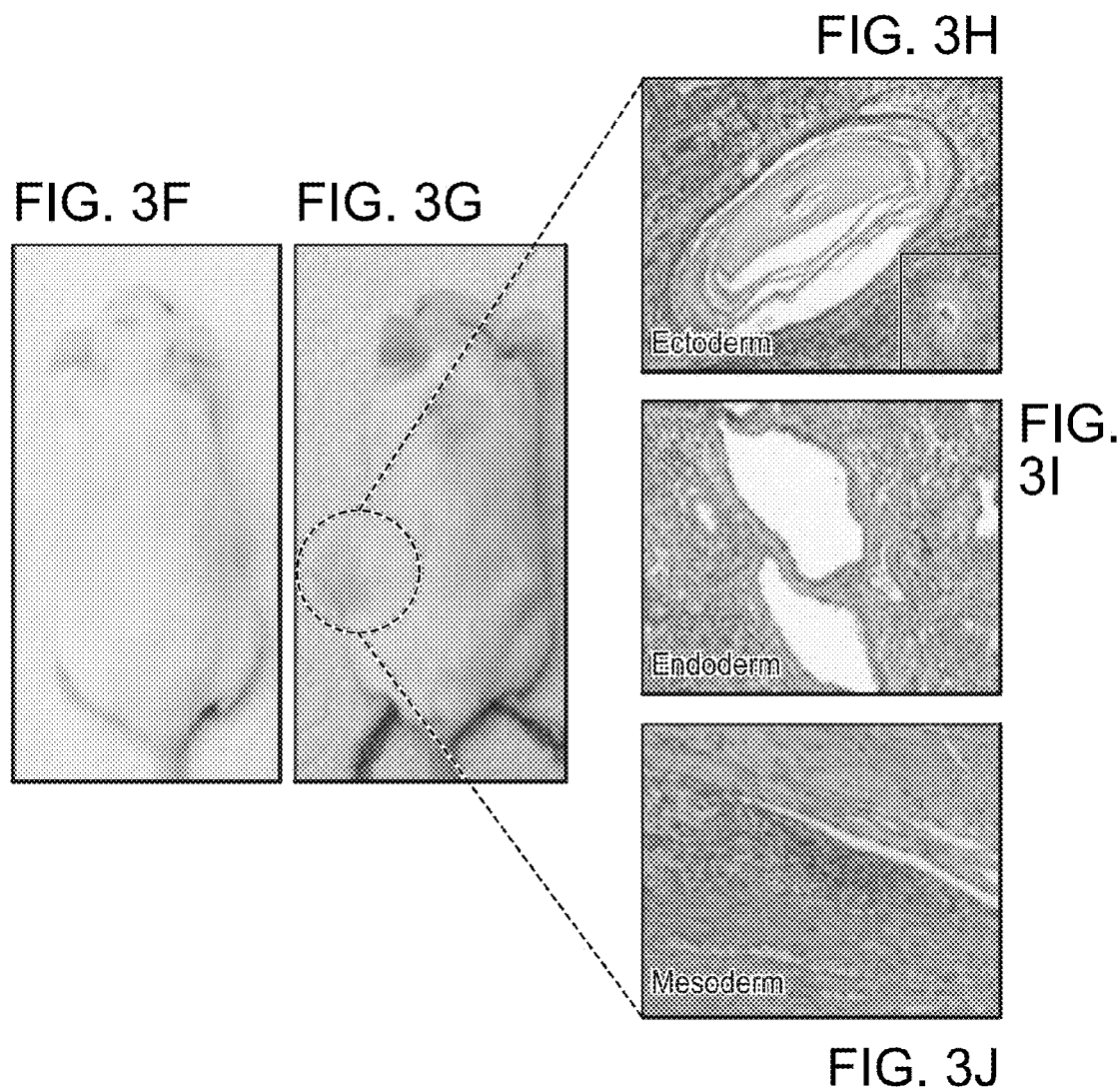
In FIG. 3f through FIG. 3k, a teratoma formation assay showing an absence of tumors in mice 24 weeks after receiving injections of mouse OSCs (3f) compared with development of tumors in mice 3 weeks after injection of mouse embryonic stem cells (ESCs) is shown (FIG. 3g through FIG. 3j; panels 3h through 3j show examples of cells from all three germ layers, with neural rosette highlighted in panel 3 h, inset), along with a summary of the experimental outcomes (3k).

Analysis of freshly-isolated VASA-positive cells from both mouse and human ovaries (FIG. 3a, 3b) revealed a similar size and morphology (FIG. 3c, 3d), and a matched gene expression profile rich in markers for early germ cells (Saitou et al., Nature 2002 418:293-300; Ohinata et al., Nature 2005 436:207-213; Dolci et al., Cell Sci. 2002 115:1643-1649) (Blimp1, Stella, Fragilis and Tert; FIG. 3e). These results agree with the morphology and gene expression profile of mouse OSCs reported in the scientific literature (Zou et al., Nat Cell Biol 2009 11:631-636, Pacchiarotti et al., Differentiation 2010 79:159-170).

To further define characteristic features of VASA-positive cells obtained from adult ovaries, mouse OSCs were tested using an in vivo teratoma formation assay. This was important since a recent study has reported the isolation of Oct3/4-positive stem cells from adult mouse ovaries that possess the teratoma-forming capacity of embryonic stem cells (ESCs) and induced pluripotent stem cells (iPSCs) (Gong et al., *Fertil. Steril.* 2010 93:2594-2601). Ovaries were collected from a total of 100 young adult female mice, dissociated and subjected to FACS for isolation of VASA-COOH positive viable cells, as described above. Freshly isolated mouse OSCs were injected subcutaneously near the rear haunch of NOD/SCID female mice ($1\times10^5$ cells injected per mouse). As a control, mouse embryonic stem cells (mESC v6.5) were injected into age-matched female mice in parallel ($1\times10^5$ cells injected per recipient mouse). Mice were monitored weekly for up to 6 months for tumor formation.

As expected, 100% of the mice transplanted with mouse ESCs used as a positive control developed teratomas within 3 weeks; however, no teratomas were observed in mice transplanted in parallel with VASA-positive cells isolated from adult mouse ovaries, even at 24 weeks post-transplant (FIGS. 3*f-k*). Thus, while OSCs express numerous stem cell and primitive germ cell markers (Zou et al., *Nat Cell Biol* 2009 11:631-636, Pacchiarotti et al., *Differentiation* 2010 79:159-170; see also FIG. 1*f* and FIG. 3*e*), these cells are clearly distinct from other types of pluripotent stem cells described to date.

Example 3

Generation of Oocytes from FACS-Purified Mouse OSCs

The ability of FACS-purified mouse OSCs, engineered to express GFP through retroviral transduction (after their establishment as actively-dividing germ cell-only cultures in vitro) to generate oocytes following transplantation into ovaries of adult female mice was assessed. To ensure the outcomes obtained were reflective of stable integration of the transplanted cells into the ovaries and also were not complicated by pre-transplantation induced damage to the gonads, $1\times10^4$ GFP-expressing mouse OSCs were injected into ovaries of non-chemotherapy conditioned wild-type recipients at 2 months of age and animals were maintained for 5-6 months prior to analysis. Between 7-8 months of age, transplanted animals were induced to ovulate with exogenous gonadotropins (a single intraperitoneal injection of PMSG (10 IU) followed by hCG (10 IU) 46-48 hours later), after which their ovaries and any oocytes released into the oviducts were collected. Ovulated cumulus-oocyte complexes were transferred into HTF supplemented with 0.4% BSA, and assessed by direct fluorescence microscopy for GFP expression. Developing follicles containing GFP-positive oocytes were readily detectable, along with follicles containing GFP-negative oocytes, in ovaries of females that received GFP-expressing mouse OSCs initially purified by FACS (FIG. 4*a*).

After oviductal flushing, complexes containing expanded cumulus cells surrounding centrally-located oocytes both lacicing and expressing GFP were observed. Mixing of these complexes with sperm from wild-type males resulted in fertilization and development of preimplantation embryos. For in vitro fertilization (rvF), the cauda epididymides and vas deferens were removed from adult wild-type C57BL/6 male mice and placed into HTF medium supplemented with BSA. Sperm were obtained by gently squeezing the tissue with tweezers, capacitated for 1 hour at 37° C., and then mixed with cumulus-oocyte complexes ($1-2\times10^6$ sperm/ml in HTFP medium supplemented with BSA) for 4-5 hours. Inseminated oocytes were then washed of sperm and transferred to fresh medium. At 4-5 hours post-insemination, oocytes (fertilized and unfertilized) were transferred to 50 µl drops of KSOM-AA medium (Irvine Scientific, Santa Ana, Calif.), and the drops were covered with mineral oil to support further preimplantation embryonic development. Light and fluorescence microscopic examination was performed every 24 hours for a total of 144 hours to monitor embryo development to the hatching blastocyst stage (Selesniemi et al., *Proc. Natl. Acad. Sci. USA* 2011 108:12319-12324). Ovarian tissue harvested at the time of ovulated oocyte collection from the oviducts was fixed and processed for immunohistochemical detection of GFP expression using a mouse monoclonal antibody against GFP (sc9996; Santa Cruz Biotechnology, Santa Cruz, Calif.) along with the MOM™ kit (Vector Laboratories, Burlingame, Calif.), as detailed previously (Lee et al., *J. Clin. Oncol.* 2007 25:3198-3204). Ovaries from non-transplanted wild-type female mice and from TgOG2 transgenic female mice served as negative and positive controls, respectively, for GFP detection.

Figures 4C, 4D, 4E:
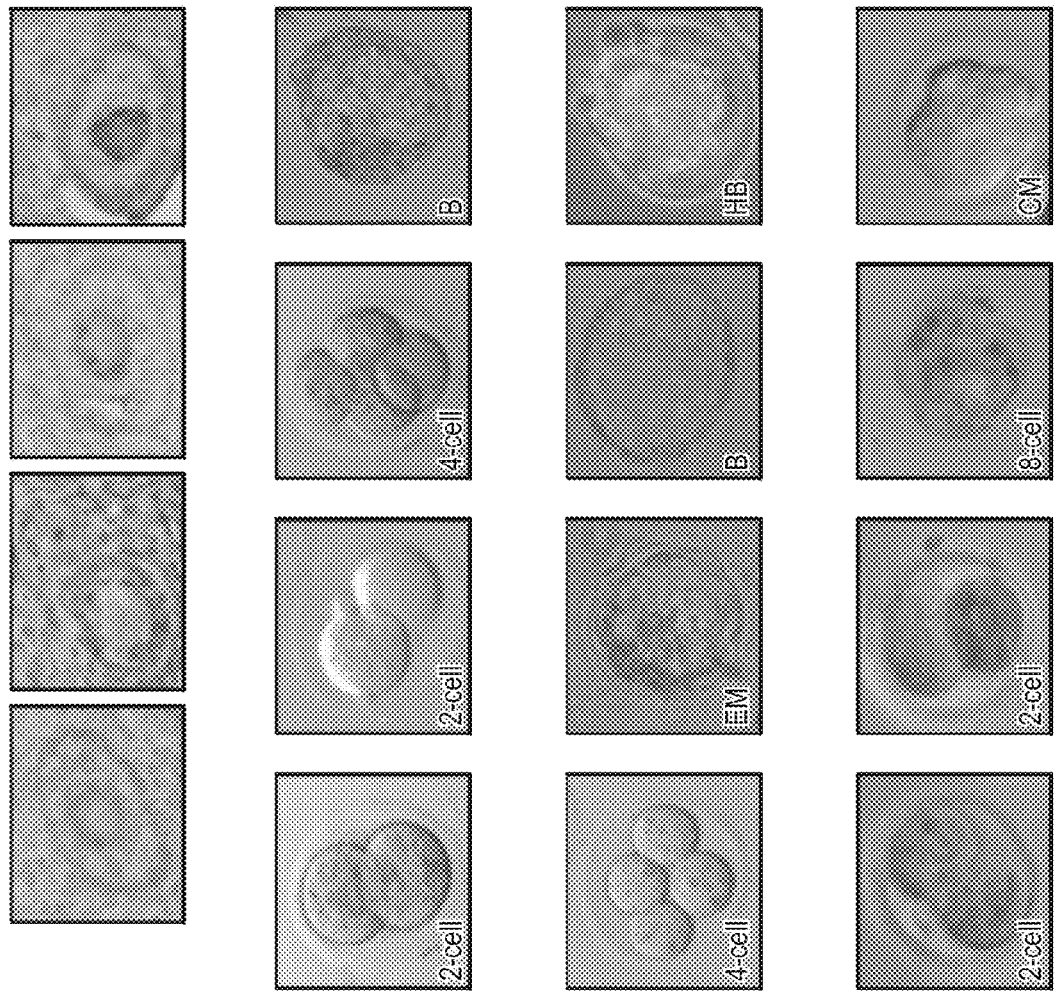
In FIG. 4c, examples of ovulated GFP-negative eggs (in cumulus-oocyte complexes), and resultant embryos [2-cell, 4-cell, compact morula (CM) and early blastocyst (EB) stage embryos are shown as examples] generated by IVF are shown, following induced ovulation of wild-type female mice that received intraovarian transplantation of GFP-expressing OSCs 5-6 months earlier.
In FIGS. 4d and 4e, examples of GFP-positive eggs (in cumulus-oocyte complexes) obtained from the oviducts are shown following induced ovulation of wild-type female mice that received intraovarian transplantation of GFP-expressing OSCs 5-6 months earlier. These eggs were in vitro fertilized using wild-type sperm, resulting in 2-cell embryos that progressed through preimplantation development [examples of GFP-positive embryos at the 2-cell, 4-cell, 8-cell, compacted morula (CM), expanded morula (EM), blastocyst (B) and hatching blastocyst (HB) stage are shown] to form hatching blastocysts 5-6 days after fertilization.
Figure 5A:
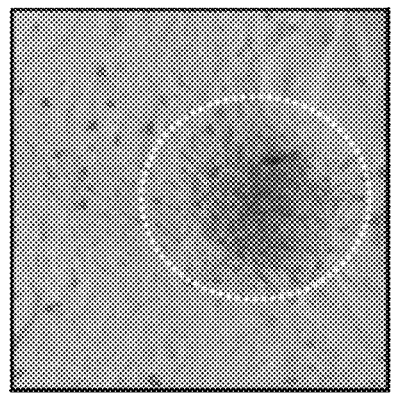
FIG. 5 depicts germ cell colony formation by mouse and human OSCs in vitro. Immunofluorescence-based analysis of VASA expression is shown in FIGS. 5b and 5d; (with DAPI counterstain) in typical germ cell colonies formed by mouse (5a, 5b) and human (5c, 5d) OSCs after establishment on mouse embryonic fibroblasts (MEFs) in vitro (typical colonies are highlighted by white dashed lines).
Figure 5B:
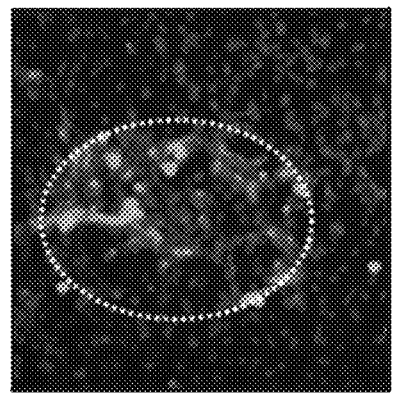
Figure 5C:
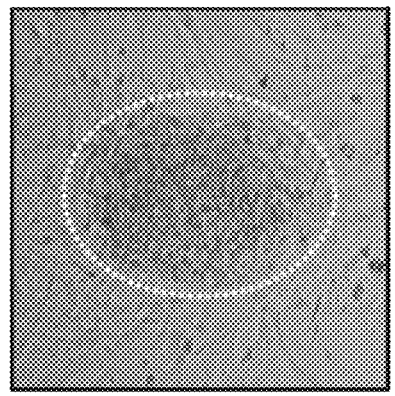
Figure 5D:
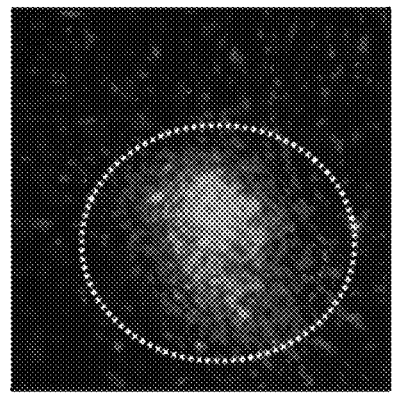

Preimplantation embryos derived from fertilized GFP-positive eggs retained GFP expression through the hatching blastocyst stage (FIG. 4*b-d*). From the 5 adult wild-type female mice transplanted with GFP-expressing OSCs 5-6 months earlier, a total of 31 cumulus-oocyte complexes were retrieved from the oviducts, 23 of which successfully fertilized to produce embryos. The presence of cumulus cells around each oocyte made it impossible to accurately determine the numbers of GFP-negative versus GFP-positive oocytes ovulated. However, evaluation of the 23 embryos produced following in vitro fertilization (IVF) revealed that 8 were GFP-positive, with all 5 mice tested releasing at least one egg at ovulation that fertilized to produce a GFP-positive embryo. These findings indicate that OSCs isolated or purified by VASA-COOH antibody-based FACS, like their previously reported counterparts isolated by immunomagnetic sorting (Zou et al., *Nat Cell Biol* 2009 11:631-636), generate functional oocytes in vivo. However, our data also show that chemotherapy conditioning prior to transplantation is not, as previously reported (Zou et al., *Nat Cell Biol* 2009 11:631-636), required for OSCs to engraft and generate functional oocytes in adult ovary tissue.

Example 4

In vitro Characterization of Candidate Human OSCs

Using parameters described previously for in vitro propagation of mouse OSCs (Zou et al., *Nat Cell Biol* 2009 11:631-636), adult mouse and human ovary-derived VASA-positive cells were placed into defined cultures with mitotically-inactive mouse embryonic fibroblasts (MEFs) as feeders. Briefly, cells were cultured in MEMa (Invitrogen, Life Technologies Corp., Carlsbad, Calif.) supplemented with 10% FBS (Hyclone, ThermoFisher Scientific, Inc., Waltham, Mass.), 1 mM sodium pyruvate, 1 mM non-essential amino acids, 1×-concentrated penicillin-streptomycin-glutamine (Invitrogen, Life Technologies Corp., Carlsbad, Calif.), 0.1 mM (β-mercaptoethanol (Sigma, St. Louis, Mo.), 1×-concentrated N-2 supplement (R&D Systems, Minneapolis, Minn.), leukemia inhibitory factor (LIF; $10^3$ units/ml; EMD) Millipore, Inc., Billerica, Mass.), 10 ng/ml recombinant human epidermal growth factor (rhEGF; Invitrogen, Life Technologies Corp., Carlsbad, Calif.), 1 ng/ml basic fibroblast growth factor (bFGF; Invitrogen, Life Technologies Corp., Carlsbad, Calif.), and 40 ng/ml glial cell-derived neurotropic factor (GDNF; R&D Systems, Minneapolis, Minn.). Cultures were refreshed by the addition of 40-80 μl of new medium every other day, and cells were re-plated on fresh MEFS every two weeks. To assess proliferation, MEF-free OSC cultures were treated with 10 μl BrdU (Sigma-Aldrich, St. Louis, Mo.) for 48 hours prior to fixation in 2% PFA for dual immunofluorescence-based detection of BrdU incorporation (mitotically-active cells) and VASA expression (germ cells), as described (Zou et al., Nat Cell Biol 2009 11:631-636). No signal was detected if primary antibodies were omitted or replaced with an equivalent dilution of normal rabbit serum (not shown).

Freshly-isolated OSCs could be established as clonal lines, and the colony formation efficiency for human OSCs not seeded onto MEFs ranged from 0.18% to 0.40%. Accurate assessment of colony formation efficiency could not be performed using MEFs as initial feeders, the latter of which greatly facilitates establishment of mouse and human OSCs in vitro. After 10-12 weeks (mouse) or 4-8 weeks (human) in culture, actively-dividing genii cell colonies became readily apparent (FIG. 5). Once established and proliferating, the cells could be re-established as germ cell-only cultures in the absence of MEFs without loss of proliferative potential. Dual analysis of VASA expression and bromodeoxyuridine (BrdU) incorporation in MEF-free cultures revealed large numbers of double-positive cells (FIG. 6a-d), confirming that adult mouse and human ovary-derived VASA-positive cells were actively dividing. At this stage, mouse cells required passage at confluence every 4-5 days with cultures split 1:6-1:8 (estimated doubling time of 14 hours; FIG. 6e). The rate of mouse OSC proliferation was approximately 2-3 fold higher than that of human germ cells maintained in parallel, the latter of which required passage at confluence every 7 days with cultures split 1:3-1:4. Cell surface expression of VASA remained detectable on the surface of more than 95% of the cells after months of propagation (FIG. 6f). The remaining cells not detected by FACS using the VASA-COOH antibody were large (35-50 μm in diameter) spherical cells spontaneously produced by mouse and human OSCs during culture, which exhibited cytoplasmic expression of VASA and are described in detail in Example 5.

Figure 6G:
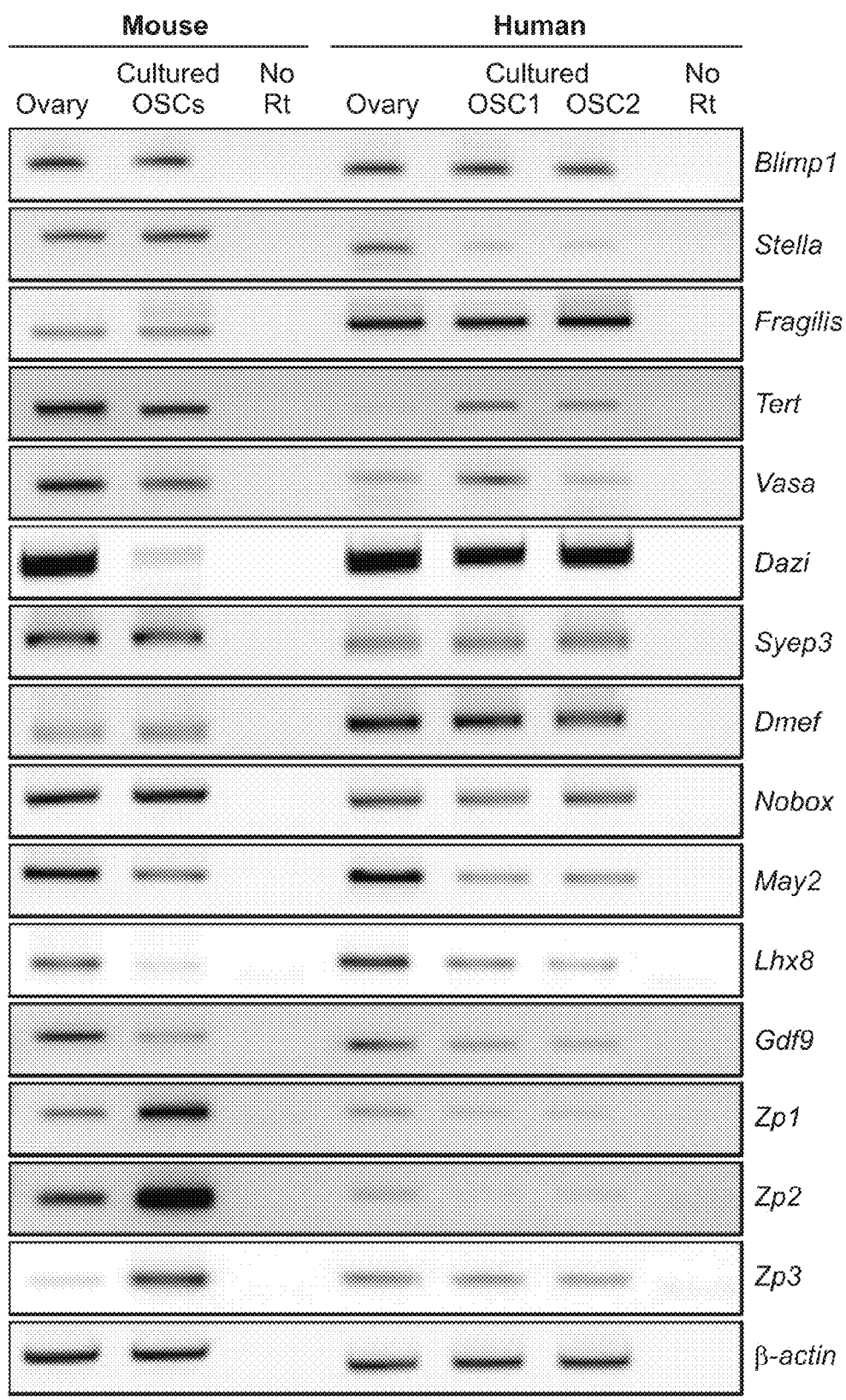
FIG. 6g indicates the gene expression profile of starting ovarian material and cultured mouse and human OSCs after 4 or more months of propagation in vitro (No RT, PCR of RNA sample without reverse transcription; (β-actin, sample loading control). Two different human OSC lines (OSC1 and OSC2) established from two different patients are shown as examples.

Gene expression analysis of the cultured cells confirmed maintenance of early germline markers (FIG. 6g). Several oocyte-specific markers were also detected in these cultures. Levels of mRNA were assessed by RT-PCR using a SuperScript® VILO™ cDNA Synthesis Kit (Invitrogen, Life Technologies Corp., Carlsbad, Calif.) and Platinum Taq polymerase (Invitrogen, Life Technologies Corp., Carlsbad, Calif.). All products were sequenced to confiui identity. Sequences of forward and reverse primers used, along with GenBank accession numbers of the corresponding genes, are provided in Table 1 (mouse) and Table 2 (human).

TABLE 1

PCR primers used to analyze gene expression in mouse cell and tissue samples.

| Gene | Accession No. | Primer Sequences (5' to 3'; F, forward; R, reverse) | SEQ ID NO | Size (bp) |
|---|---|---|---|---|
| Blimp1 | NM_007548 | F: CGGAAAGCAACCCAAAGCAATAC | 2 | 483 |
|  |  | R: CCTCGGAACCATAGGAAACATTC | 3 |  |
| Stella | NM_139218 | F: CCCAATGAAGGACCCTGAAAC | 4 | 354 |
|  |  | R: AATGGCTCACTGTCCCGTTCA | 5 |  |
| Fragilis | NM_025378 | F: GTTATCACCATTGTTAGTGTCATC | 6 | 151 |
|  |  | R: AATGAGTGTTACACCTGCGTG | 7 |  |
| Tert | NM_009354 | F: TGCCAATATGATCAGGCACTCG | 8 | 305 |
|  |  | R: ACTGCGTATAGCACCTGTCACC | 9 |  |
| Vasa | NM_0011458 | F: GGAAACCAGCAGCAAGTGAT | 10 | 213 |
|  |  | R: TGGAGTCCTCATCCTCTGG | 11 |  |
| Dazl | NM_010021 | F: GTGTGTCGAAGGGCTATGGAT | 12 | 328 |
|  |  | R: ACAGGCAGCTGATATCCAGTG | 13 |  |
| Msy2 | NM_016875 | F: CCTCCCCACTTTCCCATAAT | 14 | 235 |
|  |  | R: AATGGGTGGGGAAGAAAAAC | 15 |  |
| Sycp3 | NM_011517 | F: AGCAGAGAGCTTGGTCGGG | 16 | 100 |
|  |  | R: TCCGGTGAGCTGTCGCTGTC | 17 |  |
| mc1 | NM_010059. | F: CTCACGCTTCCACAACAAGA | 18 | 81 |
|  |  | R: TCTCGGGGCTGTCATAAATC | 19 |  |
| Nobox | NM_130869 | F: CCCTTCAGTCACAGTTTCCGT | 20 | 379 |
|  |  | R: GTCTCTACTCTAGTGCCTTCG | 21 |  |
| Lhx8 | NM_010713 | F: CGTCAGTCCCAACCATTCTT | 22 | 157 |
|  |  | R: TTGTTGGTGAGCATCCATGT | 23 |  |
| Gdf9 | NM_008110 | F: TGCCTCCTTCCCTCATCTTG | 24 | 709 |
|  |  | R: CACTTCCCCCGCTCACACAG | 25 |  |
| Zp1 | NM_009580 | F: GTCCGACTCCTGCAGAGAAC | 26 | 208 |
|  |  | R: TGATGGTGAAGCGCTGATAG | 27 |  |
| Zp2 | NM_011775 | F: AAGGTCTTGAGCAGGAACGA | 28 | 152 |
|  |  | R: GGGTGGAAAGTAGTGCGGTA | 29 |  |
| Zp3 | NM_011776 | F: CCGAGCTGTGCAATTCCCAGA | 30 | 183 |
|  |  | R: AACCCTCTGAGCCAAGGGTGA | 31 |  |
| B-actin | NM_007393 | F: GATGACGATATCGCTGCGCTG | 32 | 440 |
|  |  | R: GTACGACCAGAGGCATACAGG | 33 |  |

TABLE 2

PCR primers used to analyze gene expression in human cell and tissue samples.

| Gene | Accession No. | Primer Sequences (5' to 3'; F, forward; R, reverse) | SEQ ID NO | Size (bp) |
|---|---|---|---|---|
| Blimp1 | NM_001198 | F: | 34 | 332 |
|  |  | R: | 35 |  |
| Stella | NM_199286 | F: | 36 | 276 |
|  |  | R: | 37 |  |
| Fragilis | NM_021034 | F: ATGTCGTCTGGTCCCTGTTC | 38 | 205 |
|  |  | R: GGGATGACGATGAGCAGAAT | 39 |  |

TABLE 2-continued

PCR primers used to analyze gene expression in human cell and tissue samples.

| Gene | Accession No. | Primer Sequences (5' to 3'; F, forward; R, reverse) | SEQ ID NO | Size (bp) |
|---|---|---|---|---|
| Tert | NM_198253 | F: | 40 | 271 |
|  |  | R: | 41 |  |
| Vasa | NM_024415 | F: | 42 | 283 |
|  |  | R: | 43 |  |
| Dazl | NM_0011908 | F: | 44 | 260 |
|  |  | R: | 45 |  |
| Msy2 | NM_015982 | F: ACCCTACCCAGTACCCTGCT | 46 | 248 |
|  |  | R: GCAAGAAAAGCAACCAGGAG | 47 |  |
| Sycp3 | NM_0011779 | F: TATGGTGTCCTCCGGAAAAA | 48 | 238 |
|  |  | R: AACTCCAACTCCTTCCAGCA | 49 |  |
| Nobox | NM_0010804 | F: | 50 | 375 |
|  |  | R: | 51 |  |
| Lhx8 | NM_0010019 | F: CAAGCACAATTTGCTCAGGA | 52 | 230 |
|  |  | R: GGCACGTAGGCAGAATAAGC | 53 |  |
| Gdf9 | NM_005260 | F: TCACCTCTACAACACTGTTCGGCT | 54 | 344 |
|  |  | R: | 55 |  |
| Zp1 | NM_207341 | F: CGCCATGTTCTCTGTCTCAA | 56 | 219 |
|  |  | R: CGTTTGTTCACATCCCAGTG | 57 |  |
| Zp2 | NM_003460 | F: TCTTCTTCGCCCTTGTGACT | 58 | 217 |
|  |  | R: CTCAGGGTGAGCTTTTCTGG | 59 |  |
| Zp3 | NM_0011103 | F: | 60 | 274 |
|  |  | R: AAGCCCACTGCTCTACTTCATGGT | 61 |  |
| B-actin | NM_001101 | F: CATGTACGTTGCTATCCAGGC | 62 | 250 |
|  |  | R: CTCCTTAATGTCACGCACGAT | 63 |  |

To extend the mRNA analyses of Blimp1, Stella and Fragilis, immunofluorescence analysis of these three classic primitive germline markers was performed (Saitou et al., Nature 2002 418:293-300; Ohinata et al., Nature 2005 436: 207-213). For analysis of cultured OSCs, cells were washed with 1×-concentrated phosphate-buffered saline (PBS), fixed in 2% PFA for 45 minutes at 20° C., washed 3 times with PBS-T (PBS containing 0.01% Triton-X100) and incubated for 1 hour at 20° C. in blocking buffer (PBS containing 2% normal goat serum and 2% BSA). The cells were then incubated for 1 hour at 20° C. with a 1:100 dilution of one of the following primary antibodies: a biotinylated mouse monoclonal against BLIMP1 (ab81961, Abcam, Cambridge, Mass.), a rabbit polyclonal against STELLA (ab19878; Abcam, Cambridge, Mass.) or a rabbit polyclonal against FRAGILIS (mouse: ab15592, human: ab74699; Abcam, Cambridge, Mass.). Cells were washed and incubated for 30 minutes at 20° C. with a 1:500 dilution of streptavidin-conjugated Alexa Fluor 488 (Invitrogen, Life Technologies Corp., Carlsbad, Calif.; BLIMP1 detection) or goat anti-rabbit IgG conjugated to Alexa Fluor 488 (STELLA and FRAGILIS detection) in the presence of rhodamine-phalloidin (Invitrogen, Life Technologies Corp., Carlsbad, Calif.). Cells were washed, incubated with 4′,6-diamidino-2-phenylindole dihydrochloride (DAPI; Sigma-Aldrich, St. Louis, Mo.) and washed 3 additional times before imaging. No signal was detected if primary antibody was omitted or replaced with normal serum (not shown).

For assessment of oocytes generated in vitro by mouse and human OSCs, individual oocytes were collected from culture supernatants, washed, fixed with 2% PFA containing 0.5% BSA for 45 minutes at 37° C., washed and blocked for 1 hour at 20° C. in PBS containing 0.5% BSA and either 5% normal goat serum (VASA or LHX8 detection) or 1% normal donkey serum (c-KIT detection). After blocking, oocytes were incubated for 2 hours at 20° C. with a 1:100 dilution (in PBS with 0.5% BSA) of one of the following primary antibodies: a goat polyclonal against c-KIT (sc1494, Santa Cruz Biotechnology, Inc., Santa Cruz, Calif.), a rabbit polyclonal against VASA (ab13840, Abcam, Cambridge, Mass.) or a rabbit polyclonal against LHX8 (ab41519, Abcam, Cambridge, Mass.). Cells were then washed and incubated with a 1:250 dilution of goat anti-rabbit IgG conjugated to Alexa Fluor 568 (Invitrogen, Life Technologies Corp., Carlsbad, Calif.; VASA detection) or Alexa Fluor 488 (LHX8 detection), or a 1:250 dilution of donkey anti-goat IgG conjugated to Alexa Fluor 488 (c-KIT detection). Cells were washed, incubated with DAPI and washed 3 additional times before imaging. No signal was detected if primary antibody was omitted or replaced with normal serum.

For these latter experiments, detection of oocyte-specific expression of VASA, c-KIT and, for human ovaries, LHX8 in ovarian tissue sections served as a positive control. Mouse and human ovarian tissue was fixed in 4% PFA, paraffin-embedded and sectioned (6-µm) prior to high temperature antigen retrieval using 0.01 M sodium citrate buffer (pH 6.0). After cooling, sections were washed and blocked for 1 hour at 20° C. using TNK buffer (0.1 M Tris-HCl, 0.55 M NaCl, 0.1 mM KCL, 0.5% BSA, and 0.1% Triton-X100 in phosphate-buffered saline) containing either 1% normal goat serum (VASA-COOH or LHX8 detection) or 1% normal donkey serum (VASA-NH$_2$ or c-KIT detection). Sections were then incubated with a 1:100 dilution of primary antibody (in TNK buffer with 1% normal serum) overnight at 4° C., washed in PBS, and incubated for 30 minutes at 20° C. with a 1:500 dilution of goat anti-rabbit IgG conjugated to Alexa Fluor 568 (VASA-COOH detection in human ovary), goat anti-rabbit IgG conjugated to Alexa Fluor 488 (detection of VASA-COOH in mouse ovary or LHX8) or donkey anti-goat IgG conjugated to Alexa Fluor 488 (c-KIT or VASA-NH$_2$ detection). After washing with PBS, sections were cover-slipped using Vectashield containing DAPI (Vector Labs). No signal was detected if primary antibody was omitted or replaced with normal serum.

Figure 6H:
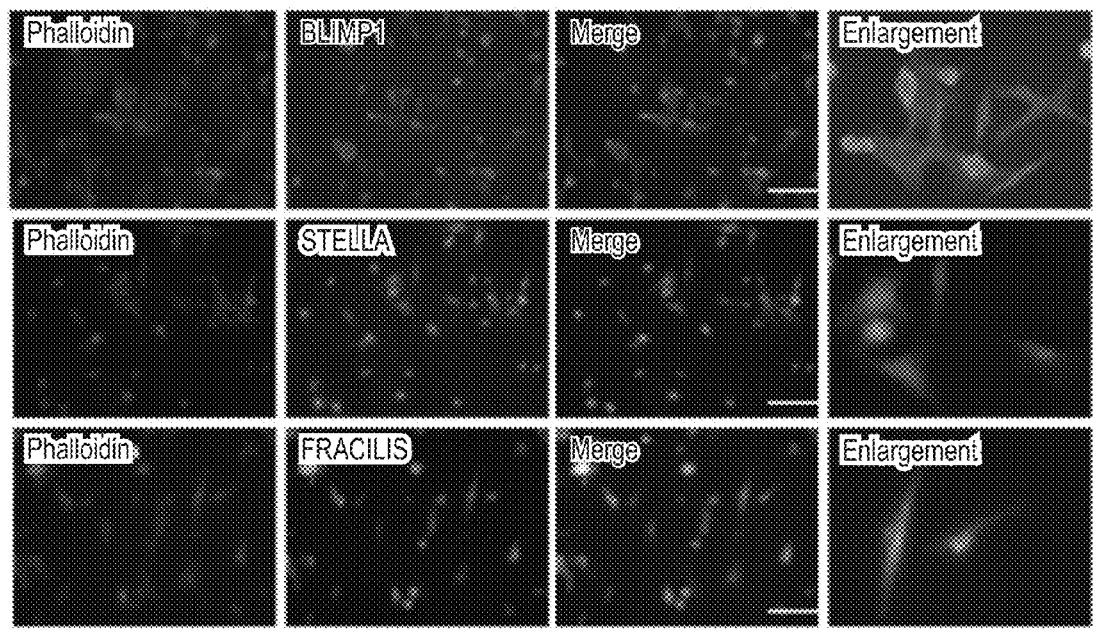
FIGS. 6h and 6i show representative immunofluorescence analysis of BLIMP1, STELLA and FRAGILIS expression in mouse (h) and human (i) OSCs in MEF-free cultures. Cells were counterstained with DAPI and rhodamine-phalloidin to visualize nuclear DNA and cytoplasmic F-actin, respectively.
Figure 6I:
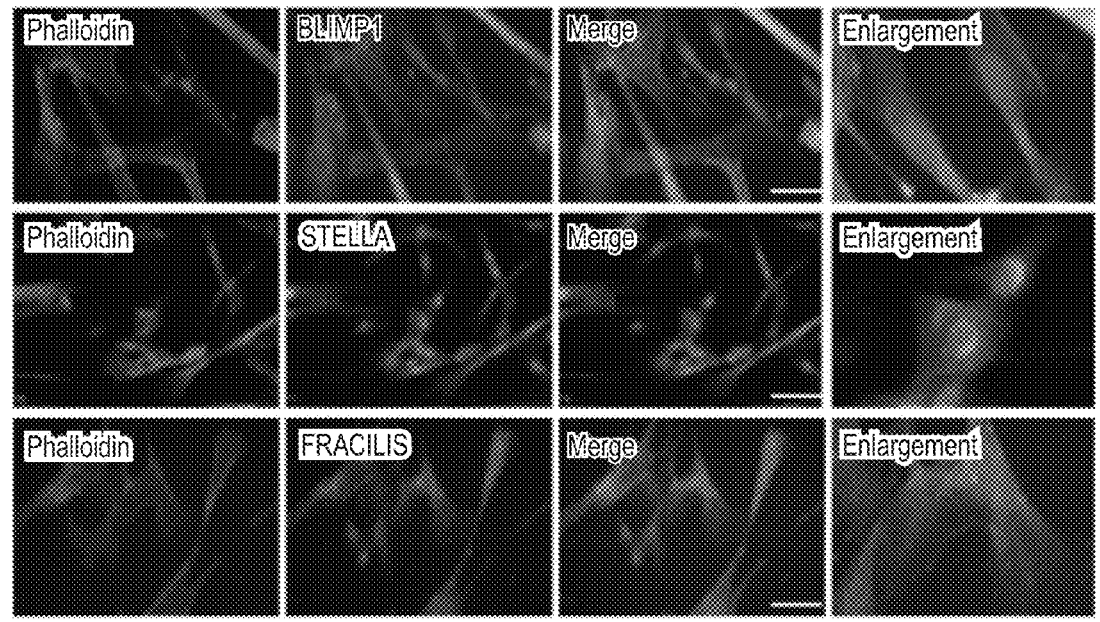

All three proteins were easily and uniformly detected in mouse (FIG. 6h) and human (FIG. 6i) OSCs maintained in vitro. Notably, detection of FRAGILIS in these cells agrees with a recent study reporting that this protein can also be used to isolate OSCs from mouse ovaries by immunomagnetic bead sorting (Zou et al., Stem Cells Dev. 2011 doi: 10.1089/scd.2011.0091).

Example 5

In Vitro Oogenic Capacity of Candidate Human OSCs

Figure 7A:
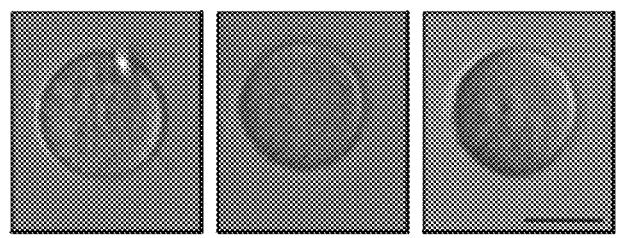
FIGS. 7a through 7c provide examples of immature oocytes formed by mouse OSCs in culture, as assessed by morphology (7*a*), expression of oocyte marker proteins VASA and KIT (7*b*; note cytoplasmic localization of VASA), and the presence of mRNAs encoding the oocyte marker genes Vasa, Kit, Msy2 (also referred to as Y box protein 2 or Ybx2), Nobox, Lhx8, Gdf9, Zp1, Zp2 and Zp3 (7*c*; No RT: PCR of RNA sample without reverse transcription; (β-actin, sample loading control). Scale bars, 25 µm.
Figure 7B:
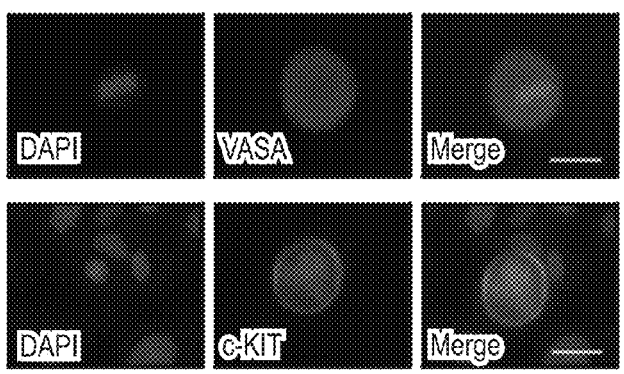
Figure 7C:
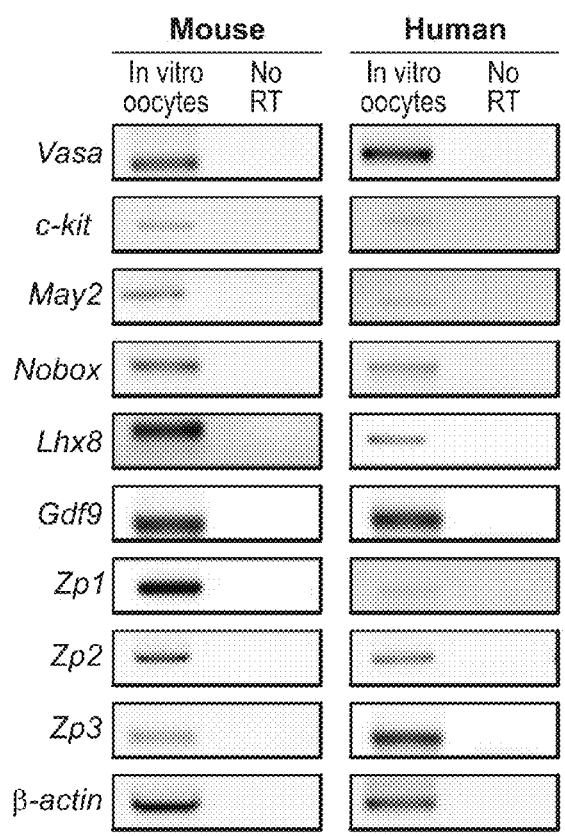

Consistent with results from others (Pacchiarotti et al., Differentiation 2010 79:159-170), mouse OSCs cultured in vitro spontaneously generated large (35-50 µm in diameter) spherical cells that by morphology (FIG. 7a) and gene expression analysis (FIG. 7b, c) resembled oocytes. Peak levels of in vitro oogenesis from mouse OSCs were observed within 24-48 hours after each passage (FIG. 7d), followed by a progressive decline to nearly non-detectable levels each time OSCs regained confluence. Parallel analysis of VASA-positive cells isolated from adult human ovaries and maintained in vitro revealed that these cells, like mouse OSCs, also spontaneously generated oocytes as deduced from both morphological (FIG. 7f) and gene expression (FIG. 7c, g) analyses. The kinetics of in vitro oogenesis from human OSCs differed slightly from mouse OSCs in that peak levels of oocyte formation were observed at 72 hours after each passage (FIG. 7e). In addition to detection of many widely accepted oocyte markers (Vasa, c-Kit, Nobox, Lhx8, Gdf9, Zp1, Zp2, Zp3;

(Suzumori et al., *Mech. Dev.* 2002 111:137-141; Rajkovic et al., *Science* 2004 305:1157-1159; Pangas et al., *Proc. Natl. Acad. Sci. USA* 2006 103:8090-8095; Elvin et al., *Mol. Endocrinol.* 1999 13:1035-1048; Zheng et al., *Semin. Reprod. Med.* 2007 25:243-251), mouse and human OSC-derived oocytes also expressed the diplotene oocyte stage-specific marker Msy2 (FIG. 7*c*). MSY2 is a mammalian homologue of Xenopus FRGY2, a germ cell-specific nucleic acid-binding Y-box protein that is essential for meiotic progression and gametogenesis in both sexes (Gu et al., *Biol. Reprod.* 1998 59:1266-1274; Yang et al., *Proc. Natl. Acad. Sci. USA* 2005 102:5755-5760). Through empirical testing of commercially-available antibodies using adult human ovarian cortical tissue as a positive control, four such antibodies against oocyte markers were identified that specifically reacted with immature oocytes present in adult human ovaries (VASA, c-KIT, MSY2, LHX8; FIG. 8); all four of these proteins were also detected in oocytes generated by human OSCs in vitro (FIG. 7*g*).

Figure 7H:
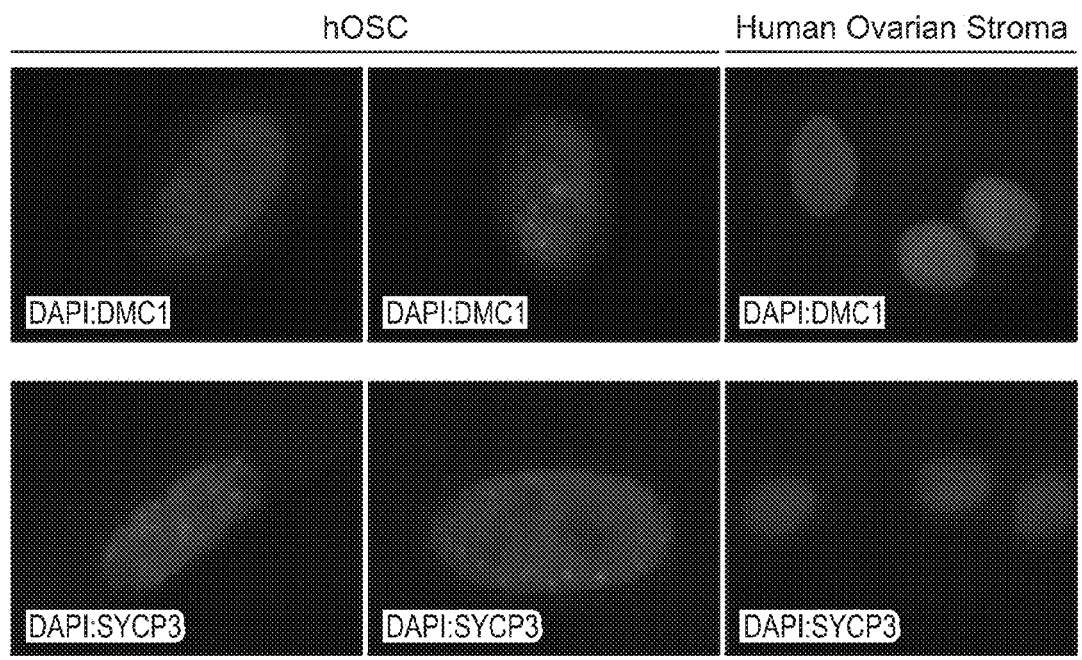
In FIG. 7*h*, immunofluorescence-based detection of the meiotic recombination markers, DMC1 (dosage suppressor of mckl homolog) and SYCP3 (synaptonemal complex protein 3) (DAPI counterstain), is shown in nuclei of cultured human OSCs; human ovarian stromal cells served as a negative control.

The presence of mRNA encoding the meiotic marker MSY2 in oocytes newly formed from human OSCs in vitro prompted us to next explore the prospects of meiotic entry in these cultures. Immunofluorescence analysis of attached (non-oocyte germline) cells 72 hours after passage identified cells with punctate nuclear localization of the meiosis-specific DNA recombinase, DMC1, and the meiotic recombination protein, synaptonemal complex protein 3 (SYCP3) (FIG. 7*h*). Both proteins are specific to germ cells and are necessary for meiotic recombination (Page et al., Annu. Rev. *Cell Dev. Biol.* 2004 20:525-558; Yuan et al., *Science* 2002 296:1115-1118; Kagawa et al., *FEBS J.* 2010 277:590-598).

Figure 7I:
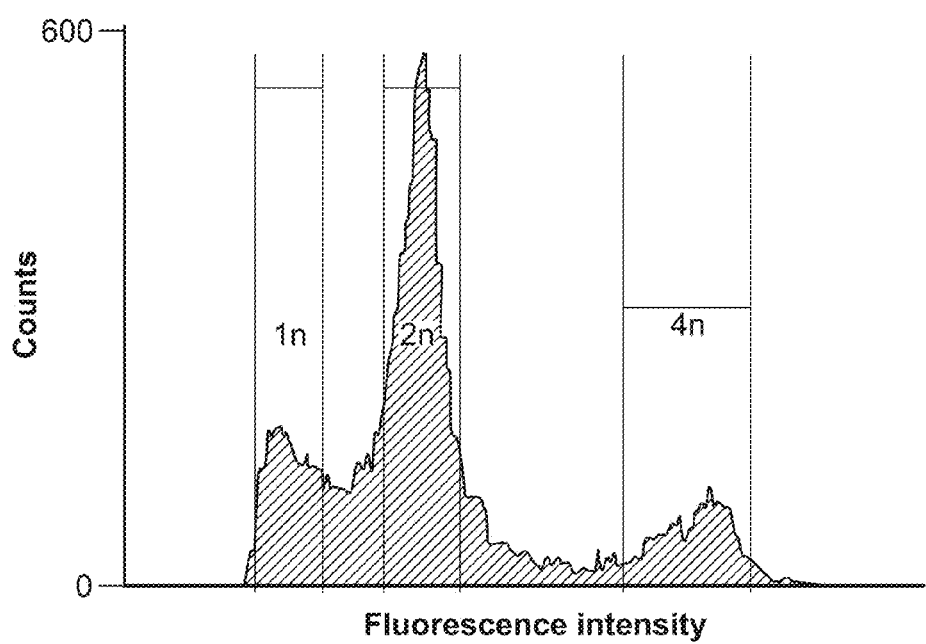
In FIG. 7*i*, FACS-based ploidy analysis of cultured human OSCs is shown 72 hours after passage. Results from ploidy analysis of cultured human fibroblasts (negative control) and cultured mouse OSCs are presented in FIG. 9.
Figure 8A:
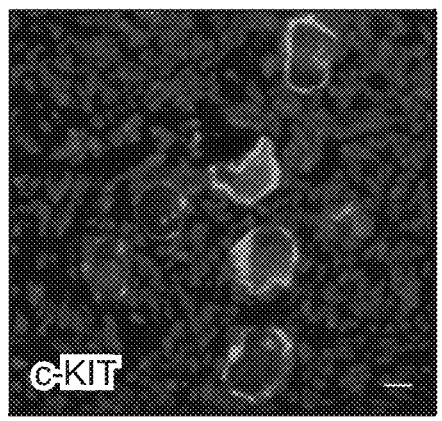
FIG. 8 depicts the detection of oocyte-specific markers in adult human ovaries. Immunofluorescence analysis of VASA (8*a*), KIT (8*b*), MSY2 (8*c*) and LHX8 (8*d*) expression in oocytes in adult human ovarian cortical tissue is shown (see also FIG. 10*h*). Sections were counterstained with DAPI for visualization of nuclei. Scale bars, 25 µm.
Figure 8B:
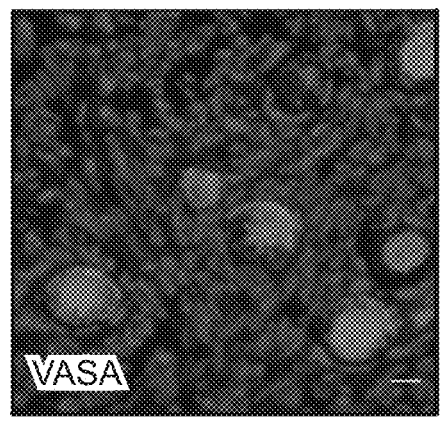
Figure 8C:
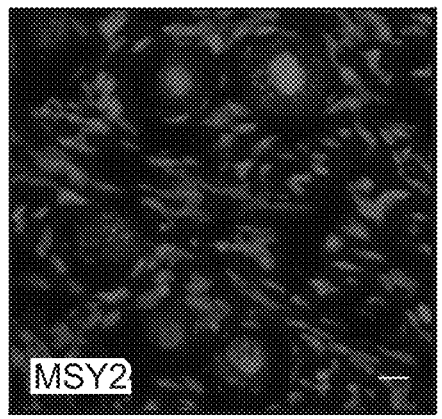
Figure 8D:
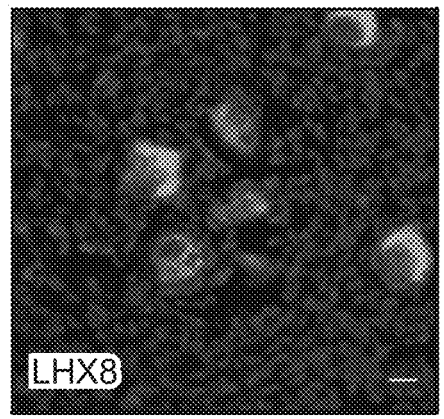
Figure 9A:
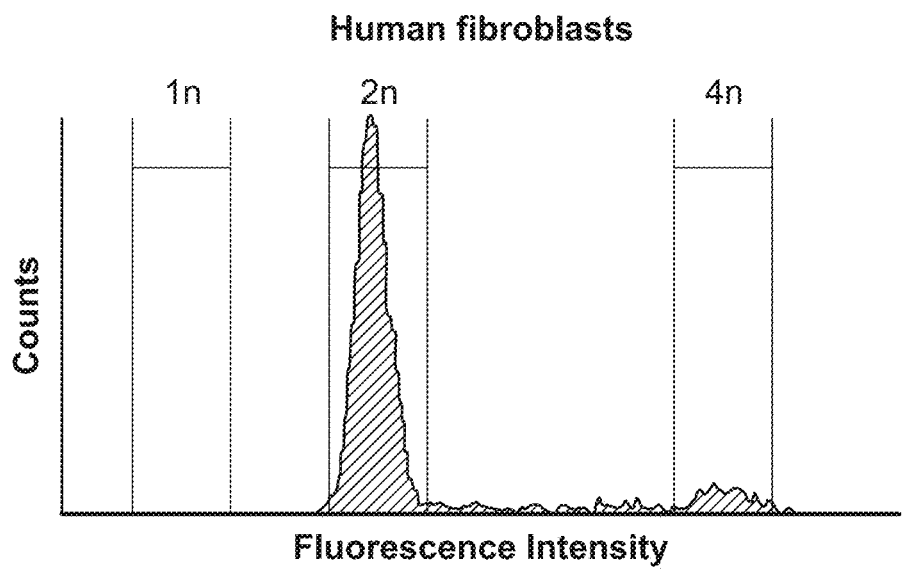
FIGS. 9*a* and 9*b* show representative FACS-based assessment of ploidy status in cultures of actively-dividing human fetal kidney fibroblasts (9*a*) and in mouse OSCs collected 48 hours after passage (9*b*). Haploid (1n) cells were only detected in the gemline cultures, consistent with results from analysis of human OSCs maintained in vitro (see FIG. 7*i*), whereas all cultures contained diploid (2n) and tetraploid (4n) populations of cells.
Figure 9B:
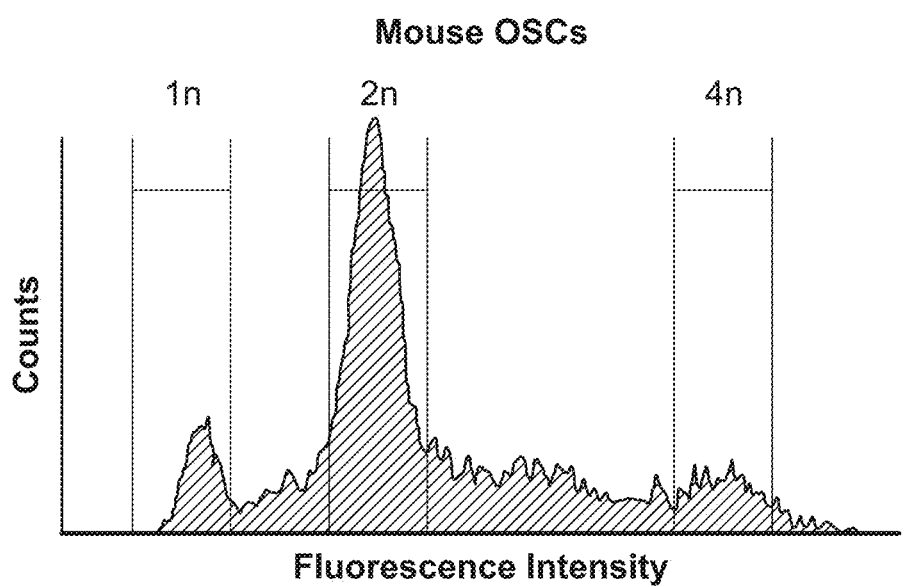

Chromosomal DNA content analysis of human OSC cultures 72 hours after passage was determined. Cultured mouse (48 hours after passage) or human (72 hours after passage) OSCs were collected by trypsinization, washed and resuspended in ice-cold PBS, and counted with a hemocytometer. After fixation in ice-cold 70% ethanol for 1 hour, cells were washed in ice-cold PBS and incubated with 0.2 mg/ml RNase-A for 1 hour at 37° C. Propidium iodide was then added (10 µg/ml final), and ploidy status was determined using the BD Biosciences FACSAria II cytometer. As a control somatic cell line, these experiments were repeated using human fetal kidney fibroblasts (HEK 293, Invitrogen, Life Technologies Corp., Carlsbad, Calif.). This analysis revealed the presence of an expected diploid (2n) cell population; however, peaks corresponding to 4n and 1n populations of cells were detected, the latter being indicative of germ cells that had reached haploid status (West et al., *Stem Cells Dev.* 2011 20:1079-1088) (FIG. 7*i*). In actively-dividing cultures of fetal human kidney fibroblasts analyzed as controls in parallel, only 2n and 4n populations of cells (FIG. 9*a*) were detected. Comparable outcomes were observed following FACS-based chromosomal analysis of mouse OSC cultures (FIG. 9*b*).

Example 6

Human OSCs Generate Oocytes in Human Ovarian Cortical Tissue In Vivo

To confirm and extend the in vitro observations of putative oogenesis from candidate human OSCs, in two final experiments VASA-positive cells isolated from adult human ovaries were stably transduced with a GFP expression vector (GFP-hOSCs) to facilitate cell tracking. For cell tracking experiments, human OSCs were transduced using a retrovirus to obtain cells with stable expression of GFP (GFP-hOSCs). Briefly, 1 µg of pBabe-Gfp vector DNA (Addgene plasmid repository #10668) was transfected as per the manufacturer's protocol (Lipofectamine, Invitrogen, Life Technologies Corp., Carlsbad, Calif.) into the Platinum-A retroviral packaging cell line (Cell Biolabs, Inc., San Diego, Calif.). Viral supernatant was collected 48 hours after transfection. Transduction of human OSCs was performed using fresh viral supernatant facilitated by the presence of polybrene (5 µg/ml; Sigma-Aldrich, St. Louis, Mo.). After 48 hours, the virus was removed and replaced with fresh OSC culture medium. Human OSCs with expression of GFP were purified or isolated by FACS following an initial 1 week of expansion, and the purified or isolated cells were expanded for additional 2 weeks before a second round of FACS purification or sorting to obttain GFP-hOSCs for human ovarian tissue re-aggregation or xenografting experiments.

In the first experiment, approximately $1 \times 10^5$ GFP-hOSCs were then re-aggregated with dispersed adult human ovarian cortical tissue. Human ovarian cortex was dissociated and washed as described above, and incubated with 35 µg/ml phytohemaglutarmin (PHA; Sigma, St. Louis, Mo.) plus $1 \times 10^5$ GFP-hOSCs for 10 minutes at 37° C. The cell mix was pelleted by centrifugation (9,300×g for 1 minute at 20° C.) to create the tissue aggregate, which was placed onto a Millicell 0.4 µm culture plate insert (EMD Millipore, Inc., Billerica, Mass.) contained in a 6-well culture dish with 1 ml of OSC culture medium. Aggregates were incubated at 37° C. in 5% $CO_2$-95% air, and live-cell GFP imaging was performed 24, 48 and 72 hours later.

Figure 10A:
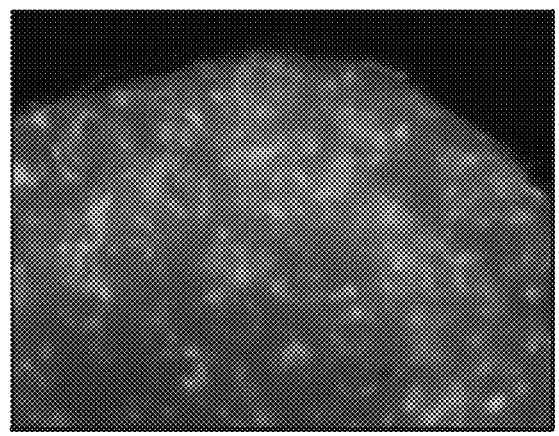
Figure 10B:
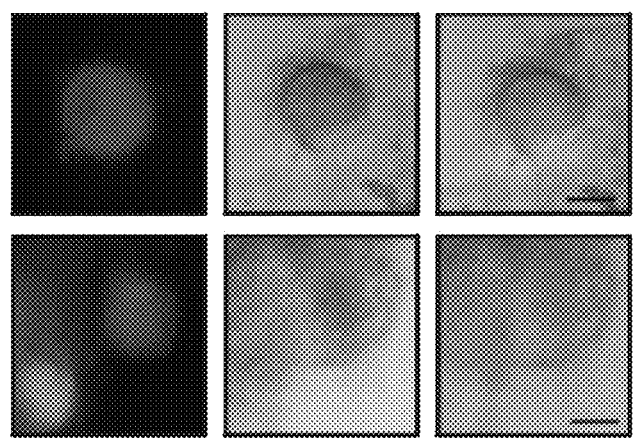
Figure 10C:
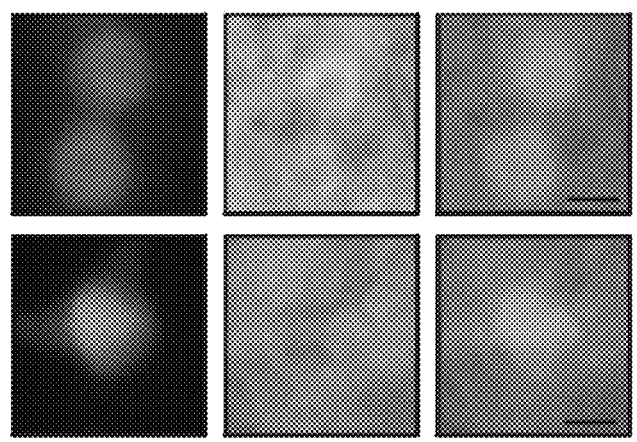

Numerous GFP-positive cells were observed, as expected, throughout the re-aggregated tissue (FIG. 10*a*). The aggregates were then placed in culture and assessed 24-72 hours later by direct (live cell) GFP fluorescence. Within 24 hours, several very large (≥50-µm) single cells were also observed in the aggregates, many of which were enclosed by smaller GFP-negative cells in tightly compact structures resembling follicles; these structures remained detectable through 72 hours (FIG. 10*b*, *c*). These findings indicated that GFP-expressing human OSCs spontaneously generated oocytes that became enclosed by somatic (pregranulosa/granulosa) cells present in the adult human ovarian dispersates.

Next, GFP-hOSCs were injected into adult human ovarian cortical tissue biopsies, which were then xenografted into NOD/SCID female mice (n=40 grafts total). Ovarian cortical tissue pieces (2×2×1 mm) were individually injected with approximately $1.3 \times 10^3$ GFP-hOSCs using a 10-µl NanoFil syringe with a 35-gauge beveled needle (World Precision Instruments, Sarasota, Fla.). Recipient NOD/SCID female mice were anesthetized and a small incision was made along the dorsal flank for subcutaneous insertion of the human ovarian tissue, essentially as described (Weissman et al., *Biol. Reprod.* 1999 60:1462-1467; Matikainen et al., *Nature Genet.* 2001 28:355-360). Xenografts were removed after 7 or 14 days post transplantation, fixed in 4% PFA, paraffin-embedded and serially sectioned (6-µm) for immunohistochemical analysis using a mouse monoclonal antibody against GFP (sc9996; Santa Cruz Biotechnology, Santa Cruz, Calif.) (Lee et al., *J. Clin. Oncol.* 2007 25:3198-3204). Briefly, high temperature antigen retrieval was first performed using 0.01 M sodium citrate buffer (pH 6.0). After cooling, sections were incubated for 10 minutes with 3% hydrogen peroxide in methanol to block endogenous peroxidase activity, washed and incubated in streptavidin-biotin pre-block solution as per the manufacturer's protocol (Vector Laboratories, Burlingame, Calif.). Sections were then blocked for 1 hour at 20° C. using TNK buffer containing 1% normal goat serum and incubated overnight at 4° C. with a 1:100 dilution of GFP antibody prepared in TNK buffer containing 1% normal goat serum. Sections were then washed, incubated with a 1:500 dilution of goat anti-mouse biotinylated secondary antibody for 30 minutes at 20° C., washed and reacted with Vectastain ABC reagents (Lab Vision, ThermoFisher Scientific, Inc., Waltham, Mass.) for 30 minutes at 20° C. prior to detection of GFP-positive cells using diaminobenzidine (DAKO Glostrup, Denmark). Sections were lightly counterstained with haematoxylin to visualize cell and tissue architecture. Negative controls (complete immunohistochemical staining protocol on xenografted tissues that received vehicle injections) were always run in parallel and did not show a positive signal. To confirm and extend these observations, dual immunofluorescence-based detection of GFP and either MSY2 (diplotene stage oocyte-specific marker) or LHX8 (early stage oocyte transcription factor) in xenografted human ovarian tissues was performed with DAPI counterstaining, as detailed previously in the description of immunoanalysis.

Figure 10D:
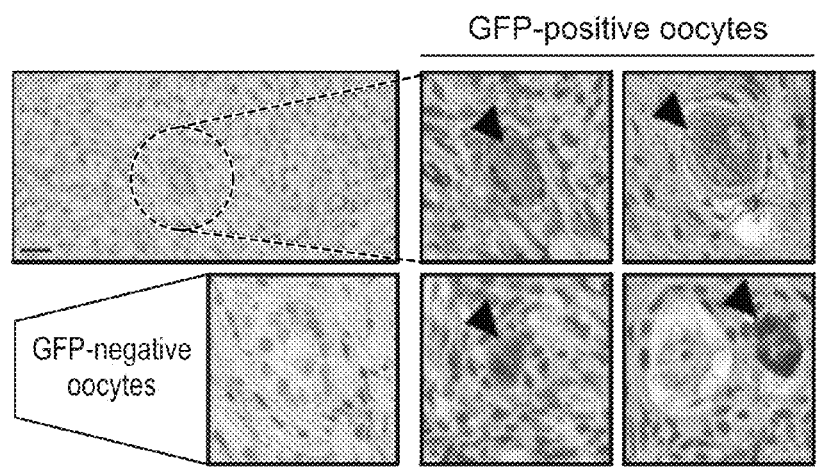
Figure 10E:
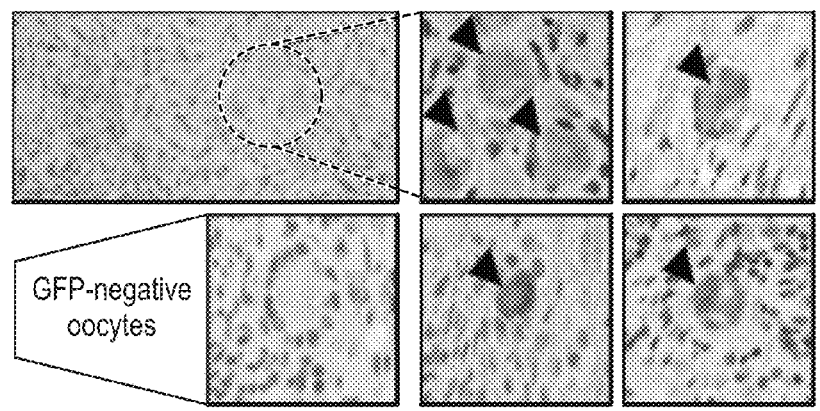
Figures 10F, 10G:
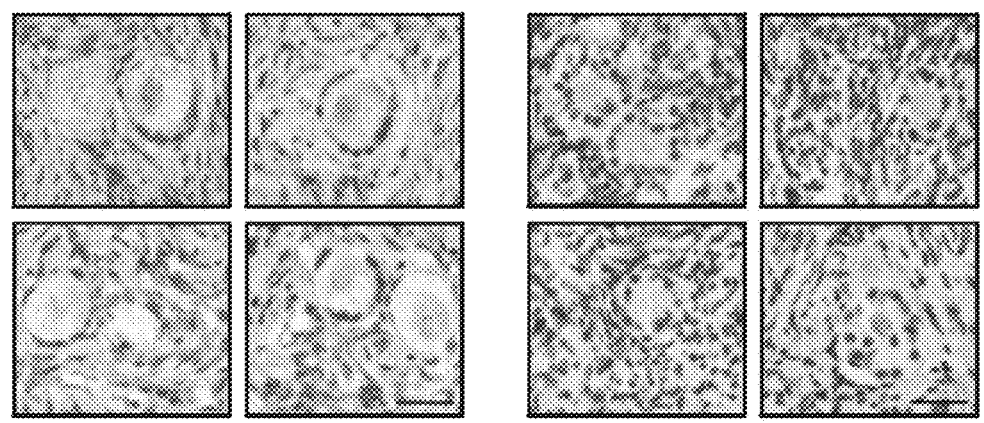
Figure 10H:
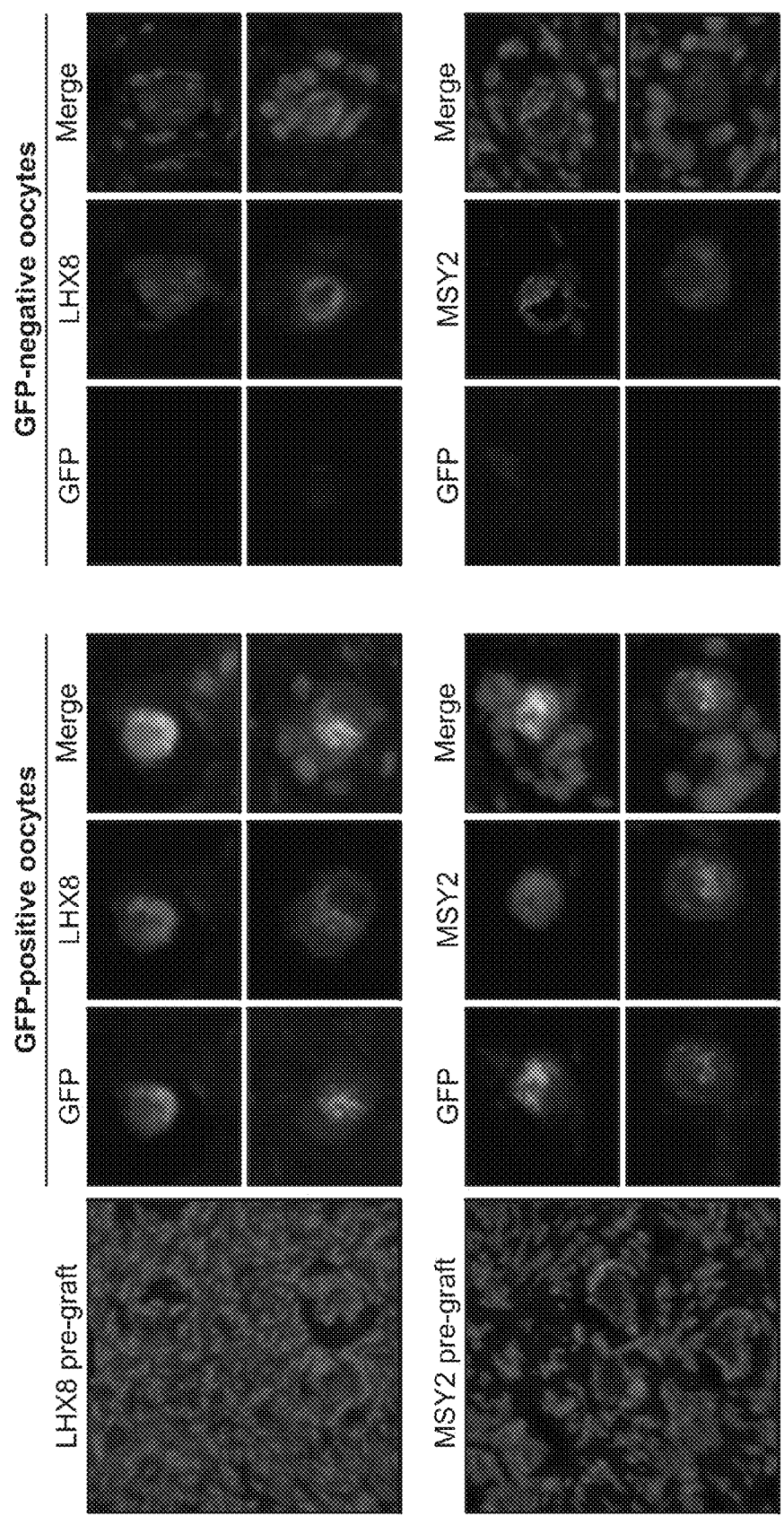
FIG. 10*h* shows dual immunofluorescence analysis of GFP expression and either the diplotene stage oocyte-specific marker MSY2 or the oocyte transcription factor LHX8 in xenografts receiving GFP-hOSC injections. Note that GFP was not detected in grafts prior to GFP-hOSC injection, whereas MSY2 and LHX8 were detected in all oocytes. Sections were counterstained with DAPI for visualization of nuclei. Scale bars, 25 µm.
Figure 11:
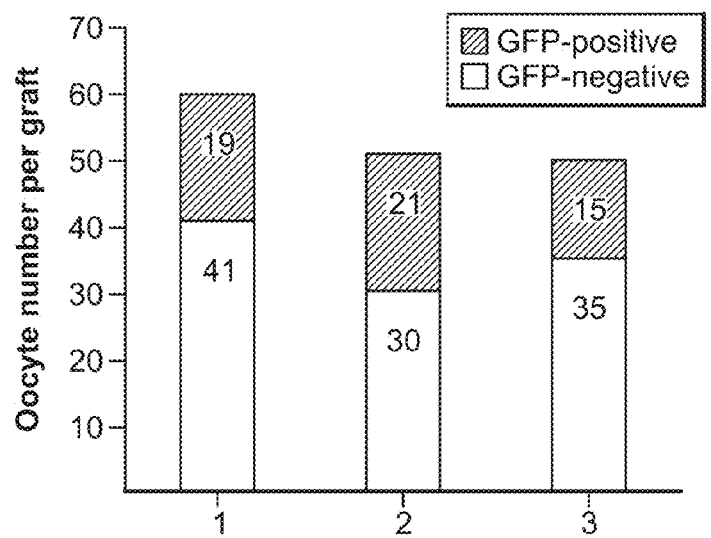
FIG. 11 depicts morphometry-based assessment of oocyte formation in human ovarian xenografts following GFP-hOSC transplantation. The total number of primordial and primary follicles in 3 randomly selected human ovarian cortical tissue samples (labeled 1, 2 and 3) are shown, 7 days after injecting GFP-hOSCs and xenografting into NOD/SCID mice, which contain GFP-negative (host-derived) or GFP-positive (OSC-derived) oocytes (see FIGS. 10*d* through 10*g* for examples).

Grafts were collected 7 or 14 days later for assessment of GFP expression. All human ovary grafts contained easily discernible primordial and primary follicles with centrally-located GFP-negative oocytes. Interdispersed among and often adjacent to these follicles, which were presumably present in the tissue prior to GFP-hOSC injection, were other immature follicles containing GFP-positive oocytes (FIG. 10d, f). Serial section histomorphometric analysis of 3 randomly selected human ovarian tissue biopsies injected with GFP-hOSCs revealed the presence of 15-21 GFP-positive oocytes per graft 7 days after xenografting into mice (FIG. 11). As controls, GFP-positive oocytes were never detected in human ovarian cortical tissue prior to GFP-hOSC injection (FIG. 10e) or in xenografts that received mock injections (vehicle without GFP-hOSCs) prior to transplantation into NOD/SCID mice (FIG. 10g). Dual immunofluorescence-based detection of GFP along with either the diplotene stage oocyte-specific marker MSY2 (Gu et al., Biol. Reprod. 1998 59:1266-1274; Yang et al., Proc. Natl. Acad. Sci. USA 2005 102:5755-5760) or the oocyte-specific transcription factor LHX8 (Pangas et al., Proc. Natl. Acad. Sci. USA 2006 103:8090-8095) identified many dual-positive cells distributed throughout xenografts injected with GFP-hOSCs (FIG. 10h). As expected, no GFP-positive oocytes were detected in ovarian tissue prior to GFP-hOSC injection or in xenografts that did not receive GFP-hOSC injections (not shown; see FIG. 10e, g); however, these oocytes were consistently positive for LHX8 and MSY2 (FIG. 10h; FIG. 8).

Example 7

Use of OSCs in Autologous Germline Mitochondrial Energy Transfer ("AUGMENT")

Figure 13:
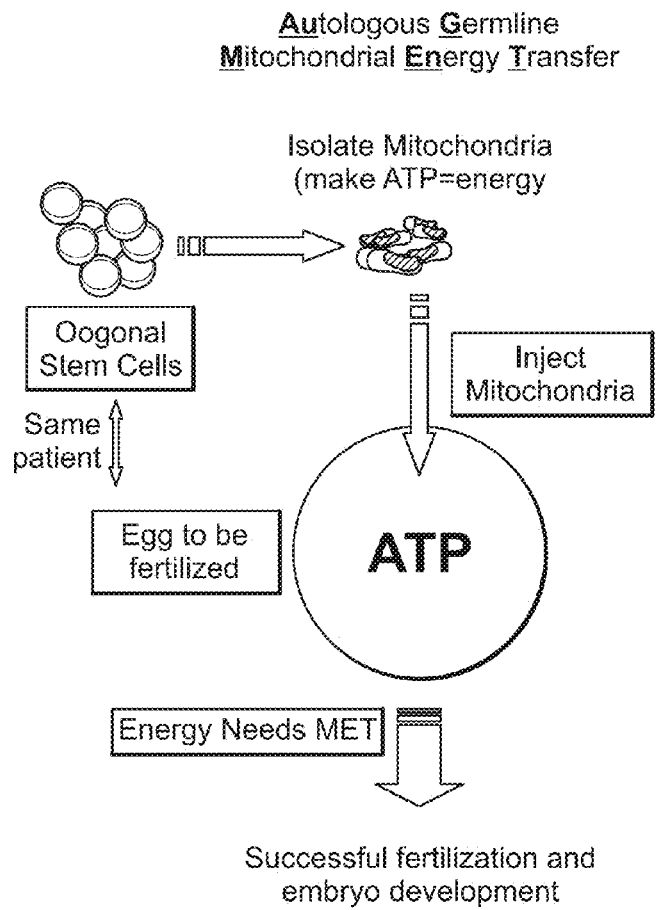
FIG. 13 depicts an overview of an Autologous Germline Mitochondrial Energy Transfer (AUGMENT) procedure. Note that OSCs used as a source of mitochondria for the transfer, and the egg to be fertilized which will receive the OSC mitochondria, are obtained from the same subject.

FIG. 13 depicts an overview of the use of OSCs as an autologous source of female germ cells for derivation of oogenic cytoplasm or mitochondrial fractions that can then be transferred into an oocyte obtained from the same subject prior to or during in vitro fertilization (IVF). The resultant boost in mitochondrial DNA copy number and ATP-generating capacity in the egg after AUGMENT ensures that the oocyte has ample reserves of ATP for energy-driven events required for successful fertilization and embryonic development. The additional mitochondria provided to the oocyte by AUGMENT are derived from the natural precursor cell used by the body to produce oocytes. Furthermore, the additional mitochondria will not produce adverse effects in the oocyte, based on data showing that healthy embryogenesis proceeds even when the minimal threshold number of mitochondria needed for embryo development is exceeded by nearly four-fold (see Wai et al., Biology of Reproduction 2010 83:52-62, FIG. 6). The beneficial effects of heterologous ooplasmic transfer reported earlier by Cohen et al., Mol Hum Reprod 1998 4:269-80, a procedure which is not suitable for human use because it results in germline genetic manipulation and mitochondrial heteroplasmy in embryos/offspring, indicate that oocytes are benefited by additional mitochondria.

An exemplary clinical protocol for AUGMENT is as follows. Prior to the start of standard IVF, the subject will undergo a laparoscopy during menstrual cycle days 1-7 to collect up to three pieces (approximately 3×3×1 mm each) of ovarian epithelium (ovarian cortical biopsy) from one ovary. During this procedure, 2-3 incisions will be made within the abdomen and a device will be inserted to remove the tissue from an ovary using sterile procedures. The tissue collected will be placed in sterile solution and transported on ice to the GTP compliant laboratory where it will be cryopreserved until the time of AUGMENT/ICSI. The tissue will remain frozen until the time of enzymatic dissociation. This will serve as the source of autologous OSCs from which mitochondria will be purified or isolated.

Next, OSCs will be isolated and mitochondria will be harvested from the OSCs. After thawing the ovarian cortical biopsied tissue, the tissue will be minced and placed in solution, containing recombinant collagenase and recombinant DNaseI and homogenized to a single cell suspension. The suspension will be passed through a cell strainer to prepare a solution of single cells. The single cell suspension will be incubated with an anti-VASA antibody. Labeled cells will then be isolated by fluorescence-activated cell sorting (FACS). Standard slow cooling cryopreservation procedures for freezing aliquots of OSCs will be used.

Subjects will undergo a standard IVF protocol including baseline evaluation, GnRH antagonist down-regulation and gonadotropin stimulation. Oocyte retrieval will take place within 34-38 hours after hCG administration and oocytes will be assessed for quality and maturation state. Mature oocytes will be inseminated by ICSI.

On the day of oocyte retrieval, the frozen OSC vial for that subject will be thawed using standard methods. OSCs will be processed to yield a mitochondrial pellet (Frezza et al. Nature Protocols 2007 2:287-295 or Perez et al., Cell Death and Differentiation 2007 3:524-33. Epub 2006 Oct. 13) or as described below in Example 9, where a FACS-based method is employed to isolate the total mitochondrial population in a tissue and optionally, further isolate the actively respiring mitochondrial population or quantitate the ratio of active to total mitochondria in a tissue. Evaluation and activity of the mitochondrial preparation will be assessed and recorded. Exemplary assays of mitochondrial function are described in Example 8. The mitochondrial pellet will be re-suspended in media to a standardized concentration of mitochondrial activity which improves oocyte quality. This media containing the mitochondria will be aspirated into a microinjection needle that contains the spermatozoan to be delivered. Both the mitochondria and spermatozoan will be delivered together into the oocyte by ICSI. Alternatively, the mitochondria or preparation thereof will be frozen prior to use.

Following fertilization and embryo culture, typically a maximum of three, grade 1 or grade 2 (SART grading system (50)) embryos may be transferred under ultrasound guidance after 3 or 5 days of culturing based on the assessment of embryo development. If a pregnancy is confirmed via beta hCG testing, then the subject will have subsequent observations at approximately 6 and 20-weeks gestational age.

Example 8

Figure 14:
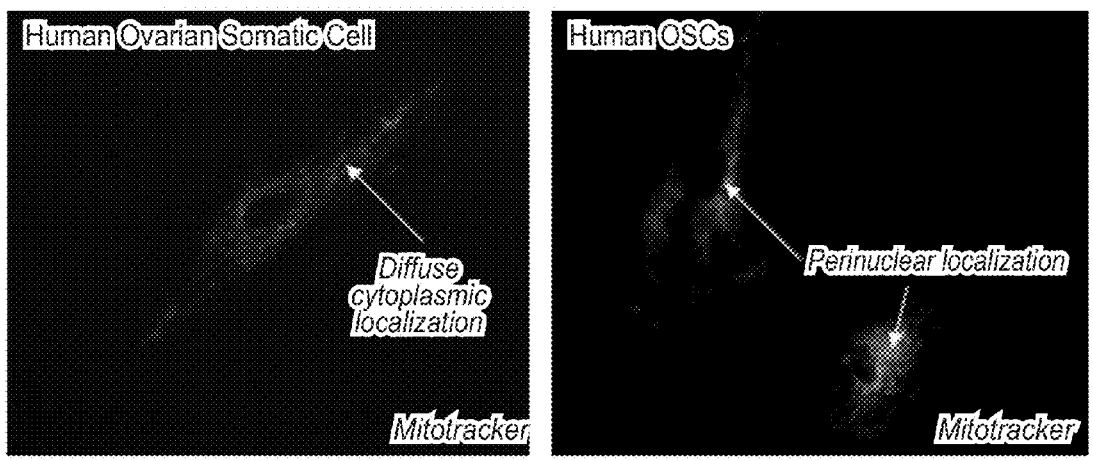
FIG. 14 depicts mitochondrial staining with MitoTracker Green FM (Invitrogen M7514, Life Technologies Corp., Carlsbad, Calif.) in cultured human ovarian somatic cells and cultured human OSCs obtained from the same patient.

Assessment of Mitochondrial Parameters in Human OSCs versus Human Ovarian Stromal Cells Mitochondrial staining was conducted in cultured human ovarian somatic cells and cultured human OSCs obtained from the same patient. Cells were incubated with the non-oxidation dependent MitoTracker Green FM (Invitrogen, Life Technologies Corp., Carlsbad, Calif.; M7514) mitochondrial tracking probe, which indicates mitochondrial mass, at 37° C. for 45 minutes and washed twice with fresh culture medium prior to live cell fluorescent imaging. Both cell types were processed in parallel. In FIG. 14, distribution patterns indicate perinuclear localization in the human OSCs, consistent with other human stem cell types.

Accumulation of a common deletion mutation (deletion of nucleotides 8470-13447 of the mitochondrion genome) occurs in mtDNA of cells as an organism ages. PCR primers were designed to span this deletion. If the deletion mutation is absent, indicating the mtDNA genome is intact, the PCR amplicon will be 5080 bp. If the deletion is present, a 103 bp fragment will be amplified. In instances of heterogeneity among the mitochondria within individual cells or the cell population, both products do not amplify. This occurs because because the deletion (as indicated by the small band) amplifies much more efficiently than the large 5-kb product. The small product reaches the exponential and plateau phases more rapidly, thereby utilizing the available reagents in the PCR mix and leaving little or none for the less efficient 5-kb product amplification. The PCR analysis shown in FIG. 15 indicates that the human OSCs do not harbor an accumulation of the mutation, whereas patient matched ovarian somatic cells do.

To confirm that the mitochondrial population within the somatic cells is heterogeneous with respect to the mutation (some mitochondria will harbor the deletion and some will not), a second set of PCR primers targeting a sequence specifically within the deleted region was used to assess mitochondrial integrity in ovarian somatic cells. The amplification of a 191 bp product indicates that this region is intact within at least some of the mitochondria in these cells, and that the overall population of somatic cell mitochondria is heterogeneous with respect to the deletion mutation, whereas the human OSCs are essentially free of the mutation.

Primer sequences (5' to 3') for mitochondrial DNA analysis include Amplicon 1 for 5080 bp (intact) or 103 bp (deletion mutant) having the following sequences: TTACACTATTC-CTCATCACCCAAC (SEQ ID NO: 64) (forward) and TGT-GAGGAAAGGTATTCCTGCT (SEQ ID NO: 65) (reverse) and Amplicon 2 for 191 bp (internal, deleted sequence) having the following sequences: CCTACCCCTCACAAT-CATGG (SEQ ID NO: 66)(forward) and ATCGGGTGAT-GATAGCCAAG (SEQ ID NO: 67)(reverse).

Figure 16:
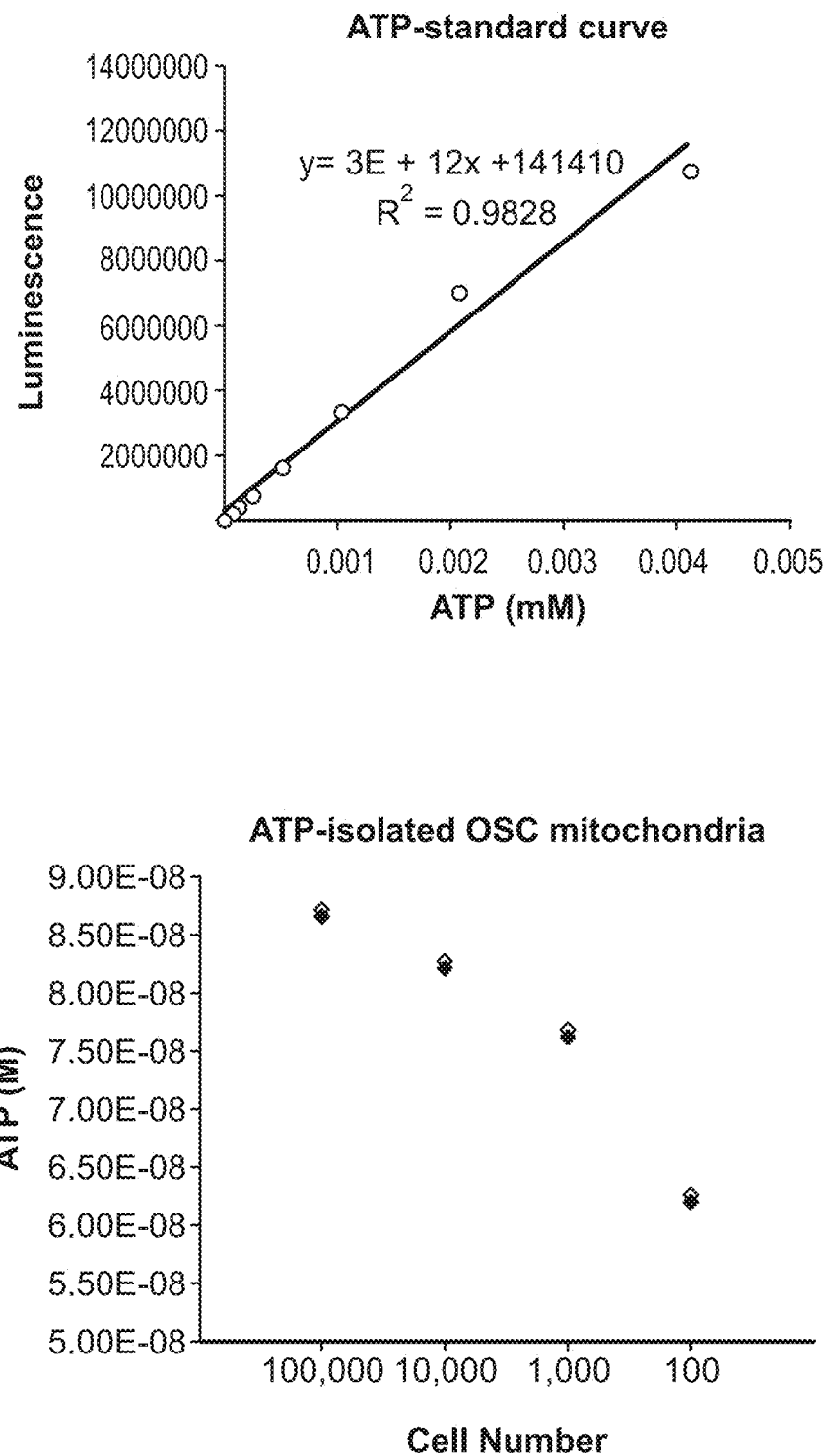
FIG. 16 depicts the results of an ATP assay.

FIG. 16 depicts the results of an ATP assay (ATP bioluminescence Assay Kit HS II, Roche Applied Science, Mannheim, Germany). The left panel shows the standard curve following dilution of ATP (molar ratio vs. chemiluminescence). As shown, the assay is sensitive in detecting levels of ATP. The right panel shows the amount of ATP from mitochondria isolated from cultured human OSCs. Approximately 100,000, 10,000, 1,000, and 100 cells were lysed and used for analysis, with values and detectability falling in the mM to fM range. Samples containing as few as 100 OSCs produced as much as 6.00E-08 M ATP (about 600 pmol ATP/cell). Compared to ovarian somatic cells, OSCs produce greater than or equivalent amounts of ATP/cell with approximately 100 fold less mitochondria.

Example 9

FACS-based Isolation of Mitochondria

As described in this Example, FACS-based methods can be employed to isolate the total mitochondrial population in a tissue. In addition, FACS-based methods for mitochondrial isolation can employ dual-labeling using two different fluorescent dyes (mitochondrial membrane potential (MMP)-dependent and MMP-independent) to isolate only the functional (e.g., actively respiring) mitochondrial population or quantitate the ratio of functional to total mitochondria in a tissue, cell, lysed cell or fraction derived thereof.

Figure 19:
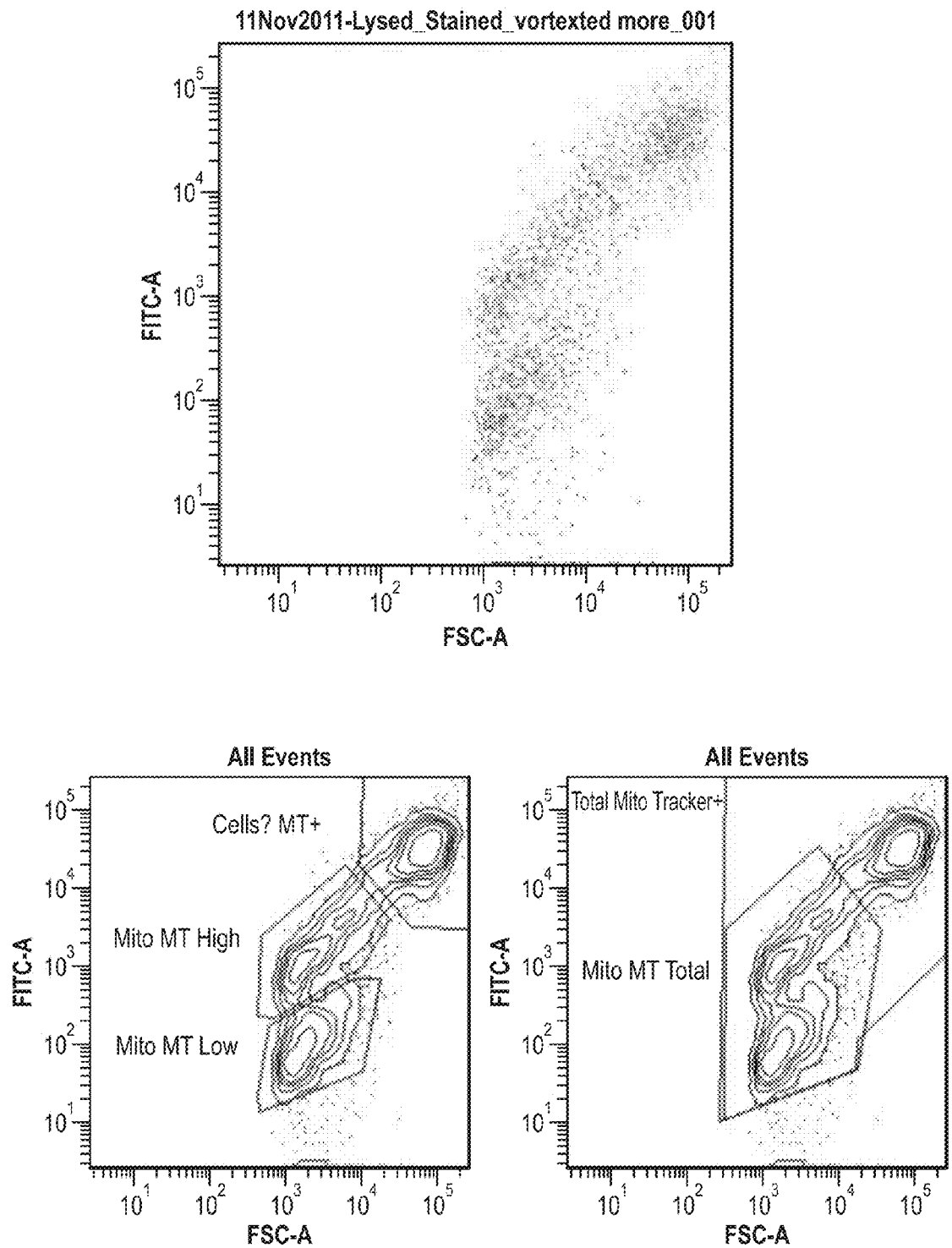
FIG. 19 depicts mitochondria following staining with mitotracker M7514 and cell lysis. Human OSCs were incubated with M7514, and then lysed to release the stained mitochondria using osmotic shock. The entire population (mitochondria from lysed cells and residual unlysed stained cells) was analyzed by FACS. The left panel shows mitochondria from lysed cells, which are easily distinguishable from mitochondria contained in residual unlysed cells based on size (forward scatter; FSC-A). Fluorescence intensity (FITC-A) revealed two distinct populations of mitochondria from lysed cells, one having high intensity (Mito MT high), and one having low intensity (Mito MT Low). Functional mitochondria are known to have a greater uptake and retention of the stain, and thus fluoresce at a higher intensity (Invitrogen technical staff, Life Technologies Corp., Carlsbad, Calif.).

The non-oxidation dependent MitoTracker Green FM (Invitrogen, Life Technologies Corp., Carlsbad, Calif.; M7514) mitochondrial tracking probe, which indicates mitochondrial mass, was prepared and utilized as described below. MitoTracker stock solution (1-5 mg/ml dissolved in anhydrous dimethylsulfoxide (DMSO)) was diluted in serum free growth medium to reach a working concentration of between 25-500 nM. Freshly isolated or thawed OSCs were pelleted by centrifugation at 300×g for 5 minutes. The supernatant was aspirated and the cell pellet was resuspended in 200 µl of the diluted MitoTracker stock solution. Cells were incubated at 37° C. for 45 minutes, washed in pre-warmed (37° C.) serum free growth medium and pelleted by centrifugation at 300×g for 5 minutes (alternatively, cells can be lysed prior to incubation with a probe of interest). Supernatant was aspirated and cells were resuspended in 100 µl mitochondrial lysis buffer and transferred to a FACS sort tube for lysis by mechanical permeabilization using rapid osmotic shock. Following lysis, cells were equilibrated on ice for 15-30 minutes, incubated in 200 µl (minimum volume) ice cold PBS and vortexed. As shown in FIG. 19, three distinct populations were observed: residual M7514 positive cells (Cells MT +), high fluorescent mitochondria (functional, Mito MT high), and low expressing mitochondria (non-functional, Mito MT Low). The ratio of functional to non-functional mitochondria post lysis was approximately 1:1 (1552 mitochondria, 743 were gated as functional and 716 were gated as non-functional, with the remainder not gated; the gates for each population of mitochondria are highlighted in FIG. 19).

Therefore, functional mitochondria can be sorted and collected, with residual unlysed cells and non-functional mitochondria excluded based on size and fluorescence intensity. Dual-labeling using multiple probes or a JC-1 probe (red spectrum; Invitrogen, Life Technologies Corp., Carlsbad, Calif.; T3168) can help to further distinguish functional from non-functional mitochondria. Probes for use in dual labeling include, but are not limited to, reduced oxidative state mitotracker probes (e.g., MitoTracker Red CM-H2XRos (Invitrogen, Life Technologies Corp., Carlsbad, Calif.; M7513), MitoTracker Orange CM-H2TMRos (Invitrogen, Life Technologies Corp., Carlsbad, Calif.; M7511) and accumulation dependent probes: JC-1 (red spectrum; Invitrogen, Life Technologies Corp., Carlsbad, Calif.; T3168), MitoTracker Deep Red FM (Invitrogen, Life Technologies Corp., Carlsbad, Calif.; M22426) and JC-1 (green spectrum; Invitrogen, Life Technologies Corp., Carlsbad, Calif.; T3168).

Example 10

Mitochondrial Isolation Using Differential Centrifugation

As described in this Example, differential centrifugation procedures can be employed to isolate and/or fractionate mitochondria present in a tissue. The key steps when isolating mitochondria from any tissue or cell are: (i) rupturing of cells by mechanical and/or chemical means, (ii) differential centrifugation at low speed to remove debris and extremely large cellular organelles (SPIN 1), and (iii) centrifugation at a higher speed to isolate and collect mitochondria (SPIN 2).

The tissue is weighed and washed twice with 1.5 ml of a commercially available Wash Buffer (MitoSciences, Abcam, plc, Cambridge, UK). The tissue is minced and placed in a pre-chilled Dounce homogenizer. Up to 2.0 ml of a commercially available Isolation Buffer (MitoSciences, Abcam, plc, Cambridge, UK) is added. The cells are ruptured using the Dounce homogenizer (10-40 strokes), and the homogenate is transferred to Eppendorf tubes. Each tube is filled to 2.0 nil with Isolation Buffer. The homogenate is centrifuged at 1,000 g for 10 minutes at 4° C. The supernatant is reserved and transferred into new tubes, each of which is filled to 2.0 ml with Isolation Buffer. The tubes are centrifuged at 12,000 g for 15 minutes at 4° C. The pellet is reserved. If desired, the supernatant is analyzed for quality. The pellet is washed twice by resuspending in 1.0 ml of Isolation Buffer supplemented with 10 µl of a commercially available protease inhibitor cocktail (MitoSciences, Abcam, plc, Cambridge, UK). The tubes are centrifuged at 12,000 g for 15 minutes at 4° C. After washing, the pellets are combined and resuspended in 500 µl of Isolation Buffer supplemented with protease inhibitor cocktail. If desired, aliquots are stored at −80° C. until use.

In one approach, mitochondria integrity is tested by Western blot screening for cytochrome c, porin, or cyclophilin D in the isolated mitochondria versus in the supernatant fraction using commercially available antibodies, such as antibodies MSA06, MSA03, and MSA04 (MitoSciences, Abcam, plc, Cambridge, UK). In another approach, mitochondrial samples are probed by Western blot to detect components of the mitochondrial complex, for example, using the commercially available OXPHOS Complexes Detection cocktail (MitoSciences, Abcam, plc, Cambridge, UK).

Example 11

Mitochondrial Isolation Using Sucrose Gradient Separation

The protocol employs the following reagents, which are commercially available: n-dodecyl-β-D-maltopyranoside (Lauryl maltoside; MS910; MitoSciences, Abcam, plc, Cambridge, UK), Phosphate buffered saline (PBS), Sucrose solutions 15, 20, 25, 27.5, 30 and 35%, double distilled water, a protease inhibitor cocktail (MitoSciences, Abcam, plc, Cambridge, UK), and 13×51 mm polyallomer centrifuge tubes (Beckman 326819; Beckman-Coulter, Inc., Brea, Calif.).

The sucrose gradient separation procedure is a protein subfractionation method optimized for mitochondria. This method resolves a sample into at least 10 fractions. It is possible to separate solubilized whole cells into fractions of much lower complexity but when analyzing already isolated mitochondria the fractions are even more simplified. The sucrose gradient separation technique is designed for an initial sample volume of up to 0.5 ml at 5 mg/ml protein. Therefore 2.5 mg or less of total protein should be used. For larger amounts, multiple gradients can be prepared or larger scale gradients are made.

The sample is solubilized in anon-ionic detergent. It has been determined that at this protein concentration mitochondria are completely solubilized by 20 mM n-dodecyl-O-D-maltopyranoside (1% w/v lauryl maltoside). The key to this solubilization process is that the membranes are disrupted while the previously membrane embedded multisubunit OXPHOS complexes remain intact, a step necessary for the density based sucrose separation procedure described herein. One important exception is the pyruvate dehydrogenase enzyme (PDH). In order to isolate PDH at a protein concentration of 5 mg/ml mitochondria, the required detergent concentration is only 10 mM (0.5%) lauryl maltoside. The PDH enzyme should also be centrifuged at lower speeds, a centrifugal force of 16 000 g is maximum for the PDH complex.

To a mitochondrial membrane suspension at 5 mg/ml protein in PBS, lauryl maltoside is added to a final concentration of 1%. This is mixed well and incubated on ice for 30 minutes. The mixture is then centrifuged at 72,000 g for 30 minutes. A Beckman Optima benchtop ultracentrifuge (Beckman-Coulter, Inc., Brea, Calif.) is recommended for small sample volumes. However, at a minimum a benchtop microfuge, on maximum speed (e.g., about 16 000 g) should suffice. After centrifugation, the supernatant is collected and the pellet discarded. A protease inhibitor cocktail is added to the sample, which is maintained on ice until centrifugation is performed. In samples very rich in mitochondria the cytochromes in complexes III and IV may give the supernatant a brown color, which is useful when checking the effectiveness of the following separation.

A discontinuous sucrose density gradient is prepared by layering successive decreasing sucrose densities solutions upon one another. The preparation and centrifugation of a discontinuous gradient containing sucrose solutions from 15-35% is described in detail below. This gradient gives good separation of the mitochondrial OXPHOS complexes (masses ranging from 200 kDa to 1000 kDa). However this setup can be modified for the separation of a particular complex or for the separation of larger amounts of material.

The gradient is prepared by layering progressively less dense sucrose solutions upon one another; therefore the first solution applied is the 35% sucrose solution. A steady application of the solutions yields the most reproducible gradient. To aid in this application, a Beckman polyallomer tube is held upright in a tube stand. Next a Rainin Pipetman 200 µl pipette tip is placed on the end of a Rainin Pipetrnan 1000 µl pipette tip. Both snugly fitting tips are held steady by a clamp stand and the end of the 200 µl pipette tip is allowed to make contact with the inside wall of the tube. Sucrose solutions are then placed inside the 1000 µl pipette tip and fed into the tube slowly and steadily, starting with the 35% solution (0.25 ml).

Once the 35% solution has drained into the tube, the 30% solution (0.5 ml) is loaded into the tube on top of the 35% solution. This procedure is continued with the 27.5% (0.75 ml), 25% (1.0 ml), 20% (1.0 ml) and 15% (1.0 ml) solutions, respectively. Enough space is left at the top of the tube to add the 0.5 ml sample of solubilized mitochondria.

Once the sucrose gradient is poured discrete layers of sucrose are visible. Having applied the sample to the top of the gradient the tube is loaded into the rotor very carefully, and centrifugation begins. All centrifugation procedures require a balanced rotor therefore another tube containing precisely the same mass is generated. In practice this means 2 gradients must be prepared although the second gradient need not contain an experimental sample but could contain 0.5 ml water in place of the 0.5 ml protein sample.

The polyallomer tubes should be centrifuged in a swinging bucket SW 50.1 type rotor (Beckman-Coulter, Inc., Brea, Calif.) at 37,500 rpm (Relative Centrifugal Force avg. 132,000×g) for 16 hours 30 minutes at 4° C. with an acceleration profile of 7 and deceleration profile of 7. Immediately after the run the tube should be removed from the rotor, taking great care not to disturb the layers of sucrose. When separating a sample rich in mitochondria, discrete colored protein layers may be observed. Most often these are Complex III (500 kDa—brown color) approximately 10 mm from the bottom of the tube and Complex IV (200 kDa-green color) 25 mm from the bottom of the tube. In some circumstances additional bands can be observed. These are the other OXPHOS complexes.

For fraction collection, the tube is held steady and upright using a clamp stand. A tiny hole is introduced into the very bottom of the tube using a fine needle. The hole is just big enough to allow the sucrose solution to drip out at approximately 1 drop per second. Fractions of equal volume are collected in Eppendorf tubes below the pierced hole. A total of 10×0.5 ml fractions are appropriate, however collecting more fractions which are thus smaller in volume is also possible (e.g., 20×0.25 ml fractions). The fractions are stored at −80° C. until analysis. Collected fractions are analyzed to determine mitochondrial integrity using any of the methods described herein (e.g., in Example 9, 10) or known in the art.

Example 12

OSCs Exhibit Increased Mitochondrial Activity

It has been reported that low mitochondrial activity is a feature of "stemness", as it has been observed in spermatogonia, early embryo, inner cell mass cells and embryonic stem cells. See Ramalho-Santos et al., *Hum Reprod Update*. 2009 (5):553-72. OSCs are essentially the female equivalent of male spermatogonial stem cells (spermatogonia), however, it has now been determined that OSCs have prolific mitochondrial activity.

Figure 20:
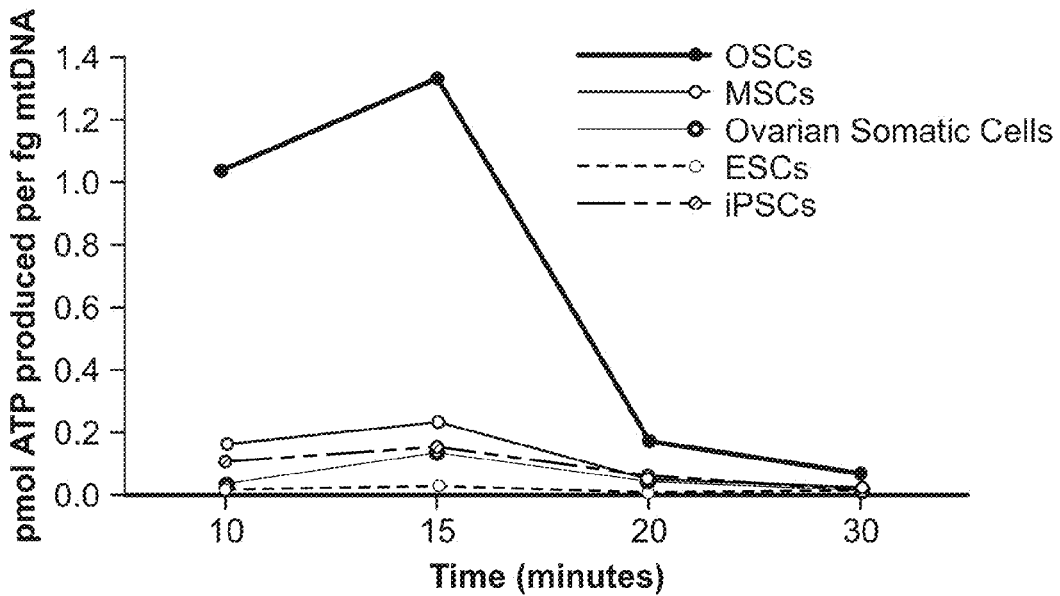
FIG. 20 depicts the kinetics of ATP production capacity by mitochondria isolated from different human cell types.

Following OSC lysis, mitochondrial production of ATP (pmol) was measured at 10, 15, 20 and 30 minutes, and then standardized against total mtDNA content (fg) in each sample tested (ATP Bioluminescence Assay Kit HS II, Roche Applied Science, Mannheim, Germany). As shown in FIG. 20, adult human ovary-derived oogonial stem cells (OSCs), obtained from female patients between 22-33 (28.5±4.0) years of age with Gender Identity Disorder for sex reassignment at Saitama Medical Center, generated much greater levels of ATP than human mesenchymal stem cells from bone marrow (hMSCs, obtained from PromoCell GmbH, Heidelberg, Germany), adult human ovarian somatic cells (subject matched to the OSCs used), human embryonic stem cells (ESCs), and human induced pluripotent stem cells (iPSCs) derived from IMR90 fetal lung fibroblasts.

Figure 21:
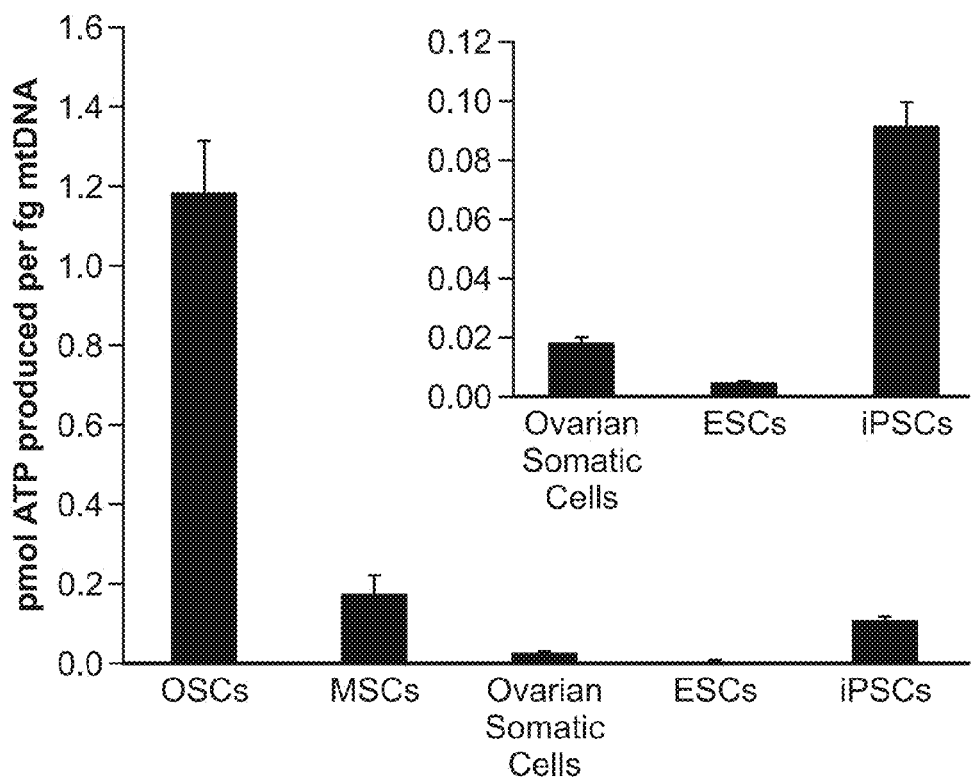
FIG. 21 depicts ATP production capacity over 10 minutes by mitochondria isolated from different human cell types.

Mitochondrial production of ATP (pmol) was standardized against total mtDNA content (fg) in each sample tested. As shown in FIG. 21, mitochondria isolated from adult human ovary-derived oogonial stem cells (OSCs) produced greater than 6-fold more ATP in 10 minutes than human mesenchymal stem cells (MSCs) from bone marrow and over 10-fold more ATP in 10 minutes than adult human ovarian somatic cells (subject matched to the OSCs used), human embryonic stem cells (ESCs), and human induced pluripotent stem cells (iPSCs) derived from IMR90 fetal lung fibroblasts. FIG. 21 depicts 1.03E-09, 1.46E-10, 1.76E-11, 4.56E-12, 9.10E-11 pmol ATP generated in 10 minutes for hOSC, hMSC, Soma, hESC, and hiPSC, respectively.

Standard errors (in the same order) are 1.15E-10, 4.56E-11, 2.28E-12, 1.72E-13 and 7.99E-12.

Figure 15:
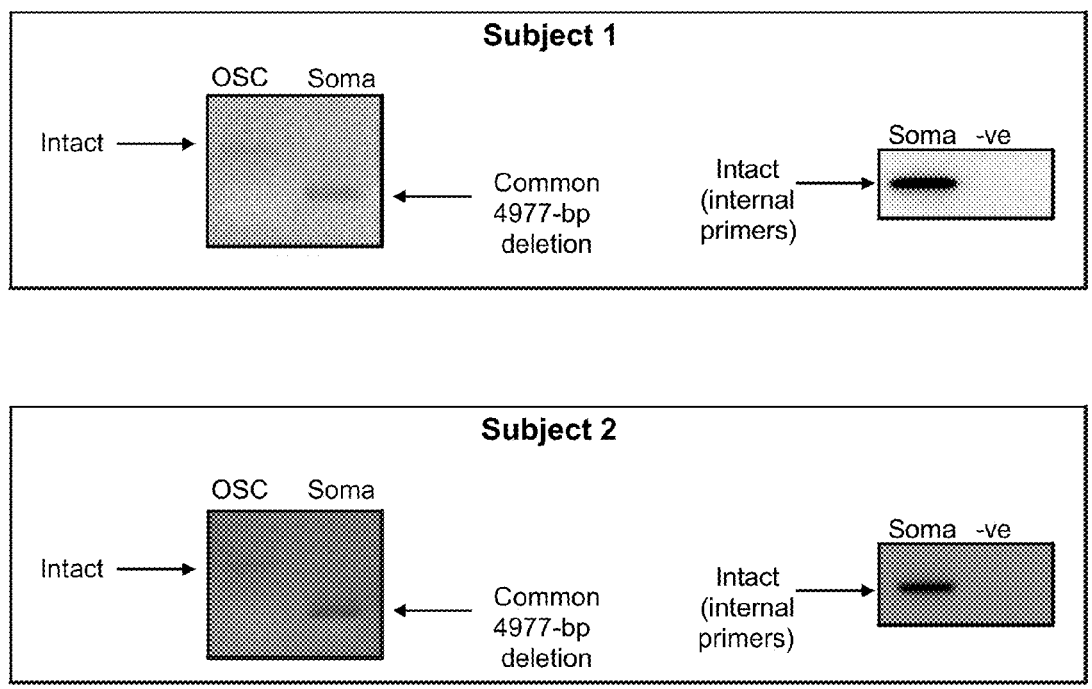
FIG. 15 depicts PCR analysis of the 4977-bp deletion in mtDNA from cultured OSCs and patient matched ovarian somatic cells.
Figure 22:
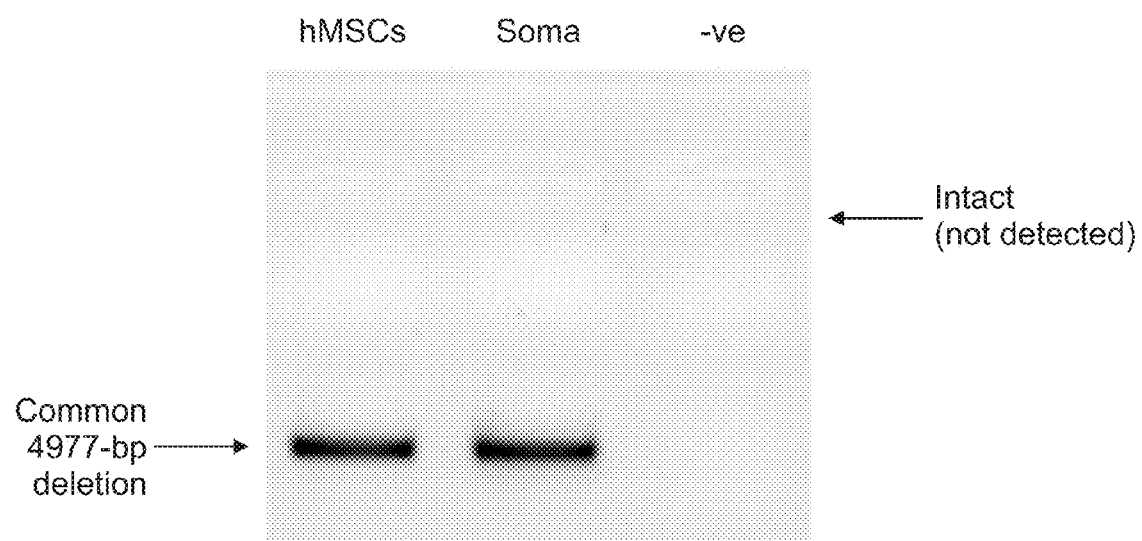
FIG. 22 depicts mtDNA deletion analysis in human mesenchymal stem cells and human ovarian soma.

Deletion analysis revealed the presence of the common 4977-bp deletion in hMSCs (FIG. 22). Human ovarian soma, which is known to have the mutation, is included as a positive control along with a no sample control (ye). The intact portion of the product was not detected in either sample. By comparison, the common 4977-bp deletion is not detectable in human OSCs (FIG. 15).

Other Embodiments

From the foregoing description, it will be apparent that variations and modifications may be made to the invention described herein to adapt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application contains subject matter that may be related to U.S. provisional application Ser. No. 61/502,840, filed Jun. 29, 2011 and U.S. provisional application Ser. No. 61/600,529, filed Feb. 17, 2012, the entire disclosures of which are incorporated herein by reference. All patents and publications mentioned in this specification are herein incorporated by reference to the same extent as if each independent patent and publication was specifically and individually indicated to be incorporated by reference.

What is claimed is:

1. A composition comprising i) functional mitochondria obtained from an ovarian oogonial stem cell (OSC) or the progeny of an ovarian OSC, wherein the OSC is a non-embryonic stem cell that is mitotically competent and expresses Vasa, Oct-4, Dazl, Stella, and optionally, a stage-specific embryonic antigen and ii) a fluorescent mitochondrial tracking probe bound to the functional mitochondria.

2. The composition of claim 1, wherein the tracking probe is a non-oxidation dependent probe, an accumulation dependent probe or a reduced oxidative state probe.

3. The composition of claim 1 or claim 2, wherein the mitochondria are obtained by centrifugation.

4. The composition of claim 1 or claim 2, wherein the mitochondria are obtained by mitochondrial membrane potential dependent cell sorting.

5. The composition of claim 1 or claim 2, wherein the composition comprises $1\times10^3$ to $5\times10^4$ mitochondria.

6. The composition of claim 1 or claim 2, wherein the OSC or progeny of the OSC produces at least 5-fold more ATP per fg mtDNA than an ovarian somatic cell or mesenchymal stem cell.

7. The composition of claim 6, wherein the ovarian somatic cell is autologous.

8. The composition of claim 1 or claim 2, wherein the composition is (a) a purified preparation of mitochondria from the OSC or the progeny of the OSC or (b) the cytoplasm of the OSC or the progeny of the OSC without a nucleus.

9. The composition of claim 1 or claim 2, wherein more than 2 percent, more than 5 percent, more than 10 percent or more than 20 percent of the mitochondria are functional mitochondria.

10. The composition of claim 1 or claim 2, wherein at least 75 percent, 85 percent or 90 percent of the functional mitochondria in the composition are high ATP-generating capacity mitochondria.

11. The composition of claim 1 or claim 2, wherein the OSC or the progeny of an OSC produces at least two fold more, at least three fold more, at least four fold more or at least ten fold more ATP per fg mtDNA than an ovarian somatic cell.

12. The composition of claim 11, wherein the ovarian somatic cell is autologous to the OSC or progeny of an OSC.

13. The composition of claim 1 or claim 2, wherein the OSC or the progeny of an OSC produces at least twofold more, at least three fold more, at least four fold more or at least ten fold more ATP per fg mtDNA than a mesenchymal stem cell.

14. The composition of claim 1 or claim 2, wherein the functional mitochondria are determined as being functional mitochondria by the steps of:
   (a) sorting the mitochondria based upon binding of the tracking probe; and
   (b) determining the percentage of functional mitochondria based on the percentage of mitochondria which bind the tracking probe.

15. The composition of claim 1 or claim 2, wherein the ovarian OSC or the progeny of an ovarian OSC is obtained from a mammal.

16. The composition of claim 1 or claim 2, wherein the ovarian OSC or the progeny of an ovarian OSC is obtained from a human.

17. The composition of claim 16, wherein the human is a female of advanced maternal age.

* * * * *

SEQUENCE LISTING

```
<160> NUMBER OF SEQ ID NOS: 67

<210> SEQ ID NO 1
<211> LENGTH: 4
<212> TYPE: PRT
<213> ORGANISM: Unknown
<220> FEATURE:
<223> OTHER INFORMATION: Description of Unknown: "DEAD" box
      motif peptide

<400> SEQUENCE: 1

Asp Glu Ala Asp
1
```

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cggaaagcaa cccaaagcaa tac                                              23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cctcggaacc ataggaaaca ttc                                              23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cccaatgaag gaccctgaaa c                                                21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatggctcac tgtcccgttc a                                                21

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gttatcacca ttgttagtgt catc                                             24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatgagtgtt acacctgcgt g                                                21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgccaatatg atcaggcact cg                                              22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
actgcgtata gcacctgtca cc                                              22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggaaaccagc agcaagtgat                                                 20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tggagtcctc atcctctgg                                                  19

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtgtgtcgaa gggctatgga t                                               21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acaggcagct gatatccagt g                                               21

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14 cctcccact ttcccataat                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aatgggtggg gaagaaaaac                                                   20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agcagagagc ttggtcggg                                                    19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tccggtgagc tgtcgctgtc                                                   20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctcacgcttc cacaacaaga                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tctcggggct gtcataaatc                                                   20

<210> SEQ ID NO 20
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cccttcagtc acagtttccg t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtctctactc tagtgccttc g                                              21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgtcagtccc aaccattctt                                                20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ttgttggtga gcatccatgt                                                20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgcctccttc cctcatcttg                                                20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cacttccccc gctcacacag                                                20

<210> SEQ ID NO 26
<211> LENGTH: 20
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtccgactcc tgcagagaac                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgatggtgaa gcgctgatag                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aaggtcttga gcaggaacga                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gggtggaaag tagtgcggta                                              20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccgagctgtg caattcccag a                                            21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aaccctctga gccaagggtg a                                            21

<210> SEQ ID NO 32
<211> LENGTH: 21
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 32
gatgacgata tcgctgcgct g                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtacgaccag aggcatacag g                                              21

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaacatgacc ggctacaaga ccct                                           24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggcacacctt gcattggtat ggtt                                           24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agcagtcctc agggaaatcg aaga                                           24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tatggctgaa gtggcttggt gtct                                           24

<210> SEQ ID NO 38
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 38
atgtcgtctg gtccctgttc                                                   20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gggatgacga tgagcagaat                                                   20

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agacggtgtg caccaacatc taca                                              24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgtcgagtca gcttgagcag gaat                                              24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ttgttgctgt tggacaagtg ggtg                                              24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcaacaagaa ctgggcactt tcca                                              24

<210> SEQ ID NO 44
<211> LENGTH: 24
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 44
tcgaactggt gtgtccaaag gcta                                              24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
taggattcat cgtggttgtg ggct                                              24

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
accctaccca gtaccctgct                                                   20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcaagaaaag caaccaggag                                                   20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tatggtgtcc tccggaaaaa                                                   20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aactccaact ccttccagca                                                   20

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
ataaacgccg agagattgcc caga                                           24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aagtctggtc agaagtcagc agca                                           24

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
caagcacaat ttgctcagga                                                20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggcacgtagg cagaataagc                                                20

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tcacctctac aacactgttc ggct                                           24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aaggttgaag gaggctggtc acat                                           24

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 56
cgccatgttc tctgtctcaa                                                     20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cgtttgttca catcccagtg                                                     20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tcttcttcgc ccttgtgact                                                     20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctcagggtga gcttttctgg                                                     20

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
agcaggaccc agatgaactc aaca                                                24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aagcccactg ctctacttca tggt                                                24

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 62
catgtacgtt gctatccagg c                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ctccttaatg tcacgcacga t                                              21

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ttacactatt cctcatcacc caac                                           24

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tgtgaggaaa ggtattcctg ct                                             22

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cctacccctc acaatcatgg                                                20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
atcgggtgat gatagccaag                                                20
```